(12) United States Patent
Yeo et al.

(10) Patent No.: US 12,139,710 B2
(45) Date of Patent: Nov. 12, 2024

(54) METHODS OF MODULATING RNA TRANSLATION

(71) Applicant: The Regents of the University of California, La Jolla, CA (US)

(72) Inventors: Eugene Yeo, La Jolla, CA (US); En-Ching Luo, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/512,270

(22) Filed: Oct. 27, 2021

(65) Prior Publication Data

US 2022/0127611 A1 Apr. 28, 2022

Related U.S. Application Data

(60) Provisional application No. 63/106,631, filed on Oct. 28, 2020.

(51) Int. Cl.
| | | |
|---|---|---|
| *C07H 21/02* | (2006.01) | |
| *C12N 7/00* | (2006.01) | |
| *C12N 15/113* | (2010.01) | |

(52) U.S. Cl.
CPC .............. *C12N 15/113* (2013.01); *C12N 7/00* (2013.01); *C12N 2310/113* (2013.01); *C12N 2310/141* (2013.01); *C12N 2310/321* (2013.01); *C12N 2310/531* (2013.01)

(58) Field of Classification Search
CPC .......................... C12N 15/113; C12N 2310/20
See application file for complete search history.

(56) References Cited

U.S. PATENT DOCUMENTS

| | | | |
|---|---|---|---|
| 2011/0287412 A1 | 11/2011 | Landthaler et al. | |
| 2014/0378316 A1 | 12/2014 | Darnell et al. | |
| 2018/0073018 A1* | 3/2018 | Hu | ......................... A61P 31/00 |
| 2023/0374566 A1 | 11/2023 | Yeo et al. | |

FOREIGN PATENT DOCUMENTS

| | | |
|---|---|---|
| WO | WO 2017/091630 | 6/2017 |
| WO | WO 2021/202542 | 10/2021 |

OTHER PUBLICATIONS

Lino et al. (Drug Delivery, 2018, 25, 1, 1234-1257).*
Polstein et al. (Nature Chemical Biology, 11, 2015, 198-200).*
Aucagne et al. (The FASEB Journal, 2017, 31, 5012-5018).*
Luo et al. (Nature Structural & Molecular Biology, vol. 27, Oct. 2020, 989-1000).*
International Preliminary Report on Patentability in International Appln. No. PCT/US2021/051952, mailed on Apr. 6, 2023, 9 pages.
Andreev et al., "Translation control of mRNAs encoding mammalian translation initiation factors," Gene, Apr. 2018, 651:174-182.
Ashburner et al., "Gene Ontology: tool for the unification of biology," Nature Genetics, May 2000, 25:25-29.
Attwood et al., "PRINTS and its automatic supplement, prePRINTS," Nucleic Acids Research, Jan. 2003, 31(1):400-402.
Baltz et al., "The mRNA-Bound Proteome and Its Global Occupancy Profile on Protein-Coding Transcripts," Molecular Cell, Jun. 2012, 46(5):674-690.
Batra et al., "Elimination of Toxic Microsatellite Repeat Expansion RNA by RNA-Targeting Cas9," Cell, Aug. 2017, 170(5):899-912.
Beckmann et al., "The RNA-binding proteomes from yeast to man harbour conserved enigmRBPs," Nature Communications, Dec. 2015, 6(10127):1-9.
Benjamini et al., "Adaptive linear step-up procedures that control the false discovery rate," Biometrika, Sep. 2006, 93(3):491-507.
Bicknell et al., "When mRNA translation meets decay," Biochemical Society Transactions, Apr. 2017, 45(2):339-351.
Boelens et al., "The human U1 snRNP-Specific U1A protein inhibits polyadenylation of its own pre-mRNA," Cell, Mar. 1993, 72(6):881-892.
Bos et al., "Tethered Function Assays as Tools to Elucidate the Molecular Roles of RNA-Binding Proteins," Advances in Experimental Medicine and Biology, Jun. 2016, 907:61-88.
Brannan et al., "SONAR Discovers RNA-Binding Proteins from Analysis of Large-Scale Protein-Protein Interactomes," Molecular Cell, Oct. 2016, 64(2):282-293.
Busan et al., "Guidelines for SHAPE Reagent Choice and Detection Strategy for RNA Structure Probing Studies," Biochemistry, May 2019, 58:2655-2664.
Cano et al., "A non-proteolytic role for ubiquitin in deadenylation of MHC-I mRNA by the RNA-binding E3-ligase MEX-3C," Nature Communications, Oct. 2015, 6(8670):1-8.
Castello et al., "Comprehensive Identification of RNA-Binding Domains in Human Cells," Molecular Cell, Aug. 2016, 63(4):696-710.
Castello et al., "Insights into RNA Biology from an Atlas of Mammalian mRNA-Binding Proteins," Cell, Jun. 2012, 149(6):1393-1406.
Chen et al., "Functional dissection of hnRNP D suggests that nuclear import is required before hnRNP D can modulate mRNA turnover in the cytoplasm," RNA, 2004, 10:669-680.
Cirillo et al., "UBAP2L Forms Distinct Cores that Act in Nucleating Stress Granules Upstream of G3BP1," Current Biology, Feb. 2020, 30(4):698-707.
Clement et al., "A Tethering Approach to Study Proteins that Activate mRNA Turnover in Human Cells," Methods In Molecular Biology, 2008, 419:121-133.
Clery et al., "From Structure to Function of RNA Binding Domains," RNA Binding Proteins, 2011, 137-158.

(Continued)

*Primary Examiner* — Amy Rose Hudson
(74) *Attorney, Agent, or Firm* — Fish & Richardson P.C.

(57) ABSTRACT

Provided are methods of modulating gene expression of a target RNA in a cell comprising (a) recruiting a modulation unit, wherein the modulation unit comprises an RNA binding protein (RBP), an exogenous RNA binding moiety, and a gene-editing agent; (b) delivering the modulation unit into the cell; and (c) detecting change in the target RNA translation, wherein the modulation unit modulates gene expression of the target RNA in the cell.

11 Claims, 51 Drawing Sheets
(47 of 51 Drawing Sheet(s) Filed in Color)
Specification includes a Sequence Listing.

(56) References Cited

OTHER PUBLICATIONS

Coller et al., "mRNA stabilization by poly(A) binding protein is independent of poly(A) and requires translation," Genes & Development, 1998, 12:3226-3235.
Coller et al., "Tethered function assays using 3' untranslated regions," Methods, Feb. 2002, 26(2):142-150.
Coller et al., "Tethered Function Assays: An Adaptable Approach to Study RNA Regulatory Proteins," Methods in Enzymology, 2007, 429:299-321.
Colombrita et al., "TDP-43 and FUS RNA-binding Proteins Bind Distinct Sets of Cytoplasmic Messenger RNAs and Differently Regulate Their Post-transcriptional Fate in Motoneuron-like Cells," Journal of Biological Chemistry, May 2012, 287(19):15635-15647.
Conway et al., "Enhanced CLIP Uncovers IMP Protein-RNA Targets in Human Pluripotent Stem Cells Important for Cell Adhesion and Survival," Cell Reports, Apr. 2016, 15(3):666-679.
Corley et al., "Footprinting SHAPE-eCLIP Reveals Transcriptome-wide Hydrogen Bonds at RNA-Protein Interfaces," Molecular Cell, Dec. 2020, 80(5):903-914.
Corley et al., "How RNA-Binding Proteins Interact with RNA: Molecules and Mechanisms," Molecular Cell, Apr. 2020, 78(1):9-29.
Cox et al., "RNA editing with CRISPR-Cas13," Science, Oct. 2017, 358(6366):1019-1027.
Deigan et al., "Accurate SHAPE-directed RNA structure determination," Proceedings of the National Academy of Sciences (PNAS), Jan. 2009, 106(1):97-102.
Deragon et al., "The role of LARP1 in translation and beyond," Wiley Interdisciplinary Reviews RNA, 2015, 6(4):399-417.
Di Sanzo et al., "shRNA targeting of ferritin heavy chain activates H19/miR-675 axis in K562 cells," Gene, May 2018, 657:92-99.
Ding et al., "In vivo genome-wide profiling of RNA secondary structure reveals novel regulatory features," Nature, 2014, 505:696-700.
Diribarne et al., "7SK RNA, a non-coding RNA regulating P-TEFb, a general transcription factor," RNA Biology, Apr. 2009, 6(2):122-128.
Dobin et al., "STAR: ultrafast universal RNA-seq aligner," Bioinformatics, Jan. 2013, 29(1):15-21.
Doench et al., "Rational design of highly active sgRNAs for CRISPR-Cas9-mediated gene inactivation," Nature Biotechnology, Dec. 2014, 32(12):1262-1267.
Dominguez et al., "Sequence, Structure, and Context Preferences of Human RNA Binding Proteins," Molecular Cell, Jun. 2018, 70(5):854-867.e9.
Duncan et al., "The Clk2 and Clk3 Dual-Specificity Protein Kinases Regulate the Intranuclear Distribution of SR Proteins and Influence Pre-mRNA Splicing," Experimental Cell Research, Jun. 1998, 241(2):300-308.
Feng et al., "Light-activated chemical probing of nucleobase solvent accessibility inside cells," Nature Chemical Biology, Jan. 2018, 14:276-283.
Fensterl et al., "Interferon-Induced Ifit Proteins: Their Role in Viral Pathogenesis," Journal of Virology, Mar. 2015, 89(5):2462-2468.
Fillebeen et al., "Electrophoretic Mobility Shift Assay (EMSA) for the Study of RNA-Protein Interactions: The IRE/IRP Example," Journal of Visualized Experiments, Dec. 2014, 94(e52230):1-9.
Fiorini et al., "Human Upf1 is a highly processive RNA helicase and translocase with RNP remodelling activities," Nature Communications, Jul. 2015, 6(7581):1-10.
Fischer et al., "Structure-Mediated RNA Decay by UPF1 and G3BP1," Molecular Cell, Apr. 2020, 78(1):70-84.
Flores et al., "Structural Changes of RNA in Complex with Proteins in the SRP," Frontiers in Molecular Biosciences, Feb. 2018, 5(7):1-8.
Flynn et al., "Transcriptome-wide interrogation of RNA secondary structure in living cells with icSHAPE," Nature Protocols, Jan. 2016, 11(2):273-290.
Fu et al., "DAZ Family Proteins, Key Players for Germ Cell Development," International Journal of Biological Sciences, 2015, 11(10):1226-1235.
Fujii et al., "Decoding the Function of Expansion Segments in Ribosomes," Molecular Cell, Dec. 2018, 72(6):1013-1020.
Garneau et al., "The highways and byways of mRNA decay," Nature Reviews Molecular Cell Biology, Feb. 2007, 8:113-126.
Gehman et al., "The splicing regulator Rbfox1 (A2BP1) controls neuronal excitation in the mammalian brain," Nature Genetics, May 2011, 43(7):706-711.
Gerstberger et al., "A census of human RNA-binding proteins," Nature Reviews Genetics, Nov. 2014, 15(12):829-845.
Gerstberger et al., "Evolutionary Conservation and Expression of Human RNA-Binding Proteins and Their Role in Human Genetic Disease," Advances in Experimental Medicine Biology, Aug. 2014, 825:1-55.
Graham et al., "Resources for the design of CRISPR gene editing experiments," Genome Biology, Nov. 2015, 16(260):1-21.
Graindorge et al., "In-cell identification and measurement of RNA-protein interactions," Nature Communication, Nov. 2019, 10(5317):1-11.
Gray et al., "Cardiac Hypertrophy: A tail of translational regulation," Elife, Jun. 2017, 6(e29104):1-4.
Hafner et al., "Transcriptome-wide Identification of RNA-Binding Protein and MicroRNA Target Sites by PAR-CLIP," Cell, Apr. 2010, 141(1):129-141.
Hainzl et al., "Structural insights into SRP RNA: An induced fit mechanism for SRP assembly," RNA, May 2005, 11:1043-1050.
Hanson et al., "Translation elongation and mRNA stability are coupled through the ribosomal A-site," RNA, 2018, 24:1377-1389.
Hockensmith et al., "Laser cross-linking of nucleic acids to proteins. Methodology and first applications to the phage T4 DNA replication system," Journal of Biological Chemistry, Mar. 1986, 261(8):3512-3518.
Hu et al., "A structural dissection of protein-RNA interactions based on different RNA base areas of interfaces," RSC Advances, 2018, 8:10582-10592.
Hu et al., "Cpeb4-Mediated Translational Regulatory Circuitry Controls Terminal Erythroid Differentiation," Development Cell, Sep. 2014, 30(6):660-672.
International Search Report and Written Opinion in International Appln. No. PCT/US2021/051952, dated Jan. 18, 2022, 11 pages.
Jackson et al., "The mechanism of eukaryotic translation initiation and principles of its regulation," Nature Reviews Molecular Cell Biology, Feb. 2010, 11:113-127.
Julaton et al., "NANOS3 function in human germ cell development," Human Molecular Genetics, Jun. 2011, 20(11):2238-2250.
Kapeli et al., "Distinct and shared functions of ALS-associated proteins TDP-43, FUS and TAF15 revealed by multisystem analyses," Nature Communications, Jul. 2016, 7(12143):1-14.
Kazan et al., "RNAcontext: A New Method for Learning the Sequence and Structure Binding Preferences of RNA-Binding Proteins," PLoS Computational Biology, Jul. 2010, 6(7):e1000832.
Konig et al., "iCLIP reveals the function of hnRNP particles in splicing at individual nucleotide resolution," Nature Structural & Molecular Biology, Jul. 2010, 17(7):909-915.
Lackey et al., "Allele-specific SHAPE-MaP assessment of the effects of somatic variation and protein binding on mRNA structure," RNA, Jan. 2018, 24:513-528.
Le Quesne et al., "Derivation of a structural model for the c-myc IRES," Journal of Molecular Biology, Jun. 2001, 310(1):111-126.
Lee et al., "Advances in CLIP Technologies for Studies of Protein-RNA Interactions," Molecular Cell, Feb. 2018, 69(3):354-369.
Lee et al., "Integrative analysis reveals RNA G-quadruplexes in UTRs are selectively constrained and enriched for functional associations," Nature Communications, Jan. 2020, 11(527):1-12.
Leppek et al., "Functional 5' UTR mRNA structures in eukaryotic translation regulation and how to find them," Nature Reviews Molecular Cell Biology, 2018, 19:158-174.
Leulliot et al., "Current Topics in RNA-Protein Recognition: Control of Specificity and Biological Function through Induced Fit and Conformational Capture," Biochemistry, 2001, 40(27):7947-7956.

(56) References Cited

OTHER PUBLICATIONS

Levi et al., "Neurodegeneration with Brain Iron Accumulation Disorders: Valuable Models Aimed at Understanding the Pathogenesis of Iron Deposition," Pharmaceuticals, 2019, 12(1):27.
Li et al., "The Sequence Alignment/Map format and SAMtools," Bioinformatics, Aug. 2009, 25(16):2078-2079.
Liang et al., "Stepping Out of the Cytosol: AIMp1/p43 Potentiates the Link Between Innate and Adaptive Immunity," International Reviews of Immunology, Sep. 2015, 34(5):367-381.
Licatalosi et al., "HITS-CLIP yields genome-wide insights into brain alternative RNA processing," Nature, Nov. 2008, 456:464-469.
Liu et al., "Characterizing inactive ribosomes in translational profiling," Translation, 2016, 4(1):e1138018.
Lorenz et al., "ViennaRNA Package 2.0," Algorithms for Molecular Biology, Nov. 2011, 6(26):1-14.
Lotfi et al., "RNA secondary structure prediction based on SHAPE data in helix regions," Journal of Theoretical Biology, Sep. 2015, 380:178-182.
Loughlin et al., "The Solution Structure of FUS Bound to RNA Reveals a Bipartite Mode of RNA Recognition with Both Sequence and Shape Specificity," Molecular Cell, Feb. 2019, 73(3):490-504.e6.
Lovci et al., "Rbfox proteins regulate alternative mRNA splicing through evolutionarily conserved RNA bridges," Nature Structural & Molecular Biology, Nov. 2013, 20:1434-1442.
Love et al., "Moderated estimation of fold change and dispersion for RNA-seq data with DESeq2," Genome Biology, Dec. 2014, 15(550):1-21.
Low et al., "SHAPE-directed RNA secondary structure prediction," Methods, Oct. 2010, 52(2):150-158.
Lu et al., "RNA Duplex Map in Living Cells Reveals Higher-Order Transcriptome Structure," Cell, May 2016, 165(5):1267-1279.
Lukong et al., "RNA-binding proteins in human genetic disease," Trends in Genetics, Aug. 2008, 24(8):416-425.
Luna et al., "New clues to understand the role of THO and other functionally related factors in mRNP biogenesis," Biochimica et Biophysica Acta (BBA), Jun. 2012, 1819(6):514-520.
Luo et al., "Large-scale tethered function assays identify factors that regulate mRNA stability and translation," Nature Structural & Molecular Biology, Oct. 2020, 27(10):989-1000.
Lutz et al., "The snRNP-free U1A (Sf-A) complex(es): Identification of the largest subunit as PSF, the polypyrimidine-tract binding protein-associated splicing factor," RNA, Dec. 1998, 4(12):1493-1499.
Lykke-Andersen et al., "Recruitment and activation of mRNA decay enzymes by two ARE-mediated decay activation domains in the proteins TTP and BRF-1," Genes & Development, 2005, 19:351-361.
Maeda et al., "Arginine methylation of ubiquitin-associated protein 2-like is required for the accurate distribution of chromosomes," FASEB Journal, 2016, 30:312-323.
Markmiller et al., "Context-Dependent and Disease-Specific Diversity in Protein Interactions within Stress Granules," Cell, Jan. 2018, 172(3):590-604.
Martin et al., "Systematic reconstruction of RNA functional motifs with high-throughput microfluidics," Nature Methods, 2012, 9(12):1192-1194.
Martin, "Cutadapt Removes Adapter Sequences From High-Throughput Sequencing Reads," EMBnet.journal, 2011, 17(1):10-12.
Martinez et al., "Protein-RNA Networks Regulated by Normal and ALS-Associated Mutant HNRNPA2B1 in the Nervous System," Neuron, Nov. 2016, 92(4):780-795.
Maticzka et al., "GraphProt: modeling binding preferences of RNA-binding proteins," Genome Biology, Jan. 2014, 15(R17):1-18.
McDonald et al., "Satisfying Hydrogen Bonding Potential in Proteins," Journal of Molecular Biology, May 1994, 238(5):777-793.

McGinnis et al., "High-Throughput SHAPE and Hydroxyl Radical Analysis of RNA Structure and Ribonucleoprotein Assembly," Methods in Enzymology, 2009, 468:67-89.
Meng et al., "Cytoplasmic Metadherin (MTDH) Provides Survival Advantage under Conditions of Stress by Acting as RNA-binding Protein," Journal of Biological Chemistry, Feb. 2012, 287(7):4485-4491.
Meng et al., "Drug Resistance Mediated by AEG-1/MTDH/LYRIC," Advances in Cancer Research, 2013, 120:135-157.
Miyasaka et al., "Interaction of antiproliferative protein Tob with the CCR4-NOT deadenylase complex," Cancer Science, Apr. 2008, 99(4):755-761.
Moore et al., "Human Pumilio-2 is expressed in embryonic stem cells and germ cells and interacts with DAZ (Deleted in AZoospermia) and DAZ-like proteins," Proceedings of the National Academy of Sciences (PNAS), Jan. 2003,100(2):538-543.
Mukhopadhyay et al., "The GAIT system: a gatekeeper of inflammatory gene expression," Trends in Biochemistry Sciences, Jul. 2009, 34(7):324-331.
Mustoe et al., "RNA base-pairing complexity in living cells visualized by correlated chemical probing," Proceedings of the National Academy of Sciences (PNAS), Nov. 2019, 116(49):24574-24582.
Natchiar et al., "Visualization of chemical modifications in the human 80S ribosome structure," Nature, Nov. 2017, 551:472-477.
Nelles et al., "Programmable RNA Tracking in Live Cells with CRISPR/Cas9," Cell, Apr. 2016, 165(2):488-496.
Nishimura et al., "The eIF4E-Binding Protein 4E-T Is a Component of the mRNA Decay Machinery that Bridges the 5' and 3' Termini of Target mRNAs," Cell Reports, Jun. 2015, 11(9):1425-1436.
O'Connell et al., "Programmable RNA recognition and cleavage by CRISPR/Cas9," Nature, Sep. 2014, 516:263-266.
Pan et al., "Prediction of RNA-protein sequence and structure binding preferences using deep convolutional and recurrent neural networks," BMC Genomics, Jul. 2018, 19(511):1-11.
Popovic et al., "Iron accumulation and iron-regulatory protein activity in human hepatoma (HepG2) cells," Molecular and Cellular Biochemistry, Oct. 2004, 265:37-45.
Poria et al., "RNA-protein UV-crosslinking Assay," Bio-Protocol, Mar. 2017, 7(6):e2193.
Protter et al., "Principles and Properties of Stress Granules," Trends in Cell Biology, Sep. 2016, 26(9):668-679.
Punta et al., "The Pfam protein families database," Nucleic Acids Research, Jan. 2012, 40(D1):D290-D301.
Queiroz et al., "Comprehensive identification of RNA-protein interactions in any organism using orthogonal organic phase separation (OOPS)," Nature Biotechnology, Jan. 2019, 37:169-178.
Quinlan et al., "BEDTools: a flexible suite of utilities for comparing genomic features," Bioinformatics, Mar. 2010, 26(6):841-842.
Radhakrishnan et al., "Connections Underlying Translation and mRNA Stability," Journal of Molecular Biology, Sep. 2016, 428(18):3558-3564.
Ramachandran et al., "Statistical Analysis of SHAPE-Directed RNA Secondary Structure Modeling," Biochemistry, 2013, 52(4):596-599.
Rissland, "The organization and regulation of mRNA-protein complexes," Wiley Interdisciplinary Reviews RNA, 2017, 8:e1369.
Rosario et al., "RNA-binding proteins in human oogenesis: Balancing differentiation and self-renewal in the female fetal germline," Stem Cell Research, May 2017, 21:193-201.
Roy et al., "The intimate relationships of mRNA decay and translation," Trends in Genetics, Dec. 2013, 29(12):691-699.
Rual et al., "Human ORFeome Version 1.1: A Platform for Reverse Proteomics," Genome Research, 2004, 14:2128-2135.
Saria et al., "Discovering Deformable Motifs in Continuous Time Series Data," Proceedings of the Twenty-Second International Joint Conference on Artificial Intelligence, 2011, 2:1465-1471.
Schmidt et al., "SUnSET, a nonradioactive method to monitor protein synthesis," Nature Methods, 2009, 6:275-277.
Scotti et al., "RNA mis-splicing in disease," Nature Reviews Genetics, 2016, 17:19-32.
Siegfried et al., "RNA motif discovery by SHAPE and mutational profiling (SHAPE-MaP)," Nature Methods, Jul. 2014, 11:959-965.

(56) References Cited

OTHER PUBLICATIONS

Smith et al., "UMI-tools: modeling sequencing errors in Unique Molecular Identifiers to improve quantification accuracy," Genome Research, Jan. 2017, 27:491-499.
Smola et al., "Detection of RNA-Protein Interactions in Living Cells with SHAPE," Biochemistry, 2015, 54(46):6867-6875.
Smola et al., "In-cell RNA structure probing with SHAPE-MaP," Nature Protocols, 2018, 13(6):1181-1195.
Smola et al., "Selective 2'-hydroxyl acylation analyzed by primer extension and mutational profiling (SHAPE-MaP) for direct, versatile and accurate RNA structure analysis," Nature Protocols, Oct. 2015, 10(11):1643-1669.
Smola et al., "SHAPE reveals transcript-wide interactions, complex structural domains, and protein interactions across the Xist lncRNA in living cells," Proceedings of the National Academy of Sciences (PNAS), Aug. 2016, 113(37):10322-10327.
Spitale et al., "RNA SHAPE analysis in living cells," Nature Chemical Biology, Jan. 2013, 9:18-20.
Spitale et al., "Structural imprints in vivo decode RNA regulatory mechanisms," Nature, Mar. 2015, 519:486-490.
Stevens et al., "Two covariance models for iron-responsive elements," RNA Biology, 2011, 8(5):792-801.
Stys et al., "Iron Regulatory Protein 1 Outcompetes Iron Regulatory Protein 2 in Regulating Cellular Iron Homeostasis in Response to Nitric Oxide," Journal of Biological Chemistry, Jul. 2011, 286(26):22846-22854.
Sugimoto et al., "hiCLIP reveals the in vivo atlas of mRNA secondary structures recognized by Staufen 1," Nature, Mar. 2015, 519:491-494.
Sundararaman et al., "Resources for the Comprehensive Discovery of Functional RNA Elements," Molecular Cell, Mar. 2016, 61(6):903-913.
Tan et al., "Structure of Histone mRNA Stem-Loop, Human Stem-Loop Binding Protein, and 3'hExo Ternary Complex," Science, Jan. 2013, 339(6117):318-321.
The Gene Ontology Consortium, "Expansion of the Gene Ontology knowledgebase and resources," Nucleic Acids Research, Jan. 2017, 45(D1):D331-D338.
Tian et al., "Structural basis for piRNA 2'-O-methylated 3'-end recognition by Piwi PAZ (Piwi/Argonaute/Zwille) domains," Proceedings of the National Academy of Sciences (PNAS), Jan. 2011, 108(3):903-910.
Tijerina et al., "DMS footprinting of structured RNAs and RNA-protein complexes," Nature Protocols, Oct. 2007, 2:2608-2623.
Trendel et al., "The Human RNA-Binding Proteome and Its Dynamics during Translational Arrest," Cell, Jan. 2019, 176:391-403.
Ule et al., "An RNA map predicting Nova-dependent splicing regulation," Nature, Nov. 2006, 444:580-586.
Ule et al., "CLIP Identifies Nova-Regulated RNA Networks in the Brain," Science, Nov. 2003, 302(5648):1212-1215.
Urano et al., "Interaction of the conserved meiotic regulators, BOULE (BOL) and PUMILIO-2 (PUM2)," Molecular Reproduction & Development, Apr. 2005, 71(3):290-298.
Urdaneta et al., "Purification of cross-linked RNA-protein complexes by phenol-toluol extraction," Nature Communications, Mar. 2019, 10(990):1-17.
Van Nostrand et al., "A large-scale binding and functional map of human RNA-binding proteins," Nature, Jul. 2020, 583:711-719.
Van Nostrand et al., "Experimental and Computational Considerations in the Study of RNA-Binding Protein-RNA Interactions," Advances in Experimental Medicine and Biology, 2016, 907:1-28.
Van Nostrand et al., "Principles of RNA processing from analysis of enhanced CLIP maps for 150 RNA binding proteins," Genome Biology, Apr. 2020, 21(90):1-26.
Van Nostrand et al., "Robust transcriptome-wide discovery of RNA-binding protein binding sites with enhanced CLIP (eCLIP)," Nature Methods, Mar. 2016, 13(6):508-514.
Vicens et al., "Revisiting the Closed-Loop Model and the Nature of mRNA 5'-3' Communication," Molecular Cell, Dec. 2018, 72(5):805-812.
Walden et al., "Accommodating variety in iron-responsive elements: Crystal structure of transferrin receptor 1 B IRE bound to iron regulatory protein 1," FEBS Letters, Jan. 2012, 586(1):32-35.
Walden et al., "Structure of Dual Function Iron Regulatory Protein 1 Complexed with Ferritin IRE-RNA," Science, Dec. 2006, 314(5807):1903-1908.
Wang et al., "Mechanistic studies of a small-molecule modulator of SMN2 splicing," Proceedings of the National Academy of Sciences (PNAS), May 2018, 115(20):E4606-E4612.
Wang et al., "N6-methyladenosine-dependent regulation of messenger RNA stability," Nature, 2014, 505:117-120.
Wheeler et al., "Advances and challenges in the detection of transcriptome-wide protein-RNA interactions," Wiley Interdisciplinary Reviews RNA, 2018, 9:e1436.
Wilkinson et al., "Selective 2'-hydroxyl acylation analyzed by primer extension (SHAPE): quantitative RNA structure analysis at single nucleotide resolution," Nature Protocols, Nov. 2006, 1(3):1610-1616.
Williams et al., "Structural insights into E1 recognition and the ubiquitin-conjugating activity of the E2 enzyme Cdc34," Nature Communications, Jul. 2019, 10(3296):1-15.
Yang et al., "Solution structure of the LicT-RNA antitermination complex: CAT clamping RAT," The EMBO Journal, Apr. 2002, 21(8):1987-1997.
Youn et al., "High-Density Proximity Mapping Reveals the Subcellular Organization of mRNA-Associated Granules and Bodies," Molecular Cell, Feb. 2018, 69(3):517-532.
Zubradt et al., "DMS-MaPseq for genome-wide or targeted RNA structure probing in vivo," Nature Methods, 2017, 14:75-82.
Hu et al., "HIV-1 reverse transcription," Cold Spring Harbor Perspectives in Medicine, Oct. 1, 2012, 2(10): a006882.
Cook et al., "RBPDB: a database of RNA-binding specificities," Nucleic Acids Research, Jan. 2011, 39:D301-D308.
Spitale et al., "RNA SHAPE analysis in living cells-Supplementary Information," Nature Chemical Biology, Nov. 25, 2012, 18 pages.
Van Nostrand et al., "Robust transcriptome-wide discovery of RNA-binding protein binding sites with enhanced CLIP (eCLIP),—Supplementary Material" Nature Methods, Mar. 28, 2016, 47 pages.
Burmistrz et al., "RNA-Targeting CRISPR-Cas Systems and Their Applications," International Journal of Molecular Sciences, Feb. 7, 2020, 21(3):1122.

\* cited by examiner

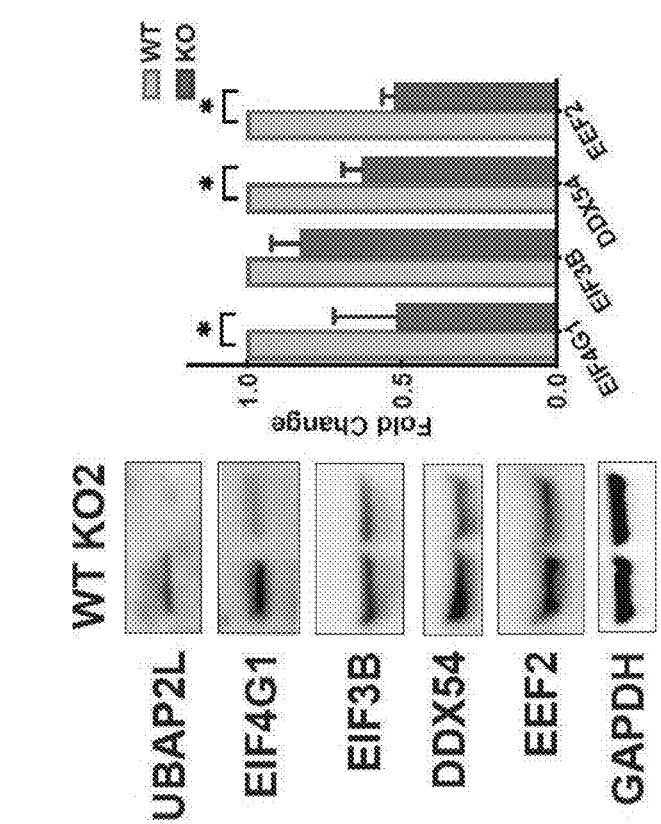
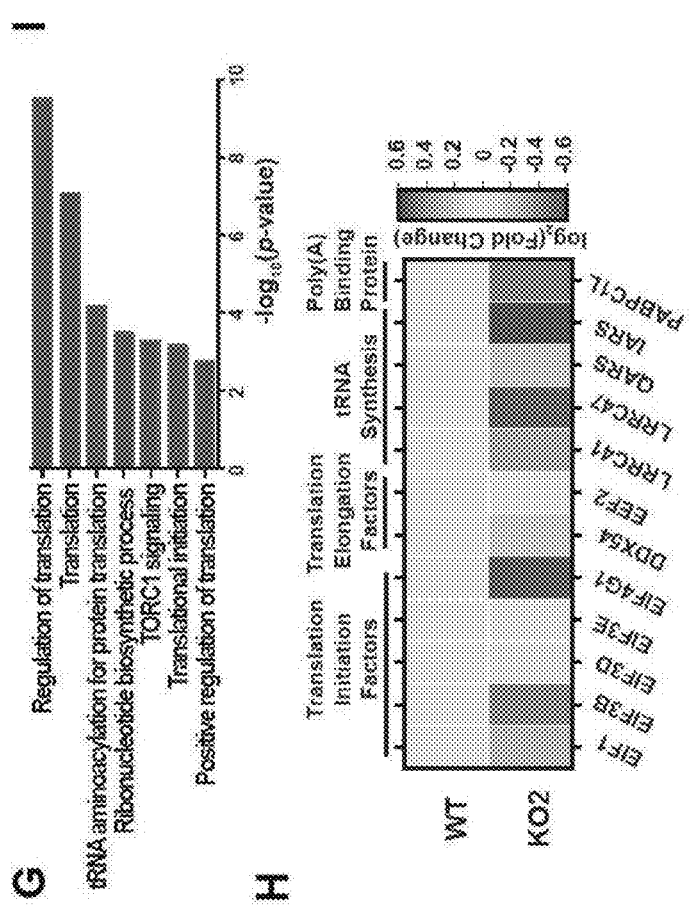
FIG. 4G
FIG. 4H
FIG. 4I

FIG. 9D

| | MEX3C | DDX6 | CNOT7 | PARN |
|---|---|---|---|---|
| Up\|Bound | 701 | 704 | 51 | 114 |
| Down\|Bound | 469 | 483 | 104 | 158 |
| Unchanged\|Bound | 759 | 1454 | 707 | 545 |
| Up\|Not bound | 3897 | 2334 | 777 | 1772 |
| Down\|Not bound | 2139 | 1302 | 1724 | 2587 |
| Unchanged\|Not Bound | 13034 | 14711 | 17625 | 15812 |

FIG. 9E

| | SNRPA | TOB1 | TOB2 | NANOS3 |
|---|---|---|---|---|
| Up\|Bound | 92 | 105 | 56 | 355 |
| Down\|Bound | 267 | 71 | 62 | 212 |
| Unchanged\|Bound | 1438 | 917 | 580 | 2855 |
| Up\|Not bound | 1184 | 969 | 1147 | 858 |
| Down\|Not bound | 1189 | 1139 | 1125 | 929 |
| Unchanged\|Not Bound | 15812 | 17787 | 18018 | 15979 |

FIG. 9F

| | UBAP2L | CLK3 | MTDH | AIMP1 |
|---|---|---|---|---|
| Up\|Bound | 90 | 136 | 6 | 195 |
| Down\|Bound | 519 | 205 | 7 | 144 |
| Unchanged\|Bound | 843 | 2785 | 557 | 593 |
| Up\|Not bound | 1656 | 384 | 66 | 1392 |
| Down\|Not bound | 1910 | 758 | 176 | 2276 |
| Unchanged\|Not Bound | 11923 | 16720 | 20176 | 16389 |

FIG. 9G

| | BOLL | IFIT2 |
|---|---|---|
| Up\|Bound | 949 | 111 |
| Down\|Bound | 363 | 62 |
| Unchanged\|Bound | 7519 | 1715 |
| Up\|Not bound | 136 | 719 |
| Down\|Not bound | 561 | 548 |
| Unchanged\|Not Bound | 11440 | 17833 |

METHODS OF MODULATING RNA TRANSLATION

CROSS-REFERENCE TO RELATED APPLICATIONS

This application claims priority to U.S. Provisional Application Ser. No. 63/106,631, filed on Oct. 28, 2020. The disclosure of the prior application is considered part of the disclosure of this application, and is incorporated herein by reference in its entirety.

BACKGROUND

The fate of the transcriptome determines the status and health of a cell, and RNA-binding proteins (RBPs) control the post-transcriptional processing of these mRNA transcripts. Dysfunction of RBPs is linked to dozens of multisystemic diseases, cancer, and neurological disorders. However, despite their association with disease and although the importance of regulating gene expression at the cytoplasmic stages of an mRNA life cycle is well appreciated, only a small fraction of the over 1,500 RBPs identified thus far have known RNA targets and molecular roles. Rapid, large-scale assignment of molecular functions to more than a thousand uncharacterized and emerging RNA binding proteins (RBPs) is a critical bottleneck to a complete understanding of gene expression regulation.

SUMMARY

The present disclosure is based, at least in part, on modulating RNA translation in a cell.

Provided herein are methods of modulating gene expression of a target RNA in a cell comprising (a) assembling a modulation-unit, wherein the modulation unit comprises an RNA binding protein (RBP), an exogenous RNA binding moiety, and a gene-editing agent; (b) delivering the modulation unit into the cell; and (c) detecting change in the target RNA translation, wherein the modulation unit modulates gene expression of the target RNA in the cell.

In some embodiments, the exogenous RNA binding moiety comprises a MS2 bacteriophage coat protein (MCP). In some embodiments, the gene-editing agent comprises CRISPR components. In some embodiments, the gene-editing agent comprises shRNAs, siRNAs, ASOs, or microRNa mimics.

Methods of Modulating RNA Translation

CROSS-REFERENCE TO RELATED APPLICATIONS

This application claims priority to U.S. Provisional Application Ser. No. 63/106,631, filed on Oct. 28, 2020. The disclosure of the prior application is considered part of the disclosure of this application, and is incorporated herein by reference in its entirety.

BACKGROUND

The fate of the transcriptome determines the status and health of a cell, and RNA-binding proteins (RBPs) control the post-transcriptional processing of these mRNA transcripts. Dysfunction of RBPs is linked to dozens of multisystemic diseases, cancer, and neurological disorders. However, despite their association with disease and although the importance of regulating gene expression at the cytoplasmic stages of an mRNA life cycle is well appreciated, only a small fraction of the over 1,500 RBPs identified thus far have known RNA targets and molecular roles. Rapid, large-scale assignment of molecular functions to more than a thousand uncharacterized and emerging RNA binding proteins (RBPs) is a critical bottleneck to a complete understanding of gene expression regulation.

SUMMARY

The present disclosure is based, at least in part, on modulating RNA translation in a cell.

Provided herein are methods of modulating gene expression of a target RNA in a cell comprising (a) assembling a modulation unit, wherein the modulation unit comprises an RNA binding protein (RBP), an exogenous RNA binding moiety, and a gene-editing agent; (b) delivering the modulation unit into the cell; and (c) detecting change in the target RNA translation, wherein the modulation unit modulates gene expression of the target RNA in the cell.

In some embodiments, the exogenous RNA binding moiety comprises a MS2 bacteriophage coat protein (MCP). In some embodiments, the gene-editing agent comprises CRISPR components. In some embodiments, the gene-editing agent comprises shRNAs, siRNAs, ASOs, or microRNa mimics.

In some embodiments, the delivering step (b) comprises lipofection. In some embodiments, the delivering step (b) comprises a virus-based delivery. In some embodiments, the virus-based delivery comprises adeno-associated virus or lentivirus.

In some embodiments, the detecting step (c) comprises using a reporter mRNA. In some embodiments, the reporter mRNA comprises a luciferase mRNA. In some embodiments, the target RNA is an endogenous mRNA. In some embodiments, the target RNA is a non-coding RNA.

In some embodiments, the RBP is BTG1, CNOT2, CNOT4, CNOT7, CPSF5, DDX6, EWSR1, FUBP1, hnRNPA0, hnRNPC1/2, MEX3C, NANOS1, NANOS2, NOP56, PARN, PRR3, RBM14, RBM7, RPS6, SAMD4A, SNRPA, SRSF11, TOB1, TOB2, UTP11L, YTHDF2, ZC3H18, ZCCHC11, ZFP36, ZFP36L1, ZFP36L2, ABT1, AC004381.6, AIMP1, ALDH18A1, ANXA2, APOBEC3F, ASCC1, ATP5C1, BCCIP, BOLL, BYSL, BZW1, CELF5, CLK1, CLK2, CPSF1, DAZ2, DAZ3, DAZ4, DCN, DDX1, DDX19B, DDX20, DDX39A, DMPK, EEF1A1, EIF3G, ERAL1, XOSC4, FAM46A, FAM98A, FKBP3, FXR2, G3BP2, GLTSCR2, GSPT2, GTF2F1, GTPBP10, HADHB, HDGF, hnRNPE1, HNRPDL, HSPB1, KIAA1324, LARP1, LARP4, LARP4B, LIN28A, LUC7L, MAK16, MATR3, MBNL2, MEPCE, MRPL39, MTDH, NDUFV3, NUFIP2, NUSAP1, PABPC1, PABPC5, PCBP4, PEG10, PPAN, PPIL4, PRPF3, PRPF31, PRRC2B, PTRH1, PUS7, RBM33, RBM38, RBMX2, RPL10A, RPL14, RPL15, RPLPO, RPS20, RPUSD3, RPUSD4, RTN4, SERBP1, SF3A3, SFRS10, SFRS13A, SFRS2IP, SLC7A9, SMN1, SPATS2L, SRSF5, SRSF8, THOC1, TRA2A, TRIM39, TUFM, UBAP2L, UTP23, XPO5, XRN1, YWHAE, or ZRANB2.

In some embodiments, the gene expression of the target RNA is upregulated. In some embodiments, the gene expression of the target RNA is downregulated.

Also provided herein are methods of identifying a function of an RNA binding protein (RBP) comprising (a) contacting the RBP to an exogenous RNA binding moiety; (b) allowing the exogenous RNA binding moiety to interact with an RNA structural motif; and (c) profiling the RBP tethered to the RNA structural motif, thereby identifying a function of the RBP.

In some embodiments, the exogenous RNA binding moiety comprises a MS2 bacteriophage coat protein (MCP). In some embodiments, the RNA structural motif comprises a reporter mRNA. In some embodiments, the reporter mRNA comprises a MS2 genomic RNA stem-loop.

In some embodiments, the profiling comprises transcriptome analysis or gene expression analysis. In some embodiments, the profiling comprises enhanced cross-linking immunoprecipitation (eCLIP).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

(FIG. 2C) DDX6, MEX3C, TOB2, and TOB1, which show read density enrichment in 5'UTRs; and (FIG. 2D) UBAP2L, which shows read density enrichment in CDS.

FIG. 3A shows depletion of DDX6 (left) and overexpression of TOB2 (right). FIG. 3B shows depletion UBAP2L (left), and overexpression of BOLL (right).

FIG. 4A shows Western blots of extracts from control (WT) HEK293T cells and two independent clonal isolates with CRISPR-mediated disruption of UBAP2L. FIG. 4B (Left) representative anti-puromycin western blot of extracts from puromycin-treated WT and KO cells. GAPDH served as loading control. (Right) Densitometric quantitation of blots from of n=3 independent experiments.

FIG. 4D shows scatter plots of log 2-transformed RPKM ratios of polysome transcript levels (y-axis) and input transcript levels (x-axis) between the UBAP2L knockout HEK293T lines and WT samples. The RPKM values from the two replicates were averaged prior to analysis and transcripts with average RPKM≥1 were considered. Numbers and percentages of transcripts in each quadrant are indicated. FIG. 4E shows cumulative distribution plots of log 2-transformed transcript levels (RPKM≥1) in pooled polysome fractions from the two UBAP2L knockout HEK293T lines and WT control, normalized to levels in the respective input lysates. p-values were calculated using a two-sample Kolmogorov-Smirnov test.

FIG. 4G shows gene ontology (GO) analysis for UBAP2L exon target transcripts (n=1,425). Significantly enriched GO terms were determined by Fisher's exact test at a false discovery rate ofp≤0.01. Shown are GO terms that are related to mRNA translation.

FIG. 4H shows a heat map showing log 2-transformed polysome association ratio between UBAP2L knockout lines (KO) and control (WT) for the indicated translation regulators.

FIG. 4I (Left) Representative western blots of UBAP2L, EIF4G1, EIF3B, DDX54, and EEF2 in UBAP2L knockout cells. GAPDH served as a loading control. (Right) Densitometric quantitation of blots from of n=3 independent experiments.

FIG. 4J shows transgene expression constructs. RCas9 is expressed from a tetracycline responsive element (TRE) reporter. A constitutive promoter drives a polycistronic transcript containing puromycin N-acetyl transferase (Puro) and the reverse tetracycline (tet)-controlled transactivator (rtTA) separated by a P2A self-cleaving peptide, as well as CFP fused to a nuclear localization signal (NLS) preceded by an internal ribosome entry site (IRES). A second construct drives rCas9 fused to UBAP2L in same plasmid backbone. rCas9 and rCas9-UBAP2L constructs were integrated into the genome at random copy number to establish stable cell lines. A third reporter construct harbors a U6 promoter driven single guide (sg)RNA targeting the indicated sites in the YFP reporter, which contains of a YFP fused to histone H2B driven by a tet-inducible promoter, and NLS-fused RFP driven by the EF1a promoter. The reporter construct was transiently transfected into rCas9 and rCas9-UBAP2L-expressing lines, and the expression levels of the three reporters were measured by FACS. FIG. 4K shows a bar graph showing mean YFP levels in rCas9-UBAP2L expressing cells, normalized to rCas9 expressing cells, on each targeting site.

(FIG. 5F) Surface view with 60S ribosomal subunits (RNA and protein). (FIG. 5G) View as in (FIG. 5F) with non-highlighted proteins removed. (FIG. 5H) View as in (FIG. 5G) rotated 900 around the z-axis.

(FIG. 8A) Extracts from HEK293T cells or (FIG. 8B) from HEK293T transfected with the indicated MCP-tagged RBP ORFs immunoprecipitated with non-immune (IgG) control antibodies, and western blot analysis using either RBP-specific (FIG. 8A) or anti-V5 (FIG. 8B) antibodies. The molecular weight (in kDa) of standards are indicated on the right. Arrowheads indicate the calculated molecular weight for each RBP or RBP fusion protein.

FIG. 9A shows Western blots, with GAPDH or tubulin serving as loading controls, as indicated. FIG. 9B shows bar graphs indicating RBP transcript levels determined by qRT-PCR, normalized to levels of 18S rRNA.

FIGS. 9D-9G show numbers of up- or downregulated or unchanged genes for transcripts bound or not bound by the indicated RBP, for (FIG. 9D) knockdown and (FIG. 9E) overexpression of destabilizing RBPs and (FIG. 9F) knockdown and (FIG. 9G) overexpression of stabilizing RBPs.

(FIG. 9I) depletion of the stabilizer CLK3 (left), and overexpression of the destabilizer IFIT2 (right).

(FIG. 10J) Plasmid design for RCas9-4EBP1 experiment. (FIG. 10K) Bar graph showing mean YFP levels in rCas9-4EBP1 expressing cells, normalized to rCas9 expressing cells, on each targeting site.

(FIG. 11D) ES15L (FIG. 11E) ES7S, (FIG. 11F) ES27L, and (FIG. 11G) ES31L.

DETAILED DESCRIPTION

Figure 1B:
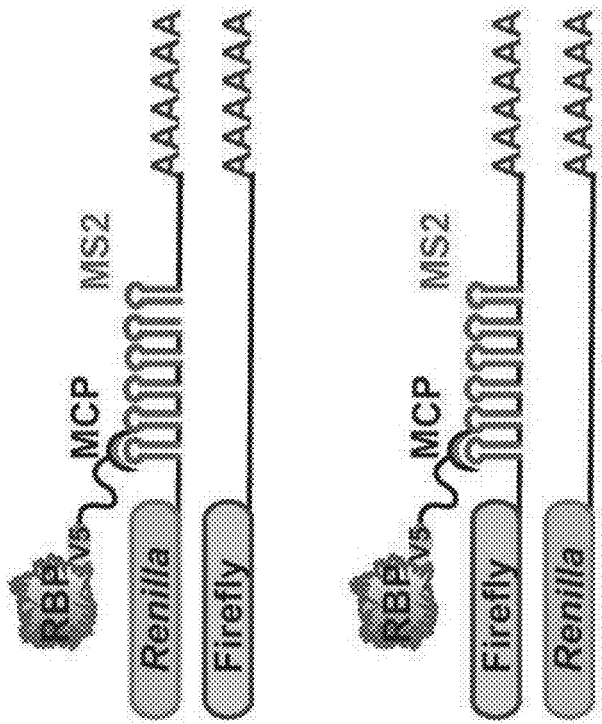
FIG. 1B shows an exemplary schematic of luciferase reporters. The coding region for either firefly (top) or Renilla (bottom) luciferase contain 6 MS2 stem-loop structures in the 3'UTR. The complementary reporters lacking MS2 hairpins were used as internal controls to normalize reporter signals. RBPs fused C-terminally to the MS2 coat protein (MCP), which recognizes MS2 hairpins with high affinity, are co-expressed with the reporters in a HeLa cell line.

Detailed herein are methods of modulating gene expression of a target RNA in a cell and methods of identifying a function of an RNA binding protein (RBP). In some embodiments, a method of modulating gene expression of a target RNA in a cell can include (a) assembling a modulation unit, wherein the modulation unit comprises an RNA binding protein (RBP), an exogenous RNA binding moiety, and a gene-editing agent; (b) delivering the modulation unit into the cell; and (c) detecting change in the target RNA translation, wherein the modulation unit modulates gene expression of the target RNA in the cell.

In some embodiments, a method of identifying a function of an RNA binding protein (RBP) can include (a) contacting the RBP to an exogenous RNA binding moiety; (b) allowing the exogenous RNA binding moiety to interact with an RNA structural motif; and (c) profiling the RBP tethered to the RNA structural motif, thereby identifying a function of the RBP.

Various non-limiting aspects of these methods are described herein, and can be used in any combination without limitation. Additional aspects of various components of methods for modulating gene expression of a target RNA, or identifying a function of an RNA binding protein are known in the art.

It must be noted that, as used in the specification and the appended claims, the singular forms "a," "an" and "the" include plural referents unless the context clearly dictates otherwise.

As used herein, "biological sample" can refer to a sample generally including cells and/or other biological material. A biological sample can be obtained from a mammalian organism. For example, a biological sample can be obtained from a human. A biological sample can be obtained from a non-human mammal (e.g., a dog, a cat, a monkey, a mouse, or a rat). A biological sample can be obtained from non-mammalian organisms (e.g., a plants, an insect, an arachnid, a nematode), a fungi, an amphibian, or a fish (e.g., zebrafish). A biological sample can be obtained from a prokaryote such as a bacterium, e.g., *Escherichia coli*, Staphylococci or *Mycoplasma pneumoniae*; an archaea; a virus such as Hepatitis C virus or human immunodeficiency virus; or a viroid. A biological sample can be obtained from a eukaryote, such as a patient derived organoid (PDO) or patient derived xenograft (PDX). Biological samples can be derived from a homogeneous culture or population of organisms or alternatively from a collection of several different organisms, for example, in a community or ecosystem.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

In some embodiments, the biological sample can be a tissue sample. In some embodiments, the tissue sample can include live cells from a cell culture. In some embodiments, the tissue sample can be a fresh, frozen tissue sample. In some embodiments, the fresh, frozen tissue sample is cryoground into powder. In some embodiments, the biological sample can be live cells on standard tissue culture dishes. In some embodiments, the biological sample can be flash, frozen tissues that have been cryoground into powder and placed on tissue culture dishes, pre-chilled on dry ice.

As used herein, a "cell" can refer to either a prokaryotic or eukaryotic cell, optionally obtained from a subject or a commercially available source.

As used herein, "delivering", "gene delivery", "gene transfer", "transducing" can refer to the introduction of an exogenous polynucleotide into a host cell, irrespective of the method used for the introduction. Such methods include a variety of well-known techniques such as vector-mediated gene transfer (e.g., viral infection/transfection, or various other protein-based or lipid-based gene delivery complexes) as well as techniques facilitating the delivery of "naked" polynucleotides (e.g., electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome.

In some embodiments, a polynucleotide can be inserted into a host cell by a gene delivery molecule. Examples of gene delivery molecules can include, but are not limited to, liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

As used herein, "detecting" can refer to a method used to discover, determine, or confirm the existence or presence of a compound and/or substance (e.g., DNA, RNA, a protein). In some embodiments, a detecting method can be used to detect a protein. In some embodiments, a detecting method can be used to detect an RNA binding protein bound to an RNA fragment. In some embodiments, detecting can include chemiluminescence or fluorescence techniques. In some embodiments, detecting can include immunological-based methods (e.g., quantitative enzyme-linked immunosorbent assays (ELISA), Western blotting, or dot blotting) wherein antibodies are used to react specifically with entire proteins or specific epitopes of a protein. In some embodiments, detecting can include immunoprecipitation of the protein.

As used herein, the term "expression" refers to the process by which polynucleotides are transcribed into mRNA and/or the process by which the transcribed mRNA is subsequently translated into peptides, polypeptides, or proteins. In some embodiments, if the polynucleotide is derived from genomic DNA, expression may include splicing of the mRNA in a eukaryotic cell. The expression level of a gene may be determined by measuring the amount of mRNA or protein in a cell or tissue sample; further, the expression level of multiple genes can be determined to establish an expression profile for a particular sample.

As used herein, "modulating" can refer to modifying, regulating, or altering the endogenous gene expression in a cell. In some embodiments, modulating gene expression can include systematically influencing RNA stability and/or translation by activating or suppressing the gene expression. In some embodiments, modulation of gene expression can include stabilizing a target RNA. In some embodiments, stabilizing a target RNA can increase translation of the target RNA. In some embodiments, modulation of gene expression can include destabilizing a target RNA. In some embodiments, destabilizing a target RNA can suppress translation of the target RNA. In some embodiments, modulation of gene expression can include increasing translation of a target RNA. In some embodiments, modulation of gene expression can include suppressing translation of a target RNA. In some embodiments, the gene expression of the target RNA is upregulated. In some embodiments, the gene expression of the target RNA is downregulated.

As used herein, "nucleic acid" is used to include any compound and/or substance that comprise a polymer of nucleotides. In some embodiments, a polymer of nucleotides are referred to as polynucleotides. Exemplary nucleic acids or polynucleotides can include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A deoxyribonucleic acid (DNA) can have one or more bases selected from the group consisting of adenine (A), thymine (T), cytosine (C), or guanine (G), and a ribonucleic acid (RNA) can have one or more bases selected from the group consisting of uracil (U), adenine (A), cytosine (C), or guanine (G).

In some embodiments, the nucleic acid is a messenger RNA (mRNA). As used herein, "messenger RNA" (mRNA) can refer to any polynucleotide which encodes a polypeptide of interest and which is capable of being translated to produce the encoded polypeptide of interest in vitro, in vivo, in situ, or ex vivo.

Methods of Modulating Gene Expression of a Target RNA

Provided herein are methods of modulating gene expression of a target RNA in a cell including (a) assembling a modulation unit, wherein the modulation unit comprises an RNA binding protein (RBP), an exogenous RNA binding moiety, and a gene-editing agent; (b) delivering the modulation unit into the cell; and (c) detecting change in the target RNA translation, wherein the modulation unit modulates gene expression of the target RNA in the cell. In some embodiments, a target RNA is an endogenous mRNA. In some embodiments, a target RNA is a non-coding RNA.

In some embodiments, a modulation unit can include an RNA binding protein (RBP), an exogenous RNA binding moiety, and a gene-editing agent. In some embodiments, the exogenous RNA binding moiety comprises a MS2 bacteriophage coat protein (MCP). In some embodiments, the gene-editing agent comprises CRISPR components. In some embodiments, the gene-editing agent comprises shRNAs, siRNAs, ASOs, or microRNa mimics.

RNA Binding Protein

RNA binding proteins (RBPs) are proteins that bind to the double or single stranded RNA in cells and have important roles in cellular processes (e.g., cellular transport, or localization). RBPs also play a role in post-transcriptional control of RNAs, such as RNA splicing, polyadenylation, mRNA stabilization, mRNA localization, and translation. In some embodiments, an RBP is a cytoplasmic protein. The term "RNA binding protein" can refer to a protein that interacts with RNA molecules (e.g., mRNA) from synthesis to decay to affect their metabolism, localization, stability, and translation. In some embodiments, an RBP is a nuclear protein. In some embodiments, RBPs can include, but are not limited to, splicing factors, RNA stability factors, histone stem-loop binding proteins, or ribosomes. For example, a eukaryotic ribosome can include a collection of RBPs that can interact directly with mRNA coding sequences. In some embodiments, an RBP is a cytoplasmic protein.

In some embodiments, an RNA binding protein comprises a ribosomal protein, wherein the ribosomal protein binds to a ribosome and an mRNA during translation. In some embodiments, an RNA binding protein comprises a ribosomal protein, wherein the ribosomal protein binds to a ribosome or an mRNA during translation. In some embodiments, the RNA binding protein comprises at least one of: SLTM, ZGPAT, PPARGC1B, PELP1, DCP2, CSTF3, TRA2B, ZNF638, SRSF9, LUC7L2, PTBP3, SF3B3, VCP, HNRNPA2B1, PTBP1, PCBP2, LSM14A, LSM12, DHX15, DDX27, DDX17, DDX21, IPO5, RPL22L1, RPL35, RPSA, MRPS34, NIFK, THUMPD1, RPUSD3, RRBP1, EEFSEC, UBAP2L, PUS7L, EIF4ENIF1, BICC1, EIF4E2, DARS2, TRDMT1, UPF3B, ZFP36L2, YTHDF2, EDC3, HNRNPR, UPF3A, ELAVL1, RBM27, XRN1, FUS, EXOSC7, PSPC1, CNOT7, CNOT6, CNOT4, CNOT3, AGO2, ENDOU, RBFOX1 (A2BP1), RBFOX2 (RBM9), RBFOX3 (NeuN), SLBP, RBM5, RBM6, PRBP1, ACO1, Adatl, PCBP1, PCBP3, PCBP4, RBM3, RBM4, APOBECI, BTG1, CNOT2, CPSF5, DDX6, EWSR1, FUBP1, hnRNPA0, hnRNPC1/2, MEX3C, NANOS1, NANOS2, NOP56, PARN, PRR3, RBM14, RBM7, RPS6, SAMD4A, SNRPA, SRSF11, TOB1, TOB2, UTP11L, ZC3H18, ZCCHC11, ZFP36, ZFP36L1, ABT1, AC004381.6, AIMP1, ALDH18A1, ANXA2, APOBEC3F, ASCC1, ATP5C1, BCCIP, BOLL, BYSL, BZW1, CELF5, CLK1, CLK2, CPSF1, DAZ2, DAZ3, DAZ4, DCN, DDX1, DDX19B, DDX20, DDX39A, DMPK, EEF1A1, EIF3G, ERAL1, XOSC4, FAM46A, FAM98A, FKBP3, FXR2, G3BP2, GLTSCR2, GSPT2, GTF2F1, GTPBP10, HADHB, HDGF, hnRNPE1, HNRPDL, HSPB1, KIAA1324, LARP1, LARP4, LARP4B, LIN28A, LUC7L, MAK16, MATR3, MBNL2, MEPCE, MRPL39, MTDH, NDUFV3, NUFIP2, NUSAP1, PABPC1, PABPC5, PCBP4, PEG10, PPAN, PPIL4, PRPF3, PRPF31, PRRC2B, PTRH1, PUS7, RBM33, RBM38, RBMX2, RPL10A, RPL14, RPL15, RPLPO, RPS20, RPUSD3, RPUSD4, RTN4, SERBP1, SF3A3, SFRS10, SFRS13A, SFRS2IP, SLC7A9, SMN1, SPATS2L, SRSF5, SRSF8, THOC1, TRA2A, TRIM39, TUFM, UBAP2L, UTP23, XPO5, XRN1, YWHAE, or ZRANB2.

RNA-binding proteins (RBPs) have roles in controlling the fate of RNAs including the modulation of pre-mRNA splicing, RNA modification, translation, stability and localization. RBPs are a group of proteins that interact with RNA using an array of strategies from well-defined RNA-binding domains to disordered regions that recognize RNA sequence and/or secondary structures.

As used herein, "RNA-RBP complex" can refer to a ribonucleoprotein complex comprising an RNA-binding protein (RBP) bound to a double or single stranded RNA in a cell. In some embodiments, the RNA-RBP complex can include an RNA fragment bound by an RNA binding protein. In some embodiments, the RBP is crosslinked to an RNA in a biological sample. In some embodiments, the crosslinking can include UV crosslinking. In some embodiments, the RBP is covalently linked to the RNA in a biological sample. In some embodiments, crosslinking can be performed by any method including, but not limited to, thermal crosslinking, chemical crosslinking, physical crosslinking, ionic crosslinking, photo-crosslinking, free-radical initiation crosslinking, an addition reaction, condensation reaction, water-soluble crosslinking reactions, irradiative crosslinking (e.g., x-ray, electron beam), or combinations thereof.

As used herein, "ribosomal protein" can refer to a protein that is present in a ribosome (e.g., a mammalian ribosome) or a protein that binds to a ribosome and an mRNA during translation (e.g., a translation initiation factor, a translation elongation factor, and a translation termination factor). The eukaryotic ribosome is composed of 79 ribosomal proteins, large ribosomal proteins (RPLs) and small subunit proteins (RPSs) that interweave with 4 highly structured RNAs (5S, 5.8S, 18S, and 28S rRNAs) to form the final translation-capable ribonucleoprotein. Thus, quantification of ribosome-associated RNA is highly similar to profiling of RNAs associated with other RNA binding proteins.

In some embodiments, the ribosomal protein binds to a ribosome or an mRNA during translation. The term "translation initiation factor" can refer to a protein that binds to a ribosome, a subunit of a ribosome, and/or an mRNA during the start of translation of an mRNA. The term "translation elongation factor" can refer to a protein that binds to a ribosome, a subunit of a ribosome, and/or mRNA during translation of an mRNA. The term "translation termination factor" can refer to a protein that binds to a ribosome, a subunit or a ribosome, and/or mRNA during cessation of translation and/or release of an mRNA from a ribosome or a subunit of a ribosome. In a ribosome, ribosomal proteins can participate in the translation process and binding of translation factors (e.g., translation initiation factor, translation elongation factor, translation termination factor). In some embodiments, the ribosomal protein is selected from the group consisting of: RPS2, RPS3, RPS3A, RPS4X, RPS4Y1, RPS4Y2, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS28, RPS29, RPS30, RSSA, 20. RACK1, RPL3, RPL4, RPL5, RPL6, RPL7A, RPL7, RPL8, RPL9, RPL10A, RPL10, RPL11, RPL12, RPL13A, RPL13, RPL14, RPL15, RPL17, RPL18A, RPL18, RPL19, RPL21, RPL22, RPL23A, RPL23, RPL24, RPL26, RPL27A, RPL27, RPL28, RPL29, RPL30, RPL31, RPL32, RPL34, RPL35A, RPL35, RPL36, RPL37A, RPL37, RPL38, RPL39, RPL40, RPL41, RPLA0, RPLA1, and RPLA2. In some embodiments, the ribosomal protein is a translation initiation factor. In some embodiments, the ribosomal protein is a translation elongation factor. In some embodiments, wherein the ribosomal protein is a translation termination factor.

Exogenous RNA Binding Moiety and Gene-Editing Agent

As used herein, the term "exogenous RNA binding moiety" refers to a molecule or moiety capable of binding to an RNA (e.g., target RNA). In some embodiments, an exogenous RNA binding moiety can be fused to a protein (e.g., RNA binding protein). In some embodiments, an exogenous RNA binding moiety can include a reporter mRNA. In some embodiments, the exogenous RNA binding moiety can be attached to a protein through an artificial RNA-protein interaction. In some embodiments, an exogenous RNA binding moiety can include a MS2 bacteriophage coat protein (MCP). In some embodiments, an exogenous RNA binding moiety can be fused to an RNA binding protein (RBP).

As used herein, the term "gene-editing agent" can refer to an agent that allows for changing the DNA or RNA (e.g., mRNA) in the genome. In some embodiments, gene-editing can include insertion, deletion, modification, or replacement of the DNA or RNA. In some embodiments, a gene-editing agent can include a nuclease-based gene editing platform. In some embodiments, a gene-editing agent can include zinc finger nucleases (ZFNs), transcription activator-like effector nucleases (TALENs), engineered meganucleases, or a clustered regularly interspaced short palindromic repeats (CRISPR) system. In some embodiments, a gene-editing agent can include RNA interference (e.g., short hairpin RNA (shRNA), small interfering RNA (siRNA), antisense oligonucleotide (ASO), or microRNA mimics). In some embodiments, the gene-editing agent can include CRISPR components. For example, in some embodiments, CRISPR components can include, but are not limited to, a guide RNA and a CRISPR-associated endonuclease (Cas protein). In some embodiments, the gene-editing agent can include a guide RNA (e.g., gRNA or sgRNA) and a CRISPR-associated endonuclease (Cas protein). In some embodiments, the gene-editing agent comprises shRNAs, siRNAs, ASOs, or microRNa mimics.

As used herein, the term "CRISPR" refers to a technique of sequence specific genetic manipulation relying on the clustered regularly interspaced short palindromic repeats pathway, which unlike RNA interference regulates gene expression at a transcriptional level. The term "gRNA" or "guide RNA" refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7 and Graham, D., et al. Genome Biol. 2015; 16: 260. The term "Single guide RNA" or "sgRNA" is a specific type of gRNA that combines tracrRNA (transactivating RNA), which binds to Cas9 to activate the complex to create the necessary strand breaks, and crRNA (CRISPR RNA), comprising complimentary nucleotides to the tracrRNA, into a single RNA construct. Exemplary methods of employing the CRISPR technique are described in WO 2017/091630, which is incorporated by reference in its entirety.

In some embodiments, the single guide RNA can recognize a target RNA, for example, by hybridizing to the target RNA. In some embodiments, the single guide RNA comprises a sequence that is complementary to the target RNA. In some embodiments, the sgRNA can include one or more modified nucleotides. In some embodiments, the sgRNA has a length that is about 10 nt (e.g., about 20 nt, about 30 nt, about 40 nt, about 50 nt, about 60 nt, about 70 nt, about 80 nt, about 90 nt, about 100 nt, about 120 nt, about 140 nt, about 160 nt, about 180 nt, about 200 nt, about 300 nt, about 400 nt, about 500 nt, about 600 nt, about 700 nt, about 800 nt, about 900 nt, about 1000 nt, or about 2000 nt).

In some embodiments, a single guide RNA can recognize a variety of RNA targets. For example, a target RNA can be messenger RNA (mRNA), ribosomal RNA (rRNA), signal recognition particle RNA (SRP RNA), transfer RNA (tRNA), small nuclear RNA (snRNA), small nucleolar RNA (snoRNA), antisense RNA (aRNA), long noncoding RNA (lncRNA), microRNA (miRNA), piwi-interacting RNA (piRNA), small interfering RNA (siRNA), short hairpin RNA (shRNA), retrotransposon RNA, viral genome RNA, or viral noncoding RNA. In some embodiments, a target RNA can be an RNA involved in pathogenesis of conditions such as cancers, neurodegeneration, cutaneous conditions, endocrine conditions, intestinal diseases, infectious conditions, neurological conditions, liver diseases, heart disorders, or autoimmune diseases. In some embodiments, a target RNA can be a therapeutic target for conditions such as cancers, neurodegeneration, cutaneous conditions, endocrine conditions, intestinal diseases, infectious conditions, neurological conditions, liver diseases, heart disorders, or autoimmune diseases.

In some embodiments, a method described herein can include assembling a modulation unit, wherein the modulation unit comprises an RNA binding protein (RBP), an exogenous RNA binding moiety, and a gene-editing agent. In some embodiments, the assembling of the modulation unit can be performed outside of a host cell. In some embodiments, the assembling can include plasmid construction.

In some embodiments, a method described herein can include delivering a modulation unit into a cell. In some embodiments, the delivering step comprises lipofection. In some embodiments, the delivering step comprises a virus-based delivery. In some embodiments, the virus-based delivery comprises adeno-associated virus or lentivirus.

In some embodiments, a method described herein can also include detecting change in a target RNA stability and/or translation, wherein a modulation unit modulates gene expression of the target RNA in a cell. As used herein, a "reporter mRNA" can refer to an mRNA that can be attached to another gene of interest, wherein the reporter mRNA can express a protein that is easily measured and identified and can be used as a marker to indicate whether the gene of interest in expressed in a cell or organism. In some embodiments, the detecting step comprises using a reporter mRNA. In some embodiments, a reporter mRNA can include a luciferase mRNA. In some embodiments, a reporter mRNA can include chloramphenicol acetyltransferase, β-galactosidase (GAL), β-glucuronidase, β-glucuronidase, firefly luciferase, Renilla luciferase, or green fluorescent protein (GFP).

Methods of Identifying a Function of an RNA Binding Protein (RBP)

Provided herein are methods of identifying a function of an RNA binding protein (RBP) including (a) contacting the RBP to an exogenous RNA binding moiety; (b) allowing the exogenous RNA binding moiety to interact with an RNA structural motif; and (c) profiling the RBP tethered to the RNA structural motif, thereby identifying a function of the RBP.

In some embodiments, a function of an RNA binding protein can include regulating target RNA translation and/or stability. In some embodiments, a function of an RNA binding protein can include controlling global protein homeostasis by affecting levels of RNA translation regulators. In some embodiments, a function of an RNA binding protein can include RNA splicing, modulating RNA stability, RNA transport, or RNA translation. In some embodiments, a function of an RNA binding protein can include stabilizing a target RNA. In some embodiments, a function of an RNA binding protein can include destabilizing a target RNA. In some embodiments, a function of an RNA binding protein can include enhancing translation of a target RNA. In some embodiments, a function of an RNA binding protein can include suppressing translation of a target RNA.

In some embodiments, the contacting step can include an exogenous RNA binding moiety being fused to a RNA binding protein. In some embodiments, the exogenous RNA binding moiety can be fused to a RNA binding protein through an artificial RNA-protein interaction. In some embodiments, an exogenous RNA binding moiety can include a reporter mRNA. In some embodiments, an exogenous RNA binding moiety comprises a MS2 bacteriophage coat protein (MCP). In some embodiments, an RNA structural motif comprises a reporter mRNA. In some embodiments, the reporter mRNA comprises a MS2 genomic RNA stem-loop. As used herein, an "RNA structural motif" can refer to a collection of residues that fold into a stable three-dimensional (3D) structure of an RNA molecule. In some embodiments, an RNA structural motif can include an RNA hairpin loop, RNA internal loop, a tetraloop, a sarcin-ricin loop, or a T-loop. In some embodiments, an RNA structural motif can includes a MS2 genomic RNA stem-loop.

As used herein, "profiling" can refer to the measurement of an activity (e.g., expression) of one or more genes, to create a global picture of cellular function. In some embodiments, the profiling comprises transcriptome analysis or gene expression analysis. In some embodiments, the profiling comprises enhanced cross-linking immunoprecipitation (eCLIP). As used herein, "Enhanced crosslinking and immunoprecipitation (eCLIP)" refers to a method to profile RNAs bound by an RNA binding protein of interest. In some embodiments, eCLIP can be modified and used to profile RNAs bound by specific ribosomal subunit proteins. In some embodiments, enhanced crosslinking and immunoprecipitation (eCLIP) recovers protein-coding mRNAs (with a particular enrichment for coding sequence regions).

EXAMPLES

The disclosure is further described in the following examples, which do not limit the scope of the disclosure.

Figures 7A, 7B, 7C:
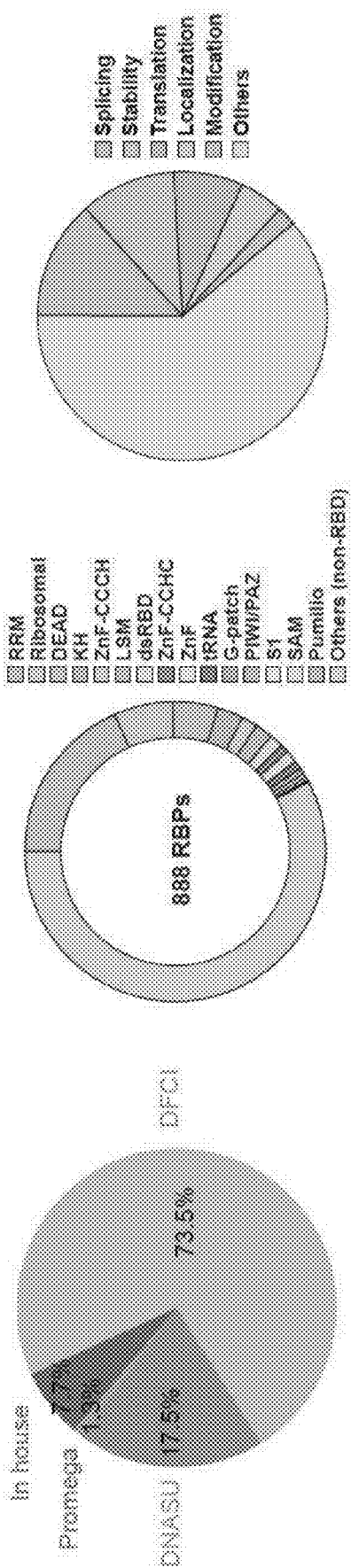
FIG. 7A shows sources of RBP open reading frames (ORFs). The collection of 1062 ORFs for 888 RBPs were acquired from the Dana-Farber Cancer Institute (73.5%), DNASU Plasmid repository (17.5%), in-house cloning efforts (7.7%) and Promega (1.3%).
FIG. 7B shows distribution of known classical and non-classical RNA-binding domains in the RBP library.
FIG. 7C shows a summary of molecular categories for RNA-related functions of the RBP library.

Example 1—Generation of Resource of RBP Open-Reading Frames Fused to MS2 Coat Protein and Tethered Function Assays A collection of RBP expression constructs was assembled using in-house bioinformatics tools to extract genes annotated to contain RNA-binding domains as predicted by PFAM and PRINTS. This set was extended with mRNA-bound putative RBPs identified experimentally in two different studies which used UV-cross-linking and oligo(dT) capture followed by mass spectrometry. 888 unique RBPs with 1,062 RBP ORFs (FIG. 1A) were acquired from both commercial sources and through in-house cloning efforts (FIG. 7A; Table 1) and sub-cloned into two constructs using Gateway-mediated cloning: one that directs expression of the RBPs as fusion proteins with the V5 epitope tag C-terminally appended, and one with an additional bacteriophage MS2 coat protein (MCP) domain at the C-terminus. Overall, ~40% of the 69 RBPs in the collection contain known canonical RNA-binding motifs, while the remainder may associate with RNA through other interaction domains or binding modes (FIG. 7B). Highlighting the need for assessing the roles of RBPs in RNA metabolism, Gene Ontology (GO) analysis showed that ~60% of the RBPs in the collection have no known RNA-related functions (FIG. 7C). Thus, a comprehensive resource of representative 'tethered' and 'untethered' RBP expression libraries was assembled comprising the majority of all predicted and/or experimentally identified RBPs.

Figure 1A:
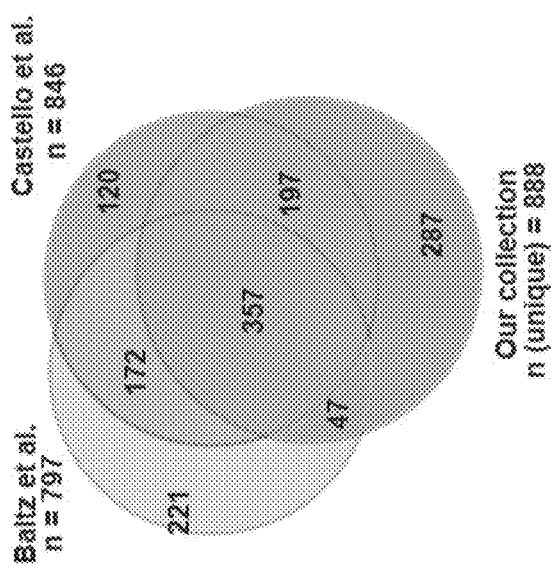
FIG. 1A shows a collection of 1,062 open reading frames (ORFs) for 888 unique RBPs and their overlap with those identified experimentally by Baltz et al. (Baltz et al., 2012) and Castello et al. (Castello et al., 2012).
Figure 1C:
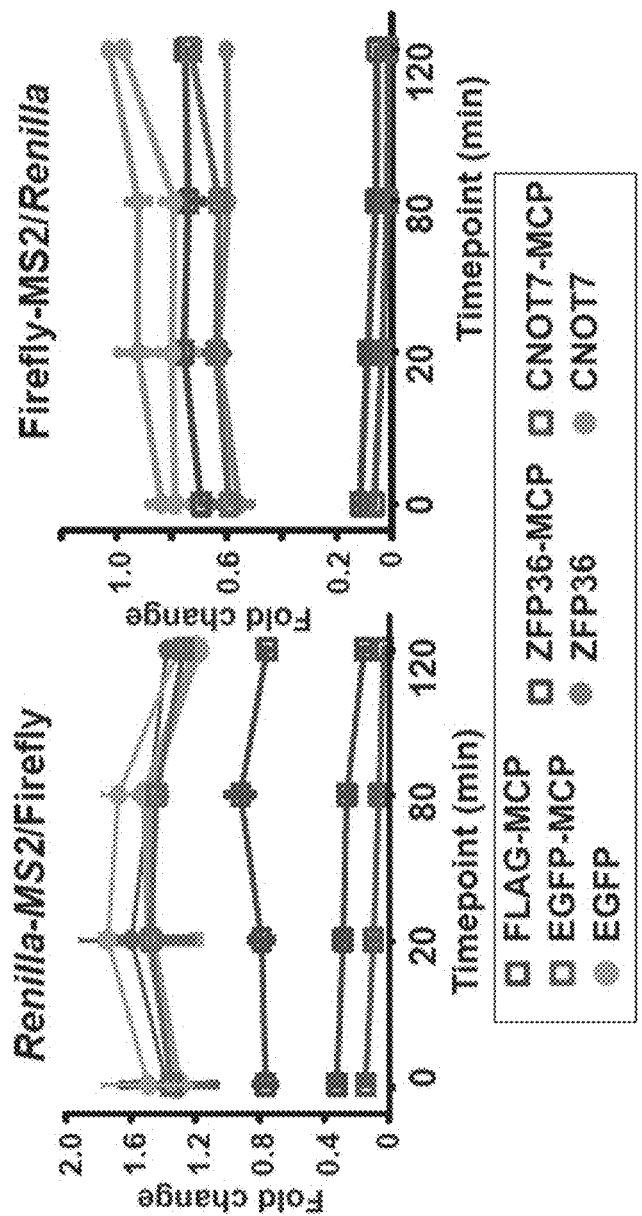
FIG. 1C shows time-course analysis of the activity of the luciferase reporters in the presence of co-expressed known negative regulators of RNA stability (CNOT7 and ZFP36) or negative controls (EGFP and the FLAG peptide), with ('-MCP') or without MCP fusion. Values are expressed as ratio of the median luciferase activity of MS2-tagged over untagged reporters in the presence of the indicated RBPs, relative to that of the ratio of MS2-tagged over untagged FLAG controls at timepoint 0. Left and right panels in FIG. 1C correspond to top and bottom reporter pairs in FIG. 1B, respectively.

Next, a set of tetracycline-repressible luciferase reporter plasmids were constructed that measure the effect of RBP recruitment to the 3'UTR on reporter expression. F-Luc-6MS2 encodes firefly luciferase followed by 6 MS2 hairpin sequences inserted into the 3'UTR context of HBB (β-globin). To address potential reporter context dependencies, a corresponding Renilla luciferase construct was also generated. Matched constructs lacking MS2 sequences served as negative controls (FIG. 1B). To validate the system, each reporter was co-introduced into HeLa cells along with constructs expressing MCP-fused and unfused versions of ZFP36 (also known as Tristetraprolin, TTP), an RBP activator of AU-rich element (ARE)-mediated RNA decay, enhanced GFP (EGFP) or the FLAG peptide. As expected, ZFP36 but not enhanced GFP (EGFP) or the FLAG peptide, dramatically reduced protein levels of the luciferase reporter in a manner that depended on the presence of the tether but not the identity of the luciferase protein (FIG. 1C). This demonstrated that tethered ZFP36 can recruit functional CCR4-NOT deadenylase complexes, which contain the CafI subunit CNOT7 (an RNase), to the reporter. Tethering of CNOT7 itself recapitulated this finding, indicating that productive recruitment is not limited to sequence-specific RBPs (such as ZFP36), but extends to effector RBPs (such as CNOT7) (FIG. 1C).

TABLE 1

| Gene symbol | Accession number | MW (kDa) | GO Term | Group | Domain | Source |
| --- | --- | --- | --- | --- | --- | --- |
| A1CF | BC054873.1 | 13.8 | Modification | | RRM | DFCI |
| ABT1 | BC048812.1 | 31.1 | Other | Baltz/Castello | RRM | DFCI |
| ABT1 | BC066313.1 | 31.1 | Other | Baltz/Castello | RRM | DFCI |
| ACAA2 | BC001918.1 | 41.9 | Other | | Other | DFCI |
| ACOT9 | | 48.9 | Other | | Other | In-house |
| ACTN4 | BC005033.1 | 104.9 | Other | Castesllo | Other | DFCI |
| ADAD1 | BC040229 | 62.8 | Other | | dsRBD | In-house |
| ADAD2 | BC033491.1 | 61.8 | Other | | dsRBD | DFCI |
| ADAR | BC038227 | 136.0 | Modification | Baltz/Castello | dsRBD | DNASU |
| ADARB1 | BC065545.1 | 76.6 | Modification | Baltz | dsRBD | DFCI |
| ADD1 | BC013393 | 44.0 | Other | | Other | DNASU |
| ADK | BC003568.1 | 38.7 | Other | Castello | Other | DFCI |
| AGGF1 | BC002828.2 | 12.5 | Other | | Other | DFCI |
| AGGF1 | BC032844.1 | 80.9 | Other | | Other | DFCI |
| AHNAK | BC012477.1 | 16.1 | Other | Castello | Other | DFCI |
| AHNAK | BC000926.1 | 16.2 | Other | Castello | Other | DFCI |
| AIMP1 | BC014051.2 | 34.4 | Translation | | tRNA | DFCI |
| AK8 | BC034776.1, BC050576.1 | 54.9 | Other | | Ostler | DFCI |
| ALDH18A1 | HQ268499 | 87.3 | Other | Castello | Other | DNASU |
| ALDH6A1 | BC004909.1, BC032371.1 | 57.8 | Other | Castello | Other | DFCI |
| ANKHD1 | BC040231.1 | 91.5 | Other | Baltz/Castello | KH | DFCI |
| ANKHD1 | BC004457 | 46.1 | Other | Baltz/Castello | KH | In-house |
| ANXA2 | BC052567.1 | 38.6 | Other | Castello | Other | DFCI |
| ANXA2 | BC009564.1 | 38.6 | Other | Castello | Other | DFCI |
| ANXA2 | BC023990.1 | 38.6 | Other | Castello | Other | DFCI |
| APEH | BC000362.2 | 81.2 | Other | Castello | Other | DFCI |
| APOBEC3A | BC126416.1 | 23.0 | Other | | Other | DFCI |
| APOBEC3B | BC053859.1 | 29.8 | Other | Baltz | Other | DFCI |
| APOBEC3C | BC011739.2 | 22.8 | Other | Baltz/Castello | Other | DFCI |
| APOBEC3B | BC017022.1 | 46.6 | Other | | Other | DFCI |
| APOBEC3F | BC038808.1 | 45.0 | Other | Baltz | Other | DFCI |
| APOBEC3F | BC061914 | 9.4 | Other | Baltz | Other | In-house |
| APOBEC3G | BC024268.1 | 46.4 | Other | | Other | DFCI |
| APOBEC3H | BC069023.1 | 21.5 | Other | | Other | DFCI |
| APOBEC4 | BC021711 | 41.6 | Other | | Other | In-house |
| ARL6IP4 | uc004dat.1 | 24.0 | Splicing | Baltz/Castello | Other | DFCI |
| ARL6IP4 | BC001958.1 | 24.6 | Splicing | Baltz/Castello | Other | DFCI |
| ASCC1 | BC012291.1 | 41.2 | Other | | KH | DFCI |
| ASCC3 | BC050681.1 | 13.0 | Other | Baltz | Other | DFCI |
| ASS1 | BC021676.1 | 46.5 | Other | Castello | Other | DFCI |
| ASS1 | BC009243.2 | 46.5 | Other | Castello | Other | DFCI |
| ATP5C1 | BC000470.2, BC000931.3 | 33.0 | Other | Castello | Other | DFCI |
| ATF5C1 | BC016812.1 | 33.0 | Other | Castello | Other | DFCI |
| ATXN1 | BC117125 | 86.9 | Localization | | Other | In-house |
| BCCIP | BC009771.1 | 36.1 | Other | Castello | Other | DFCI |
| BCDIN3D | BC053560.1 | 33.2 | Modification | | Other | DFCI |
| BCL7B | BC000956 | 22.2 | Other | | Other | In-house |
| BMS1 | BC043345.1 | 145.8 | Other | Baltz/Castello | Other | DFCI |
| BOLL | BC033874.1 | 31.3 | Translation | | RRM | DFCI |
| BST2 | BC033873.1 | 19.8 | Other | Castello | Other | DFCI |
| BTG1 | BC016759 | 19.2 | Other | | Other | DNASU |
| BTG2 | BC105949 | 17.4 | Other | | Other | DNASU |
| BTG3 | BC011957.1 | 34.2 | Other | | Other | DNASU |
| BTG4 | BC031045 | 24.0 | Other | | Other | DNASU |
| BTN3A3 | BC015815.2 | 65.0 | Other | | Other | DFCI |
| BUD13 | BC006350.2 | 70.5 | Localization | Castello | Other | DFCI |
| BYSL | BC007340.2 | 37.1 | Other | Castello | Other | DFCI |
| BZW1 | BC026303.1 | 48.0 | Other | Castello | Other | DFCI |
| C16ORF88 | BC117562.1 | 51.6 | Other | Castello | Other | DFCI |
| C1D | BC005235.1 | 16.0 | Other | | Other | DFCI |
| C1D | BC009584.1, BC0095891, BC016284.2 | 16.0 | Other | | Other | DFCI |
| C1ORF131 | BC036800.1 | 31.4 | Other | Baltz/Castello | Other | DFCI |
| C1ORF35 | BC002843.2 | 29.4 | Other | Baltz/Castello | Other | DFCI |
| C9ORF72 | C9ORF72 | 54.3 | Other | | Other | In-house |

TABLE 1-continued

| Gene symbol | Accession number | MW (kDa) | GO Term | Group | Domain | Source |
|---|---|---|---|---|---|---|
| CALR | BC002500.2, BC007911.1, BC020493.1 | 48.1 | Other | Castello | Other | DFCI |
| CCDC137 | BC009369.2 | 33.2 | Other | Baltz/Castello | Other | DFCI |
| CCDC59 | BC020647.1 | 28.7 | Other | Castello | Other | DFCI |
| CCDC75 | BC071798.1 | 18.6 | Other | | Other | DFCI |
| CCDC9 | BC002787.2, BC009743.2 | 59.7 | Other | Baltz/Castello | Other | DFCI |
| CCNL1 | JF432881 | 59.6 | Other | | Other | DNASU |
| CCNL2 | BC016333.1 | 24.6 | Other | | Other | DNASU |
| CCT4 | BC106934.1 | 57.9 | Other | Castello | Other | DFCI |
| CCT6A | BC106942.1 | 58.0 | Other | Castello | Other | DFCI |
| CDC2L5 | NM_003718.3 | 164.9 | Other | | Other | DNASU |
| CDC40 | HQ258473 | 65.5 | Localization | Castello | Other | DNASU |
| CDC42EP4 | BC010451.1 | 38.0 | Other | | Other | DFCI |
| CDC42EP4 | BC002774.1 | 38.0 | Other | | Other | DFCI |
| CELF3 | BC052491.1 | 50.5 | Splicing | | RRM | DFCI |
| CELF4 | BC001946.1 | 51.8 | Translation | | RRM | DFCI |
| CELF5 | BC028101.1 | 52.4 | Other | | RRM | DFCI |
| CHAF1B | | 61.5 | Other | | Other | DNASU |
| CHAF1B | JF432525 | 61.5 | Other | | Other | DNASU |
| CHD2 | BC007347.2 | 56.8 | Other | Baltz/Castello | Other | DFCI |
| CHTOP | BC120961.1 | 26.5 | Localization | Baltz | Other | DFCI |
| CIR1 | BC015040.1 | 23.3 | Other | | Other | DNASU |
| CIRBP | BC000901.1 | 18.6 | Stability | Baltz/Castello | RRM | DFCI |
| CIRBP | BC000403.2 | 18.6 | Stability | Baltz/Castello | RRM | DFCI |
| CIRH1A | BC009348.2 | 76.9 | Other | Castello | Other | DFCI |
| CISD2 | BC032300.1 | 15.3 | Other | Castello | Other | DFCI |
| CLASRP | | 77.2 | Splicing | | Other | DNASU |
| CLK1 | BC031549.1 | 57.3 | Splicing | | Other | DNASU |
| CLK2 | BC014067.2 | 60.0 | Splicing | | Other | DNASU |
| CLK3 | BC019881.1 | 58.6 | Splicing | Baltz/Castello | Other | DFCI |
| CLK3 | BC002555.2 | 58.6 | Splicing | Baltz/Castello | Other | DFCI |
| CLP1 | BC000446.1 | 47.6 | Splicing | | Other | DNASU |
| CMSS1 | BC006475.1 | 31.8 | Other | | Other | DFCI |
| CMBP | BC000288.2 | 18.7 | Other | Baltz/Castello | zf-CCHC | DFCI |
| CNBP | BC014911.1 | 18.7 | Other | Baltz/Castello | zf-CCHC | DFCI |
| CNOT1 | | | Stability | Baltz/Castello | Other | In-house |
| CNOT10 | BC002928.2 | 79.4 | Stability | | Other | DNASU |
| CNOT10 | BC002931.2 | 82.3 | Stability | | Other | DNASU |
| CNOT2 | BC011826 | 59.7 | Stability | | Other | DNASU |
| CNOT3 | BC016474 | 81.9 | Stability | | Other | DNASU |
| CNOT4 | BC035590.1 | 63.1 | Stability | Baltz | RRM | DFCI |
| CNOT6 | NM_015455.3 | 63.3 | Stability | | Other | DNASU |
| CNOT6 | BC150174 | 10.3 | Stability | | Other | DNASU |
| CNOT6L | NM_144571 | 63.0 | Stability | | Other | DNASU |
| CNOT6L | BC152816 | 63.0 | Stability | | Other | DNASU |
| CNOT7 | BC007315.2 | 28.4 | Stability | | Other | DFCI |
| CNOT7 | BC060852.1 | 32.7 | Stability | | Other | DFCI |
| CNOT8 | BC017366.2 | 33.5 | Stability | | Other | DFCI |
| COA6 | BC116455.1 | 14.1 | Other | | Other | DFCI |
| CORO1A | BC126385.1, BC126387.1 | 51.0 | Other | | Other | DFCI |
| CPEB1 | BC036348.1 | 53.6 | Translation | | RRM | DNASU |
| CPEB2 | BC103939.1 | 61.3 | Translation | Baltz/Castello | RRM | DFCI |
| CPEB4 | BC036899.1 | 36.2 | Other | Baltz/Castello | RRM | DFCI |
| CPEB4 | BC117150 | 80.2 | Other | Baltz/Castello | RRM | In-house |
| CPNE3 | BC015734.1 | 5.0 | Other | Castello | Other | DFCI |
| CPSF1 | BC017232 | 160.9 | Localization | | Other | DNASU |
| CPSF2 | BC070095.1 | 88.5 | Localization | | Other | DNASU |
| CPSF3 | BC011654 | 77.4 | Localization | | Other | DNASU |
| CPSF3L | AM393218 | 44.1 | Other | | Other | DNASU |
| CPSF4 | BC050738.1 | 27.4 | Modification | Baltz | ZnF-CCCH | DNASU |
| CPSF4 | BC003101.1 | 27.5 | Modification | Baltz | ZnF-CCCH | DNASU |
| CPSF4L | BC157870.1 | 20.7 | Other | | ZnF-CCCH | DNASU |
| CPSF5 | BC001403 | 26.2 | Other | | Other | DNASU |
| CPSF5 | BX537360 | 26.2 | Other | | Other | DNASU |
| CPSF6 | BC005000.1 | 52.3 | Other | Baltz/Castello | RRM | DFCI |
| CPSF6 | BC000714.2 | 63.5 | Other | Baltz/Castello | RRM | DFCI |
| CPSF7 | BC018135.1 | 52.0 | Splicing | Baltz/Castello | RRM | DFCI |
| CRABP2 | | 15.6 | Other | | Other | DNASU |
| CRKRS | NM_016507 | 164.2 | Other | | Other | DNASU |
| CSNK1G2 | | 47.5 | Other | | Other | In-house |
| CSTF1 | BC001011 | 48.4 | Splicing | Baltz/Castello | Other | DNASU |
| CSTF2 | BC017712 | 61.0 | Splicing | Baltz/Castello | RRM | DNASU |
| CSTF2T | BC028239.1 | 64.5 | Other | Baltz/Castello | RRM | DFCI |
| CSTF3 | HQ447685 | 12.1 | Splicing | Baltz | Other | DNASU |
| CTNNA1 | BC031262.1 | 59.5 | Other | Castello | Other | DFCI |

TABLE 1-continued

| Gene symbol | Accession number | MW (kDa) | GO Term | Group | Domain | Source |
|---|---|---|---|---|---|---|
| CUGBP1 | BC031079 | 51.6 | Other | | Other | DNASU |
| CWC15 | BC040946.1 | 26.6 | Splicing | Castello | Other | DFCI |
| DARS | BC000629.2 | 57.1 | Translation | Castello | tRNA | DFCI |
| DAZ2 | BC113006 | 60.4 | Other | | RRM | In-house |
| DAZ3 | BC113005.1 | 49.5 | Other | | RRM | DFCI |
| DAZ4 | BC047480.1, BC047617.1 | 44.1 | Other | | RRM | DFCI |
| DAZAP1 | BC012062.1 | 43.4 | Other | Baltz/Castello | RPM | DFCI |
| DBR1 | BC009472.1 | 61.6 | Splicing | Castello | Other | DFCI |
| DCD | BC062682.1 | 11.3 | Other | | Other | DFCI |
| DCN | BC005322.1 | 39.7 | Other | | Other | DFCI |
| DCP1A | BC007439.2 | 63.3 | Other | | Other | DNASU |
| DCP2 | BC064593.1 | 44.4 | Stability | | Other | DNASU |
| DDX1 | BC012132.1 | 82.4 | Translation | Baltz/Castello | DEAD | DFCI |
| DDX1 | BC012739.2 | 77.9 | Translation | Baltz/Castello | DEAD | DFCI |
| DDX11 | BC011264.1 | 108.3 | Other | | Other | DNASU |
| DDX11 | BC111733.1 | 101.6 | Other | | Other | DNASU |
| DDX17 | BC000595.2 | 72.4 | Other | Baltz/Castello | DEAD | DFCI |
| DDX18 | BC001238.1, BC003360.1, BC024739.1 | 75.4 | Other | Baltz/Castello | DEAD | DFCI |
| DDX19A | BC005162.2, BC006544.2 | 54.0 | Localization | | DEAD | DFCI |
| DDX19B | BC010008.2 | 41.8 | Localization | | DEAD | DFCI |
| DDX19B | BC003626.2 | 53.9 | Localization | | DEAD | DFCI |
| DDX20 | BC031062.1 | 92.2 | Other | | DEAD | DFCI |
| DDX20 | BC011566 | 92.2 | Other | | DEAD | In-house |
| DDX21 | BC004182 | 79.7 | Other | Baltz/Castello | DEAD | In-house |
| DDX21 | BC008071.2 | 87.3 | Other | Baltz/Castello | DEAD | DNASU |
| DDX23 | BC002366.2 | 95.6 | Splicing | Baltz | DEAD | DFCI |
| DDX24 | BC008847 | 96.3 | Other | Baltz/Castello | DEAD | DNASU |
| DDX27 | HQ253546 | 86.6 | Other | Baltz/Castello | DEAD | DNASU |
| DDX27 | HQ258508 | 89.6 | Other | Baltz/Castello | DEAD | DNASU |
| DDX28 | BC024273.1 | 59.6 | Other | Baltz/Castello | DEAD | DFCI |
| DDX31 | BC012726 | 75.5 | Other | Baltz/Castello | DEAD | In-house |
| DDX31 | BC158832 (NM_138620.1) | 64.1 | Other | Baltz/Castello | DEAD | DNASU |
| DPX39A | BC032128.2 | 36.6 | Localization | Castello | DEAD | DFCI |
| DDX39A | BC001009.2 | 49.1 | Localization | Castello | DEAD | DFCI |
| DDX39A | BC010455.2 | 35.1 | Localization | Castello | DEAD | DFCI |
| DDX41 | BC015476.1 | 69.8 | Splicing | Baltz/Castello | DEAD | DFCI |
| DDX43 | BC066938.1 | 72.9 | Other | | KH | DFCI |
| DDX47 | BC009379.2 | 36.7 | Splicing | Baltz/Castello | DEAD | DFCI |
| DDX49 | BC002674.2 | 54.2 | Other | Castello | DEAD | DFCI |
| DDX5 | BC016027 | 69.1 | Splicing | Baltz/Castello | DEAD | DNASU |
| DDX50 | BC000272.1 | 82.6 | Other | Baltz/Castello | DEAD | DFCI |
| DDX51 | notBC040185 | 11.9 | Other | Baltz/Castello | DEAD | In-house |
| DDX52 | BC041785.1 | 67.5 | Other | Baltz/Castello | DEAD | DFCI |
| DDX53 | BC067878.1 | 71.2 | Other | | KH | DFCI |
| DDX54 | BC001132.2 | 25.5 | Other | Baltz/Castello | DEAD | DFCI |
| DDX55 | BC035911.1 | 24.3 | Other | Castello | DEAD | DFCI |
| DDX55 | BC030020.2 | 68.5 | Other | Castello | DEAD | DFCI |
| DDX56 | BC001235 | 61.7 | Other | Castello | DEAD | DNASU |
| DDX59 | BC041801.1 | 68.9 | Other | | DEAD | DFCI |
| DDX6 | BC085007.1 | 54.4 | Stability | Baltz/Castello | DEAD | DFCI |
| DDX60 | BC020601.1 | 20.8 | Other | | DEAD | DFCI |
| DGCR8 | BC009323.2 | 55.6 | Other | | dsRSD | DFCI |
| DHX18 | BC008825.2, BC009392.2 | 119.4 | Splicing | Baltz/Castello | DEAD | DFCI |
| DHX29 | BC056219.1 | 155.3 | Translation | Baltz | DEAD | DFCI |
| DHX30 | BC014237.2 | 56.5 | Other | Baltz/Castello | dsRBD | DFCI |
| DHX32 | DQ895902 | 84.4 | Other | | Other | DNASU |
| DHX33 | BC042040.1 | 54.6 | Other | Castello | DEAD | DFCI |
| DHX34 | BC172389 | 128.1 | Other | Baltz | DEAD | DNASU |
| DHX35 | HQ258480 | 78.9 | Splicing | | DEAD | DNASU |
| DHX36 | BC036035.1 | 111.5 | Other | Baltz/Castello | DEAD | DFCI |
| DHX37 | BC004463.1 | 3.9 | Other | | DEAD | DNASU |
| DHX38 | BC004235 | 140.5 | Localization | Baltz | DEAD | DNASU |
| DHX40 | BC024187.2 | 88.6 | Other | | DEAD | DNASU |
| DHX57 | BC060778.1 | 63.2 | Other | Baltz/Castello | DEAD | DFCI |
| DHX58 | BC014949 | 76.6 | Other | | Other | In-house |
| DHX58 | JF432115 | 76.6 | Other | | Other | DNASU |
| DHX8 | BC044586.1 | 138.8 | Splicing | Baltz/Castello | DEAD | DFCI |
| DIAPH1 | BC007411 | 141.4 | Other | Castello | Other | DNASU |
| DICER1 | BC150287.1 | 218.7 | Other | | PIWI/PAZ | DFCI |
| DIEXF | BC022964.1 | 87.1 | Other | Castello | Other | DFCI |
| DIMT1 | BC010874.2 | 35.2 | Modification | | Other | DFCI |
| DIS3 | BC038101.1 | 30.8 | Stability | | Other | DNASU |

TABLE 1-continued

| Gene symbol | Accession number | MW (kDa) | GO Term | Group | Domain | Source |
|---|---|---|---|---|---|---|
| DIS3L | BC022089.2 | 111.1 | Other | | Other | DNASU |
| DKC1 | BC010015.2 | 57.7 | Modification | Castello | Other | DFCI |
| DMGDH | BC156312 | 96.8 | Other | Castello | Other | DNASU |
| DMPK | BC062553 | 69.4 | Other | | Other | DNASU |
| DNAJC17 | BC000048.2 | 34.7 | Other | | RRM | DFCI |
| DNAJC2 | BC056682.1 | 19.0 | Other | Castello | Other | DFCI |
| DNAJC5 | BC053642.1 | 22.1 | Other | | Other | DFCI |
| DND1 | BC033496.1 | 38.7 | Other | | RRM | DFCI |
| DNTTIP2 | BC130622.1 | 84.5 | Other | Baltz/Castello | Other | DFCI |
| DPPA5 | BC137549.1 | 13.5 | Other | | Other | DFCI |
| DUS2L | BC006527.2 | 55.0 | Other | | Other | DFCI |
| DUT | BC033645.1 | 17.7 | Other | Castello | Other | DFCI |
| DYNC1H1 | BC064521.1 | 22.2 | Other | Baltz/Castello | Other | DFCI |
| DYNC1LI1 | BC131620.1 | 58.6 | Other | Castello | Other | DFCI |
| DZIP3 | BC083882.1 | 138.6 | Other | Castello | Zn-Finger | DFCI |
| EBNA1BP2 | BC009175.2 | 34.9 | Other | Baltz/Castello | Other | DFCI |
| EDC3 | BC011534.1, BC021271.2 | 56.1 | Stability | | LSM | DNASU |
| EDF1 | BC015500.1 | 16.4 | Other | Baltz/Castello | Other | DFCI |
| EEF1A1 | BC008557.1, BC009733.1, BC009875.2, BC010735.1, BC012891.1, BC014224.2, BC018150.1, BC018641.2, BC010669.1, BC021686.1, BC028674.1, BC038339.1, BC066893.1 | 50.1 | Translation | Baltz/Castello | Other | DFCI |
| EEF1A1 | notBC131708 | 50.1 | Translation | Baltz/Castello | Other | In-house |
| EEF2 | BC126259.1 | 95.3 | Translation | Baltz/Castello | Other | DFCI |
| EFTUD2 | BC002360.2 | 109.5 | Splicing | Baltz/Castello | Other | DFCI |
| EIF2AK2 | BC101475.1 | 62.1 | Translation | Baltz | dsRBD | DFCI |
| EIF2C1 | BC083275.1 | 97.2 | Other | Baltz | Other | DFCI |
| EIF2C2 | BC007633.1 | 42.4 | Other | Baltz/Castello | Other | DFCI |
| EIF2C2 | BC018727.1 | 66.3 | Other | Baltz/Castello | Other | DFCI |
| EIF2C3 | BC066888.1 | 25.6 | Other | Baltz/Castello | Other | DFCI |
| EIF2S2 | BC000934.2 | 38.4 | Translation | Baltz/Castello | Other | DFCI |
| EIF2S2 | BC000461.2 | 38.4 | Translation | Baltz/Castello | Other | DFCI |
| EIF3C | BC001571.1 | 105.3 | Translation | Baltz/Castello | Other | DFCI |
| EIF3D | BC080515.1 | 64.0 | Translation | Baltz/Castello | Other | DFCI |
| EIF3G | BC000733.2 | 35.6 | Translation | Baltz/Castello | RRM | DFCI |
| EIF3H | BC000386.2 | 39.9 | Translation | Castello | Other | DFCI |
| EIF3L | BC001101.2, BC007510.2 | 66.7 | Translation | Baltz/Castello | Other | DFCI |
| EIF4A1 | BC009585.1 | 46.2 | Stability | Baltz/Castello | DEAD | DFCI |
| EIF4A2 | BC015842.1 | 46.4 | Stability | Baltz/Castello | DEAD | DFCI |
| EIF4A2 | BC012547 | 46.5 | Stability | Baltz/Castello | DEAD | In-house |
| EIF4A2 | BC016295 | 21.0 | Stability | Baltz/Castello | DEAD | In-house |
| EIF4A2 | BC048105 | 46.5 | Stability | Baltz/Castello | DEAD | In-house |
| EIF4A3 | BC004386.1, BC011151.1 | 46.9 | Stability | Baltz/Castello | DEAD | DFCI |
| EIF4A3 | BC003662 | 46.9 | Stability | Baltz/Castello | DEAD | In-house |
| EIF48 | BC073139.1 | 69.2 | Stability | Baltz/Castello | RRM | DFCI |
| EIF4H | BC021214.2, BC066928.1 | 25.2 | Translation | Baltz/Castello | RRM | DFCI |
| EIF5B | BC032639.1 | 138.8 | Translation | Baltz/Castello | Other | DFCI |
| ELAC2 | BC001939.1 | 92.2 | Other | Baltz/Castello | Other | DFCI |
| ELAVL1 | BC003376 | 36.1 | Stability | Baltz/Castello | RRM | In-house |
| ELAVL2 | BC030692.1 | 38.0 | Other | Baltz/Castello | RRM | DFCI |
| ELAVL3 | BC014144 | 39.5 | Other | | RRM | In-house |
| ELAVL4 | BC036071.1 | 40.4 | Other | | RRM | DFCI |
| ELMOD3 | BC001942.1 | 44.3 | Other | | Other | DNASU |
| EMG1 | BC055314.1 | 26.7 | Other | Baltz/Castello | Other | DFCI |
| ENOX1 | BC024178 | 73.3 | Other | | RRM | In-house |
| ENOX2 | BC019254.1 | 36.9 | Other | | RRM | DFCI |
| ERAL1 | BC019094.2 | 48.3 | Other | Baltz/Castello | KH | DFCI |
| ERCC3 | BC008820.2 | 89.3 | Other | | Other | DFCI |
| ERI3 | BC001072.2 | 14.5 | Other | Baltz/Castello | Other | DFCI |
| ESRP1 | BC067098.1 | 75.6 | Splicing | | RRM | DFCI |
| EWSR1 | BC000527 | 37.8 | Other | Baltz/Castello | RRM | In-house |
| EWSR1 | BC004817 | 68.5 | Other | Baltz/Castello | RRM | In-house |
| EWSR1 | BC011048 | 68.4 | Other | Baltz/Castello | RRM | In-house |
| EWSR1 | BC072442 | 68.4 | Other | Baltz/Castello | RRM | In-house |
| EXOSC1 | BC022067.2 | 21.5 | Stability | | Other | DNASU |

TABLE 1-continued

| Gene symbol | Accession number | MW (kDa) | GO Term | Group | Domain | Source |
|---|---|---|---|---|---|---|
| EXOSC10 | BC073788.1 | 100.8 | Stability | Baltz/Castello | Other | DNASU |
| EXOSC2 | BC000747 | 32.9 | Stability | | Other | DNASU |
| EXOSC3 | BC008880.2 | 29.6 | Stability | | Other | DNASU |
| EXOSC3 | BC002437.2 | 29.6 | Stability | | Other | DNASU |
| EXOSC4 | BC002777.2 | 26.4 | Stability | | Other | DNASU |
| EXOSC5 | BC007742.2 | 25.3 | | | Other | DNASU |
| EXOSC7 | BC012831.2 | 31.8 | Stability | | Other | DNASU |
| EXOSC8 | BC020773.1 | 30.0 | Stability | | Other | DNASU |
| EXOSC9 | | 48.9 | Stability | Castello | Other | DNASU |
| EZR | BC013903.2 | 89.4 | Other | Baltz/Castello | Other | DFCI |
| FAM120A | BC111736.1 | 121.9 | Other | Baltz/Castello | Other | DFCI |
| FAM120A | BC098584.1 | 121.9 | Other | Baltz/Castello | Other | DFCI |
| FAM208A | BC129986.1 | 125.4 | Other | | Other | DFCI |
| FAM32A | BC090639.1, BC017286.1 | 13.2 | Other | Castello | Other | DFCI |
| FAM46A | BC000683.2 | 49.7 | Other | Castello | Other | DFCI |
| FAM98A | CCSB53266.1 | 55.3 | Other | Baltz/Castello | Other | DFCI |
| FAM98A | BC060860.1 | 55.2 | Other | Baltz/Castello | Other | DFCI |
| FANCM | BC036056.1 | 75.6 | Other | | Other | DFCI |
| FASN | BC007909.1 | 48.3 | Other | Baltz/Castello | Other | DFCI |
| FASTK | BC011770.2 | 61.1 | Splicing | | Other | DFCI |
| FASTKD1 | BC032687.2 | 77.2 | Other | Baltz/Castello | Other | DFCI |
| FASTKD2 | BC001544.1 | 81.5 | Other | Baltz/Castello | Other | DFCI |
| FASTKD3 | BC113563.1 | 75.7 | Other | Castello | Other | DFCI |
| FASTKD5 | BC007413.2 | 88.8 | Other | Baltz | Other | DFCI |
| FBL | BC019260.1 | 33.8 | Modification | Baltz/Castello | Other | DFCI |
| FCF1 | BC080600.1 | 12.8 | Other | Castello | Other | DFCI |
| FDPS | BC010004.2 | 48.3 | Other | Castello | Other | DFCI |
| FGF17 | BC113489.1 | 24.9 | Other | | Other | DFCI |
| FGF17 | | 24.9 | Other | | Other | DNASU |
| FGF19 | BC017664.1 | 24.0 | Other | | Other | DFCI |
| FGF19 | JF432499 | 24.0 | Other | | Other | DNASU |
| FIP1L1 | AL136310 | 58.4 | Other | Baltz/Castello | Other | DNASU |
| FKBP3 | BC016288.1, BC020809.1 | 25.2 | Other | Castello | Other | DFCI |
| FKBP4 | BC001786.1, BC007924.2 | 51.8 | Other | Castello | Other | DFCI |
| FLYWCH2 | BC014089.2 | 14.6 | Other | Castello | Other | DFCI |
| FMR1 | BC038998 | 34.1 | Localization | Baltz/Castello | KH | In-house |
| FNDC3B | BC012204.1 | 7.3 | Other | Castello | Other | DFCI |
| FRG1 | BC053397.1 | 29.2 | Splicing | Castello | Other | DFCI |
| FSCN1 | BC000521.2, BC007348.2 | 54.5 | Other | Castello | Other | DFCI |
| FTO | NM_001080432 | 58.3 | Modification | | Other | DNASU |
| FTSJ3 | BC000131.1 | 65.7 | Other | Baltz/Castello | Other | DFCI |
| FUBP1 | BC017247 | 68.7 | Other | Baltz/Castello | KH | DNASU |
| FUBP3 | BC007874.2 | 28.5 | Other | Baltz/Castello | KH | DFCI |
| FUS | BC000402.2, BC082459.1 | 53.4 | Splicing | Baltz/Castello | RRM | DFCI |
| FUSIP1 | BC010074 | 21.0 | Other | | Other | In-house |
| FXR2 | BC020090.1 | 74.2 | Other | Baltz/Castello | KH | DFCI |
| FXR2 | BC051907.1 | 74.2 | Other | Baltz/Castello | KH | DFCI |
| FZD10 | BC074997.2 | 66.3 | Other | | Other | DFCI |
| FZD3 | NM_017412 | 76.3 | Other | | Other | DNASU |
| FZD4 | BC114527.1 | 59.9 | Other | | Other | DFCI |
| FZD4 | | 59.9 | Other | | Other | DNASU |
| FZD7 | BC015915.1 | 63.8 | Other | | Other | DFCI |
| FZD8 | BC111845 | 73.3 | Other | | Other | DNASU |
| FZD9 | BC026333 | 64.5 | Other | | Other | DNASU |
| G3BP1 | BC000997.1 | 52.2 | Other | Baltz/Castello | RRM | DFCI |
| G3BP2 | BC011731.2 | 50.8 | Localization | Baltz/Castello | RRM | DFCI |
| GANAB | BC065266.1 | 96.2 | Other | Castello | Other | DFCI |
| GAFDH | BC001601.1, BC004109.2, BC009081.1, BC013310.2, BC023632.2, BC025925.1, BC026907.1, BC029618.1 | 36.1 | Other | | Other | DNASU |
| GAR1 | BC003413.1 | 22.3 | Other | Baltz/Castello | Other | DFCI |
| GFM1 | BC049210.1 | 83.5 | Translation | Castello | Other | DFCI |
| GLE1 | BC030012.1 | 79.9 | Localization | | Other | DNASU |
| GLRX3 | BC014372.1 | 21.5 | Other | Castello | Other | DFCI |
| GLRX3 | BC005289.1 | 37.4 | Other | Castello | Other | DFCI |
| GLTSCR2 | BC006311.2, BC010095.2 | 54.4 | Other | Baltz/Castello | Other | DFCI |
| GNB2L1 | BC014788.1 | 35.1 | Other | Baltz/Castello | Other | DFCI |

TABLE 1-continued

| Gene symbol | Accession number | MW (kDa) | GO Term | Group | Domain | Source |
|---|---|---|---|---|---|---|
| GNL2 | BC000107.2 | 83.7 | Other | Baltz/Castello | Other | DFCI |
| GNL2 | BC009250.2 | 83.7 | Other | Baltz/Castello | Other | DFCI |
| GNL3 | BC001024.2 | 62.0 | Other | Baltz/Castello | Other | DFCI |
| GNL3L | BC011720.2 | 65.6 | Other | Castello | Other | DFCI |
| GPANK1 | BC008783.1 | 39.3 | Other | | Other | DFCI |
| GPATCH2 | BC063474.1 | 42.6 | Other | | Other | DFCI |
| GPATCH4 | BC056904.1 | 50.4 | Other | Castello | G-patch | DFCI |
| GPKOW | BC090397.2 | 52.2 | Other | | G-patch | DPCl |
| GRB2 | BC000631.2 | 25.2 | Other | Castello | Other | DFCI |
| GRN | BC000324.2 | 47.0 | Other | Castello | Other | DFCI |
| GRN | BC010577.2 | 63.5 | Other | Castello | Other | DFCI |
| GSPT1 | BC009503.2 | 68.4 | Stability | Baltz/Castello | Other | DFCI |
| GSPT2 | BC036077.1 | 69.0 | Stability | Baltz/Castello | Other | DFCI |
| GTF2E2 | BC030572.2 | 33.0 | Other | Castello | Other | DFCI |
| GTF2F1 | BC000120.1 | 58.2 | Splicing | Baltz/Castello | Other | DFCI |
| GTPBP10 | BC021573.1 | 39.7 | Other | Castello | Other | DFCI |
| GTPSP4 | BC038975.2 | 74.0 | Other | Baltz/Castello | Other | DFCI |
| GTSF1 | BC021179.1 | 19.2 | Other | | Other | DFCI |
| GTSF1L | BC040049.1 | 16.9 | Other | | Other | DFCI |
| HADHB | BC014572.1 | 51.4 | Other | | Other | DFCI |
| HADHB | BC017554.2, BC030824.1, BC066963.1 | 51.4 | Other | | Other | DFCI |
| HDGF | BC018991.1 | 26.8 | Other | Castello | Other | DFCI |
| HEATR1 | BC062442.1 | 13.5 | Other | Baltz/Castello | Other | DFCI |
| HEATR1 | BC011983.1 | 39.9 | Other | Baltz/Castello | Other | DFCI |
| HELQ | BC011863.2 | 30.5 | Other | | Other | DFCI |
| HERC5 | BC140716.1 | 116.8 | Other | Castello | Other | DFCI |
| HFM1 | BC132823.1 | 53.6 | Other | | Other | DFCI |
| HIST1H1C | BC002649.1 | 21.4 | Other | Baltz/Castello | Other | DFCI |
| HIST1H4H | BC120939.2 | 11.4 | Other | Castello | Other | DFCI |
| HMGB1 | BC003378.1 | 24.9 | Other | Baltz/Castello | Other | DFCI |
| HMGB2 | BC001063.2 | 24.0 | Other | Baltz/Castello | Other | DFCI |
| HNRNPA0 | hnRNPA0 | 30.8 | Other | | RRM | Promega |
| HNRNPA1 | BC002335.2, BC009800.1, BC812158.1, BC033714.1 | 34.2 | Localization | Baltz/Castello | RRM | DFCI |
| HNRNPA1 | hnRNPA1 | 34.2 | Other | | RRM | Promega |
| HNRNPA2B1 | BC000506.2 | 28.4 | Localization | Baltz/Castello | RRM | DFCI |
| HNRNPC | BC008423.1 | 33.6 | Splicing | Baltz/Castello | RRM | DFCI |
| HNRNPC | BC003394 | 32.3 | Splicing | Baltz/Castello | RRM | In-house |
| HNRNPC | BC008364 | 32.4 | Splicing | Baltz/Castello | RRM | In-house |
| HNRNPC1/2 | hnRNPC1/2 | 33.7 | Other | | Other | Promega |
| HNRNPCL1 | BC137258.1 | 32.1 | Other | Baltz | RRM | DFCI |
| HNRNPD | BC002401.1 | 38.4 | Stability | Baltz/Castello | RRM | DFCI |
| HNRNPD0 | hnRNPD0 | 32.8 | Other | | Other | Promega |
| HNRNPE1 | hnRNPE1 | 37.5 | Other | | Other | Promega |
| HNRNPE2 | hnRNPE2 | 38.2 | Other | | Other | Promega |
| HNRNPF | BC004254.1 | 45.7 | Splicing | Baltz/Castello | RRM | DFCI |
| HNRNPF | BC001432 | 45.7 | Splicing | Baltz/Castello | RRM | |
| HNRNPF | BC016736 | 45.7 | Splicing | Baltz/Castello | RRM | In-house |
| HNRNPF | hnRNPF | 45.7 | Other | | RRM | Promega |
| HNRNPH | hnRNPH | 51.2 | Other | | Other | Promega |
| HNRNPH1 | BC001348.2 | 49.2 | Splicing | Baltz/Castello | RRM | DFCI |
| HNRNPH2 | BC130345.1 | 49.3 | Splicing | Baltz/Castello | RRM | DFCI |
| HNRNPH2 | | | Splicing | Baltz/Castello | RRM | In-house |
| HNRNPI | hnRMPI | 57.2 | Other | | Other | In-house |
| HNRNPK | BC000355.2 | 51.0 | Splicing | Baltz/Castello | KH | DFCI |
| HNRNPK | BC014980 | 51.0 | Splicing | Baltz/Castello | KH | In-house |
| HNRNPK | hnRNPK | 48.6 | Other | | KH | Promega |
| HNRNPL | hnRNPL | | Other | | RRM | Promega |
| HNRNPM | BC000138 | 77.5 | Splicing | Baltz/Castello | RRM | In-house |
| HNRNPP2 | hnRNPP2 | 53.4 | Other | | Other | Promega |
| HNRNPQ | hnRNPQ | 69.6 | Other | | Other | Promega |
| HNRNPR | BC001449.2 | 71.2 | Splicing | Baltz/Castello | RRM | DFCI |
| HNRNPR | hnRNPR | 70.9 | Other | | RRM | Promega |
| HNRNPU | BC003367 | 89.0 | Stability | Baltz/Castello | Other | In-house |
| HNRNPU | hnRNPU | 89.0 | Other | | Other | In-house |
| HNRNPUL1 | BC027713.2 | 90.3 | Splicing | Baltz/Castello | Other | DFCI |
| HNRNPUL1 | hnRNPUL1 | 95.7 | Other | | Other | Promega |
| HNRNPUL2 | NM_001079559.1 | 85.1 | Other | Baltz/Castello | Other | DNASU |
| HNRPDL | BC007392.2 | 33.6 | Other | Castello | Other | DFCI |
| HNRPLL | BC008217.1 | 30.8 | Other | Baltz/Castello | Other | DFCI |
| HNRPLL | BC017480 | 80.1 | Other | Baltz/Castello | Other | In-house |
| HRSP12 | BC010280.1, BC012592.1 | 14.5 | Translation | Castello | Other | DFCI |
| HSP90AA1 | BC121062.2 | 84.7 | Other | Baltz/Castello | Other | DFCI |

TABLE 1-continued

| Gene symbol | Accession number | MW (kDa) | GO Term | Group | Domain | Source |
|---|---|---|---|---|---|---|
| HSP90AB1 | BC004926.1, BC012807.2 | 83.3 | Other | Baltz/Castello | Other | DFCI |
| HSPA8 | BC007276.1 | 64.6 | Other | Baltz/Castello | Other | DFCI |
| HSPA8 | BC018179.1, BC016680.1 | 70.9 | Other | Baltz/Castello | Other | DFCI |
| HSPA9 | BC000478.2 | 73.7 | Other | Baltz/Castello | Other | DFCI |
| HSPB1 | BC073768, BC000510 | 22.9 | Other | Castello | Other | DNASU |
| HSPD1 | BC003030.1 | 61.1 | Other | Castello | Other | DFCI |
| HSPD1 | BC002676.2 | 61.1 | Other | Castello | Other | DFCI |
| HTATSF1 | BC009896.2 | 85.9 | Other | Castello | RRM | DFCI |
| HTATSF1-DPF3 | nolBC009896 | 85.9 | Other | | Other | In-house |
| HYPE | BC001342 | 50.8 | Other | | Other | In-house |
| IFI16 | BC017059.1 | 82.0 | Other | Castello | Other | DFCI |
| IFIH1 | BC111750.1 | 116.7 | Other | | Other | DFCI |
| IFIH1 | BC046206.1 | 25.1 | Other | | Other | DFCI |
| IFIT2 | BC032839.2 | 56.2 | Other | Castello | Other | DFCI |
| IGF2BP1 | NM_006546.3 | 63.5 | Stability | Baltz/Castello | RRM | DNASU |
| IGF2BP2 | BC021290.2 | 66.0 | Translation | Baltz/Castello | RRM | DFCI |
| IGF2BP3 | BC065269.1 | 63.7 | Translation | Baltz/Castello | RRM | DFCI |
| IGF2BP3 | BC051296.1 | 11.3 | Translation | Baltz/Castello | RRM | DFCI |
| IGFBP6 | | 25.3 | Other | | Other | In-house |
| ILF2 | BC000382.2 | 43.1 | Other | Baltz/Castello | Zn-Finger | DFCI |
| ILF3 | BC064838.1 | 76.5 | Other | Baltz/Castello | dsRBD | DFCI |
| ILF3 | BC003086.1 | 17.8 | Other | Baltz/Castello | dsRBD | DFCI |
| INTS6 | BC039829.1 | 100.4 | Other | | Other | DNASU |
| ISY1 | BC004442.1, BC019849.1 | 33.0 | Splicing | Castello | Other | DFCI |
| KHDRBS2 | BC034043.1 | 38.9 | Other | | KH | DFCI |
| KHDRBS3 | BC032606 | 38.8 | Other | Baltz | KH | In-house |
| KIAA0020 | BC016137.2 | 73.8 | Other | Baltz/Castello | Other | DFCI |
| KIAA1324 | BC125208.1 | 102.0 | Other | | Other | DFCI |
| KIAA1967 | BC018269.1 | 40.8 | Other | Baltz/Castello | Other | DFCI |
| KIF1C | BC034993.1 | 122.9 | Other | Baltz/Castello | Other | DFCI |
| KIF1C | BC111736.1 | 121.9 | Other | Baltz/Castello | Other | DNASU |
| KLKL3 | BC034035 | 34.1 | Other | | Other | In-house |
| KRR1 | BC026107.2 | 43.8 | Other | Baltz/Castello | KH | DFCI |
| KRR1 | BC033867.2 | 43.8 | Other | Baltz/Castello | KH | DFCI |
| KRR1 | BC016778.1 | 43.8 | Other | Baltz/Castello | KH | DFCI |
| KRT18 | BC000698.2 | 48.0 | Other | Castello | Other | DFCI |
| LARP1 | BC001460.2 | 116.5 | Other | Baltz/Castello | Other | DFCI |
| LARP1 | BC010144 | 5.8 | Other | Baltz/Castello | Other | In-house |
| LARP1 | BC033856 | 32.9 | Other | Baltz/Castello | Other | In-house |
| LARP1B | BC030516.1 | 24.1 | Other | Baltz | Other | DFCI |
| LARP1B | BC062606.1 | 29.0 | Other | Baltz | Other | DFCI |
| LARP4 | BC022377.1 | 21.5 | Other | Baltz/Castello | RRM | DFCI |
| LARP4 | BC083479.1 | 42.0 | Other | Baltz/Castello | RRM | DFCI |
| LARP4B | BC131630.1 | 80.6 | Translation | Baltz/Castello | RRM | DFCI |
| LARP8 | BC006082.1, BC009446.1, BC014018.2 | 54.7 | Translation | | Other | DFCI |
| LARP7 | BC066945.1 | 86.9 | Other | Baltz/Castello | RRM | DFCI |
| LGALS1 | BC001693.1, BC020675.1 | 14.7 | Other | Castello | Other | DFCI |
| LGALS3 | BC053667.1 | 26.2 | Other | Castello | Other | DFCI |
| LIN28A | BC028566.2 | 22.7 | Translation | | zf-CCHC | DFCI |
| LIN28B | BC137526.1 | 27.1 | Other | Baltz | zf-CCHC | DFCI |
| LLPH | BC006002.1 | 15.2 | Other | Baltz/Castello | Other | DFCI |
| LSM1 | BC001767.1 | 15.2 | Stability | Baltz/Castello | LSM | DFCI |
| LSM10 | BC007623.1 | 14.1 | Splicing | | LSM | DFCI |
| LSM11 | BC126449 | 39.5 | Other | | LSM | In-house |
| LSM2 | BC009192.2 | 10.8 | Stability | Baltz/Castello | LSM | DFCI |
| LSM3 | BC007055.1 | 11.8 | Stabhty | Baltz/Castello | LSM | DFCI |
| LSM4 | BC000387.2, BC003652.2, BC022198.2, BC023665.2 | 15.3 | Stability | Baltz/Castello | LSM | DFCI |
| LSM5 | BC005938.1 | 9.9 | Stability | | LSM | DFCI |
| LSM6 | BC018026.1 | 9.1 | Stability | Baltz | LSM | DFCI |
| LSM7 | BC018621.1 | 11.8 | Stability | | LSM | DFCI |
| LSMD1 | BC033861.1 | 18.7 | Other | | LSM | DFCI |
| LSMD1 | BC059944.1 | 13.5 | Other | | LSM | DFCI |
| LUC7L | HQ448098 | 41.9 | Other | | Other | DNASU |
| LUC7L2 | BC017163.2, BC050708.2, BC056886.1 | 46.5 | Other | Baltz/Castello | Other | DFCI |
| LUC7L3 | BC056409.1 | 9.2 | Splicing | Baltz/Castello | Other | DFCI |
| LYAR | BC015796.2 | 43.6 | Other | Baltz/Castello | Other | DFCI |

TABLE 1-continued

| Gene symbol | Accession number | MW (kDa) | GO Term | Group | Domain | Source |
|---|---|---|---|---|---|---|
| MAGOHB | BC010905 | 17.3 | Localization | | Other | In-house |
| MAK16 | BC050528.1 | 35.4 | Other | Castello | Ribosomal | DFCI |
| MAP4 | BC008715.2, BC012794.2 | 102.9 | Other | Baltz/Castello | Other | DFCI |
| MATR3 | BC015031 | 94.6 | Other | Baltz/Castello | RRM | DNASU |
| MA2 | BC041629.1 | 28.6 | Other | Baltz/Castello | Zn-Finger | DFCI |
| MBNL1 | BC043493.1 | 41.0 | Splicing | Baltz/Castello | ZnF-CCCH | DFCI |
| MBNL2 | BC104040.1 | 39.3 | Splicing | Baltz/Castello | ZnF-CCCH | DFCI |
| MDH2 | BC001917.1 | 35.5 | Other | Baltz/Castello | Other | DFCI |
| MECP2 | BC011612.1 | 52.4 | Other | Castello | Other | DFCI |
| MBPCE | BC000556.2, BC018396.1 | 25.0 | Modification | Baltz/Castello | Other | DFCI |
| METYL16 | BC050603.1 | 63.6 | Other | Baltz | Other | DFCI |
| METTL3 | BC052244 | 64.4 | Modification | | Other | DNASU |
| MEX3C | NM_018626 | 89.4 | Other | Baltz/Castello | KH | DNASU |
| MFAP1 | BC023557.2, BC050742.1 | 52.0 | Other | Baltz/Castello | Other | DFCI |
| MKI67IP | BC022990.1 | 34.2 | Other | Baltz/Castello | Other | DFCI |
| MKI67IP | BC024238.2 | 34.3 | Other | Baltz/Castello | Other | DFCI |
| MOV10 | BC002548.1, BC009312.2 | 113.7 | Other | Baltz/Castello | Other | DFCI |
| MPHOSPH6 | BC031017.1 | 19.0 | Other | | Other | DNASU |
| MRM1 | BC072411.1 | 38.6 | Other | Baltz/Castello | Other | DFCI |
| MRPL1 | BC014356.1, BC032595.1 | 34.5 | Translation | Baltz/Castello | Ribosomal | DFCI |
| MRPL11 | BC005002.1 | 20.7 | Translation | Baltz/Castello | Ribosomal | DFCI |
| MRPL13 | BC009190.2, BC021744.2 | 20.7 | Translation | Baltz/Castello | Ribosomal | DFCI |
| MRPL3 | BC003375.2 | 38.6 | Translation | Baltz/Castello | Ribosomal | DFCI |
| MRPL30 | BC022391.1 | 18.5 | Other | | Ribosomal | DFCI |
| MRPL32 | BC013147.1 | 21.4 | Translation | Castello | Ribosomal | DFCI |
| MRPL37 | BC000041.2 | 48.1 | Translation | Castello | Other | DFCI |
| MRPL39 | BC004896.2 | 38.2 | Other | Castello | Other | DFCI |
| MRPL4 | BC009856.2 | 34.9 | Translation | Baltz/Castello | Ribosomal | DFCI |
| MRPL41 | BC040035.1 | 15.4 | Translation | Baltz/Castello | Other | DFCI |
| MRPL42 | BC040240.1 | 18.7 | Translation | Castello | Other | DFCI |
| MRPL43 | BC041165.1 | 23.4 | Translation | Castello | Other | DFCI |
| MRPL45 | BC006235.2 | 28.8 | Translation | Baltz/Castello | Other | DFCI |
| MRPL45 | BC130382.1, BC130384.1 | 35.4 | Translation | Baltz/Castello | Other | DFCI |
| MRPS11 | BC012489.1 | 20.5 | Translation | Baltz/Castello | Ribosomal | DFCI |
| MRPS11 | BC032378.1 | 20.6 | Translation | Baltz/Castello | Ribosomal | DFCI |
| MRPS15 | BC031336.1 | 29.8 | Translation | Castello | Ribosomal | DFCI |
| MRPS23 | BC000242.1 | 21.8 | Translation | Castello | Other | DFCI |
| MRPS24 | BC012167.1 | 19.0 | Translation | Baltz/Castello | Other | DFCI |
| MRPS24 | BC054865.1 | 19.0 | Translation | Baltz/Castello | Other | DFCI |
| MRPS30 | BC007735.2 | 50.4 | Translation | Castello | Other | DFCI |
| MRPS31 | BC022045.1 | 45.3 | Other | Baltz/Castello | Other | DFCI |
| MRPS35 | BC015862.1 | 26.4 | Other | Baltz | Other | DFCI |
| MRPS5 | BC014172.2 | 48.0 | Translation | Baltz/Castello | Ribosomal | DFCI |
| MRPS7 | BC000241.1 | 28.2 | Translation | Baltz/Castello | Ribosomal | DFCI |
| MRTO4 | BC003013.1 | 27.6 | Other | Baltz/Castello | Ribosomal | DFCI |
| MSI1 | BC017560.2 | 17.2 | Other | Baltz/Castello | RRM | DFCI |
| MSI2 | BC001526 | 35.2 | Other | Baltz/Castello | RRM | In-house |
| MTDH | BC045642.1 | 63.3 | Other | Baltz/Castello | Other | DFCI |
| MTPAP | BC061703.1 | 66.2 | Other | Baltz/Castello | Other | DFCI |
| MUSK | GQ129313 | 86.4 | Other | | Other | DNASU |
| MYEF2 | BC014533 | 22.4 | Other | Baltz | RRM | In-house |
| NAA15 | BC104806.1 | 101.3 | Other | Castello | Other | DFCI |
| NANOS1 | BC156179 | 30.2 | Translation | | Zn-Finger | DNASU |
| MANOS2 | BC117484.1, BC117486.1 | 15.1 | Translation | | Zn-Finger | DFCI |
| NANOS3 | BC101209.2 | 20.7 | Translation | | Zn-finger | DFCI |
| NAP1L3 | BC034954 | 57.6 | Other | | Other | DNASU |
| NAT10 | BC035558.1 | 115.7 | Other | Baltz/Castello | tRNA | DFCI |
| NCL | BC002343 | 51.0 | Other | Baltz/Castello | RRM | In-house |
| NDUFV3 | BC033766.1 | 11.9 | Other | Baltz/Castello | Other | DFCI |
| NDUFV3 | BC021217.2 | 51.0 | Other | Baltz/Castello | Other | DFCI |
| NGDN | BC030817.1 | 35.9 | Translation | Baltz/Castello | Other | DFCI |
| NGRM | BC001682.2, BC007222.1, BC009389.2, BC017192.2 | 24.4 | Other | Baltz/Castello | | |
| NHP2 | BC000009.2, BC006387.2 | 17.2 | Other | Castello | Ribosomal | DFCI |
| NHP2L1 | BC019282.2 | 14.2 | Splicing | Baltz/Castello | Ribosomal | DFCI |
| NIP7 | BC015941.1 | 20.5 | Other | Baltz/Castello | Other | DFCI |
| NKRF | BC047878.2 | 77.7 | Other | Baltz/Castello | dsRBD | DFCI |

TABLE 1-continued

| Gene symbol | Accession number | MW (kDa) | GO Term | Group | Domain | Source |
|---|---|---|---|---|---|---|
| NMD3 | BC013317.1 | 57.6 | Other | Castello | Other | DFCI |
| NOA1 | BC004894.2 | 78.5 | Translation | | Other | DFCI |
| NOB1 | BC064630.1 | 46.7 | Other | | Other | DFCI |
| NGC2L | BC003555.1 | 84.9 | Other | Baltz/Castello | Other | DFCI |
| NOL10 | BC005125.2 | 80.3 | Other | Baltz/Castello | Other | DFCI |
| NOL12 | BC002808.1 | 24.7 | Other | Baltz/Castello | Other | DFCI |
| NOL7 | BC023517.2 | 29.4 | Other | Castello | Other | DFCI |
| NOL8 | BC146810.1 | 123.8 | Other | Baltz/Castello | RRM | DFCI |
| NOLC1 | BC006769.2 | 44.2 | Other | Baltz/Castello | Other | DFCI |
| NONO | BC010049.2 | 39.0 | Splicing | Baltz/Castello | RRM | DFCI |
| NONO | BC002364.1, BC003129.1, BC012141.1, BC028299.1, BC069639.1 | 54.2 | Splicing | Baltz/Castello | RRM | DFCI |
| NOP10 | BC008866.2 | 7.7 | Other | | Other | DFCI |
| NOP16 | BC040106.1 | 21.2 | Other | Baltz/Castello | Other | DFCI |
| NOP16 | BC032424.2 | 26.6 | Other | Baltz/Castello | Other | DFCI |
| NOP2 | BC106072.1 | 92.9 | Other | Baltz/Castello | Other | DFCI |
| NOP56 | BC004937.1 | 19.5 | Other | Baltz/Castello | Other | DFCI |
| NOP58 | BC032592.2 | 59.6 | Other | Baltz/Castello | Other | DFCI |
| NOP9 | BC025332.1 | 58.2 | Other | | Other | DFCI |
| NOSIP | BC011249.1 | 33.2 | Other | Castello | Other | DFCI |
| NOSIP | BC009299.2, BC010077.2 | 33.2 | Other | Castello | Other | DFCI |
| NOVA1 | BC075038.2 | 51.7 | Splicing | Baltz | KH | DFCI |
| NPM1 | BC009623.2 | 29.5 | Translation | Baltz/Castello | Other | DFCI |
| NPM1 | BC002398.2, BC008495.1, BC014349.1, BC016716.1, BC018824.1, BC021668.1, BC050628.1 | 32.6 | Translation | Baltz/Castello | Other | DFCI |
| NPM1 | BC012566.1 | 32.6 | Translation | Baltz/Castello | Other | DFCI |
| NPM3 | BC054868.1 | 19.3 | Other | Baltz/Castello | Other | DFCI |
| NR5A1 | BC032501 | 51.6 | Other | | Other | In-house |
| NSA2 | BC005288.1 | 30.1 | Other | Baltz/Castello | Ribosomal | DFCI |
| NSUN2 | BC001041.2 | 63.3 | Modification | Baltz/Castello | Other | DFCI |
| NSUN2 | | 63.3 | Modification | Baltz/Castello | Other | DNASU |
| NSUN5 | BC008084.2 | 50.4 | Other | Baltz/Castello | Other | DFCI |
| NUDT16 | BC031215.1 | 17.8 | Other | | Other | DNASU |
| NUDT16L1 | BC006223.2 | 23.3 | Other | Baltz | Other | DNASU |
| NUFIP2 | BC129990.1 | 76.1 | Other | Baltz/Castello | Other | DFCI |
| NUFIP2 | BC108307.1 | 76.1 | Other | Baltz/Castello | Other | DFCI |
| NUP35 | BC047029.1, BC061896.1 | 34.8 | Other | | Other | DFCI |
| NUSAP1 | BC010838.1 | 24.9 | Other | Castello | Other | DFCI |
| NUSAP1 | BC024772.1 | 49.2 | Other | Castello | Other | DFCI |
| NVL | BC012105.1 | 72.7 | Other | Castello | Other | DFCI |
| NXF1 | BC004904.2, BC028041.1 | 70.2 | Localization | Baltz/Castello | Other | DFCI |
| NXF2 | BC015020.1 | 71.6 | Localization | | Other | DFCI |
| NXF3 | BC031616.1 | 60.1 | Localization | | Other | DFCI |
| NXF5 | BC131708.1 | 42.2 | Localization | | Other | DFCI |
| OASL | BC117406.1, BC117410.1 | 59.2 | Other | Castello | Other | DFCI |
| P4HB | BC010859.1, BC029617.1 | 57.1 | Other | Baltz/Castello | Other | DFCI |
| PA2G4 | BC001951.1, BC007561.1, BC069786.1 | 43.8 | Translation | Castello | Other | DFCI |
| PABPC1 | BC015958 | 70.7 | Stability | Baltz/Castello | RRM | DNASU |
| PABPC1P2 | BC068242.1 | 29.9 | Other | | Other | DNASU |
| PABPC3 | BC027617.2 | 70.0 | Other | | RRM | DFCI |
| PABPC5 | BC063113.1 | 43.3 | Other | | RRM | DFCI |
| PABPN1L | BC148673 | 31.5 | Other | | RRM | DNASU |
| PAN3 | BC128179.1 | 62.0 | Stability | | ZnF-CCCH | DNASU |
| PAPD5 | | 63.3 | Other | | Other | In-house |
| PAPD7 | HQ258305 | 59.9 | Other | | Other | DNASU |
| PAPOLA | BC000927.1 | 32.6 | Splicing | | Other | DFCI |
| PAPOLG | BC111701.1 | 82.8 | Other | | Other | DFCI |
| PARN | BC050029.1 | 73.5 | Modification | Castello | Other | DFCI |
| PARP12 | BC081541.1 | 79.1 | Other | Castello | ZnF-CCCH | DFCI |
| PATL1 | BC085264.1, BC109038.1 | 70.6 | Stability | Baltz/Castello | Other | DFCI |
| PCBP1 | BC039742.1 | 37.5 | Splicing | Baltz/Castello | KH | DFCI |
| PCBP2 | BC001155 | 38.2 | Splicing | Baltz/Castello | KH | In-house |

TABLE 1-continued

| Gene symbol | Accession number | MW (kDa) | GO Term | Group | Domain | Source |
|---|---|---|---|---|---|---|
| PCBP3 | BC012061.1 | 33.3 | Other | Castello | KH | DFCI |
| PCBP4 | BC017098.1 | 37.1 | Other | Castello | KH | DFCI |
| PCSK9 | NM_174938.2 | 74.3 | Other | Castello | Other | DNASU |
| PDIA3 | BC038000.1 | 56.8 | Other | Castello | Other | DFCI |
| PDIA3 | BC014433.1 | 56.8 | Other | Castello | Other | DFCI |
| PDIA4 | BC000425.2 | 72.9 | Other | Castello | Other | DFCI |
| PEG10 | BC060659.2 | 37.0 | Other | Baltz/Castello | Other | DFCI |
| PES1 | BC032489.1 | 68.0 | Other | Baltz/Castello | Other | DFCI |
| PHF5A | BC007321.2 | 12.4 | Splicing | Baltz/Castello | Other | DFCI |
| PHF6 | BC005994.1 | 35.3 | Other | Castello | Other | DNASU |
| PINX1 | BC015479.1 | 37.0 | Other | | G-patch | DFCI |
| PIWIL1 | BC028581.2 | 93.5 | Translation | | PIWI/PAZ | DFCI |
| PIWIL2 | BC025995.1 | 109.8 | Translation | | PIWI/PAZ | DFCI |
| PIWIL4 | BC031080.1 | 96.6 | Translation | | PIWI/PAZ | DFCI |
| PKM | BC007640.1 | 57.9 | Other | | Other | DFCI |
| PLRG1 | BC020786.1 | 56.3 | Splicing | | Other | DNASU |
| PNLDC1 | BC112246.1 | 60.1 | Other | | Other | DFCI |
| PNN | BC062602.1 | 81.6 | Stability | Baltz/Castello | Other | DFCI |
| PNO1 | BC008304.1 | 27.9 | Other | Baltz | KH | DFCI |
| PNRC2 | BC001959.1 | 15.6 | Stability | | Other | DNASU |
| POLDIP3 | BC019643.1 | 24.8 | Translation | Baltz/Castello | RRM | DFCI |
| POLK | BC050718.1 | 64.1 | Other | | Other | DFCI |
| POLR2G | BC112162.1 | 19.3 | Splicing | | S1 | DFCI |
| POLR3E | BC000285.1 | 74.8 | Other | | Other | DFCI |
| PORCN | BC895869 | 51.8 | Other | | Other | DNASU |
| POU5F1 | BC117437.1 | 38.6 | Other | Castello | Other | DFCI |
| PPAN | BC033202.1 | 53.2 | Splicing | Baltz/Castello | Other | DFCI |
| PPAN | BC009833.2 | 53.2 | Splicing | Baltz/Castello | Other | DFCI |
| PPAPDC1A | BC101268.2 | 23.5 | Other | | Other | DNASU |
| PPAPDC1A | BC132787.1 | 30.4 | Other | | Other | DNASU |
| PPAPDC1B | BC033025.1 | 26.2 | Other | | Other | DNASU |
| PPAPDC2 | BC038108.2 | 32.3 | Other | | Other | DNASU |
| PPIA | BC000689.2, BC003026.1, BC005320.1, BC013915.1 | 18.0 | Other | Baltz/Castello | Other | DFCI |
| PPIA | BC005982.1 | 18.0 | Other | Baltz/Castello | Other | DFCI |
| PPIB | BC001125 | 23.7 | Other | Baltz/Castello | Other | DNASU |
| PPIE | BC004898.2, BC008451.1 | 33.4 | Splicing | Castello | RRM | DFCI |
| PPIG | BC111693.1 | 87.1 | Other | Baltz/Castello | Other | DFCI |
| PPIG | BC001555.1 | 40.3 | Other | Baltz/Castello | Other | DFCI |
| PPIL4 | BC016984 | 23.1 | Other | Baltz/Castello | RRM | In-hoase |
| PPIL4 | BC018984.1 | 23.2 | Other | Baltz/Castello | RRM | DFCI |
| PPIL4 | BC020986.1 | 57.2 | Other | Baltz/Castello | RRM | DFCI |
| PPP1CA | BC001888.1, BC004482.2, BC008010.1 | 37.6 | Other | | Other | DNASU |
| PPP1CB | AM392772 | 37.2 | Other | | Other | DNASU |
| PRKRA | BC008470.1 | 34.4 | Other | Baltz | dsRBD | DFCI |
| PRMT1 | | 39.4 | Other | Baltz | Other | DNASU |
| PRPF18 | BC000794 | 39.9 | Splicing | | other | DNASU |
| PRPF19 | BC008719.2 | 55.2 | Splicing | | Other | DNASU |
| PRPF3 | BC000184.2, BC001954.1 | 77.5 | Splicing | Baltz | Other | DNASU |
| PRPF31 | BC117389.1 | 55.5 | Splicing | Baltz/Castello | Other | DFCI |
| PRPF38B | BC053838.1 | 21.1 | Splicing | Castello | Other | DFCI |
| PRPF4 | BC001588.2 | 58.4 | Splicing | | Other | DNASU |
| PRPF4 | BC007424.2 | 58.3 | Splicing | | Other | DNASU |
| PRPF40A | BC027178.1 | 25.5 | Splicing | Baltz | Other | DNASU |
| PRPF4B | BC034969 | 117.0 | Splicing | Baltz | Other | DNASU |
| PRPF6 | BC001666.2 | 108.9 | Localization | Castello | Other | DFCI |
| PRPF8 | | 273.6 | Splicing | Baltz/Castello | RRM | DNASU |
| PRR3 | BC126455.1 | 20.6 | Other | Baltz/Castello | ZnF-CCCH | DFCI |
| PRR3 | BC126457.1 | 20.7 | Other | Baltz/Castello | ZnF-CCCH | DFCI |
| PRRC2B | BC012289.1 | 34.4 | Other | Baltz/Castello | Other | DFCI |
| PSMA3 | BC005265 | 28.4 | Other | | Other | In-house |
| PSMC1 | BC000512.2 | 49.2 | Other | | Other | DFCI |
| PSMC1 | BC016368.1 | 49.2 | Other | | Other | DFCI |
| PSMD4 | BC002365.2 | 40.7 | Other | Castello | Other | DFCI |
| PSPC1 | BC014184.2 | 45.6 | Other | Baltz/Castello | RRM | DFCI |
| PTBP1 | BC004383.1 | 67.2 | Splicing | Baltz/Castello | RPM | DFCI |
| PTBP1 | BC002397 | 59.6 | Splicing | Baltz/Castello | RRM | In-house |
| PTBP2 | BC018582 | 67.6 | Splicing | Baltz/Castello | RRM | In-house |
| PTBP3 | BC044585.1 | 60.4 | Splicing | | RRM | DFCI |
| PTCD1 | BC103495.1 | 78.9 | Other | Baltz/Castello | Other | DFCI |
| PTCD2 | BC018720.1 | 26.7 | Other | Baltz/Castello | Other | DFCI |
| PTCD3 | BC011832.2 | 63.1 | Translation | Baltz/Castello | Other | DFCI |

TABLE 1-continued

| Gene symbol | Accession number | MW (kDa) | GO Term | Group | Domain | Source |
|---|---|---|---|---|---|---|
| PTRF | BC065123.1 | 43.5 | Other | | Other | DFCI |
| PTRH1 | BC047012.1 | 22.9 | Other | Castello | tRNA | DFCI |
| PUF60 | BC009734.1 | 54.0 | Splicing | Baltz/Castello | RRM | DFCI |
| PUF60 | BC011265.1, BC011879.1 | 55.7 | Splicing | Baltz/Castello | RRM | DFCI |
| PUF60 | BC008875.2 | 58.2 | Splicing | Baltz/Castello | RRM | DFCI |
| PUM1 | BC013398.2 | 126.5 | Translation | Baltz/Castello | Pumilio | DFCI |
| PURB | BC101735.1 | 33.2 | Other | Baltz/Castello | Other | DFCI |
| PURG | BC106708.2 | 39.6 | Other | Baltz | Other | DFCI |
| PUS7 | BC005209.2 | 29.8 | Modification | Baltz/Castello | Other | DFCI |
| PUS7 | BC011398 | 29.8 | Modification | | Other | In-house |
| PUS7L | BC068502.1 | 80.7 | Modification | | Other | DFCI |
| PUS7L | BC033621.2 | 80.7 | Modification | | Other | DFCI |
| PWP2 | BC013309.2, BC014986.1 | 102.4 | Other | Baltz/Castello | Other | DFCI |
| OARS | BC001772.1 | 69.8 | Translation | | tRNA | DFCI |
| OARS | BC016634.1 | 69.8 | Translation | | TRNA | DFCI |
| OKI | BC019917.2 | 37.7 | Translation | Baltz | KH | DFCI |
| RALY | BC103753.1 | 32.6 | Splicing | Baltz/Castello | RRM | DFCI |
| RALYL | BC031090.1 | 32.3 | Other | Castello | RRM | DFCI |
| RALYL | HQ447147 | 32.3 | Other | Castello | RRM | DNASU |
| RAN | BC014518.2, BC014901.2, BC016654.1, BC051908.2 | 24.4 | Localization | Baltz/Castello | Other | DFCI |
| RBBP6 | BC029352.1 | 13.2 | Other | Baltz | zf-CCHC | DNASU |
| RBBP6 | BC172357 | 201.6 | Other | Baltz | zf-CCHC | DNASU |
| RBFOX1 | BC113691.1 | 42.4 | Localization | | RRM | DFCI |
| RBFOX2 | BC025281.1 | 40.4 | Splicing | Baltz/Castello | RRM | DFCI |
| RBFQX2 | BC013115.1 | 37.9 | Splicing | Baltz/Castello | RRM | DFCI |
| RBFOX3 | RBFOX3 | 33.9 | Splicing | | RRM | In-house |
| RBM10 | BC004181.2, BC008733.2, BC024153.2 | 103.5 | Stability | Baltz/Castello | RRM | DFCI |
| RBM11 | BC030196.1 | 32.2 | Splicing | | RRM | DFCI |
| RBM12 | BC012787.2, BC013981.2 | 97.4 | Other | Castello | RRM | DFCI |
| RBM12B | BC039260.1 | 87.4 | Other | Baltz/Castello | RRM | DFCI |
| RBM14 | BC000488.2 | 69.5 | Other | Baltz/Castello | RRM | DFCI |
| RBM15 | BC103493.1 | 106.4 | Other | Baltz/Castello | RRM | DFCI |
| RBM15B | BC139836.1 | 63.1 | Splicing | Baltz/Castello | RRM | DFCI |
| RBM17 | BC039322.1 | 46.0 | Splicing | | RRM | DFCI |
| RBM18 | BC008942.2 | 21.8 | Other | | RRM | DFCI |
| RBM19 | BC004289.1, BC006137.1 | 107.3 | Other | Baltz/Castello | RRM | DFCI |
| RBM22 | AL136933 | 46.9 | Splicing | Baltz/Castello | RRM | DNASU |
| RBM23 | BC002586.2 | 46.8 | Other | | RRM | DFCI |
| RBM24 | BC104810.1 | 19.8 | Stability | | RRM | DFCI |
| RBM25 | BC136775.1 | 100.2 | Splicing | Baltz/Castello | RRM | DFCI |
| RBM26 | BC000791.2 | 7.3 | Other | Baltz/Castello | RRM | DFCI |
| RBM26 | BC111697.1 | 111.0 | Other | Baltz/Castello | RRM | DFCI |
| RBM26 | BC041655.1 | 110.7 | Other | Baltz/Castello | RRM | DFCI |
| RBM28 | BC013889.2 | 85.7 | Splicing | Baltz/Castello | RRM | DFCI |
| RBM3 | BC006825.1 | 17.2 | Translation | Baltz/Castello | RRM | DFCI |
| RBM33 | BC011923.2 | 30.2 | Other | Baltz/Castello | RRM | DFCI |
| RBM34 | BC029451.1 | 48.1 | Other | Baltz/Castello | RRM | DFCI |
| RBM38 | BC018711 | 23.4 | Stability | Baltz/Castello | RRM | DNASU |
| RBM4 | BC021120.1 | 20.0 | Splicing | Baltz/Castello | RRM | DFCI |
| RBM4 | BC032735.1 | 40.3 | Splicing | Baltz/Castello | RRM | DFCI |
| RBM41 | BC006986 | 47.1 | Other | | RRM | DNASU |
| RBM42 | BC002868.2 | 47.4 | Other | Castello | RRM | DFCI |
| RBM42 | BC004204.2 | 50.4 | Other | Castello | RRM | DFCI |
| RBM43 | BC136411.1 | 40.7 | Other | | RRM | DNASU |
| RBM45 | BC086549.1 | 53.3 | Other | Baltz/Castello | RRM | DFCI |
| RBM46 | BC028588.2 | 60.0 | Other | | RRM | DFCI |
| RBM47 | BC126261.1 | 64.1 | Other | Baltz/Castello | RRM | DFCI |
| RBM48 | BC003503.1, BC004951.1 | 40.1 | Translation | Baltz/Castello | RRM | DNASU |
| RBM5 | BC002957.1 | 81.5 | Splicing | Baltz | RRM | DFCI |
| RBM6 | BC046643.1 | 69.2 | Other | Baltz/Castello | RRM | DFCI |
| RBM7 | BC034381.1 | 30.5 | Other | Baltz/Castello | RRM | DFCI |
| RSM8A | GQ0120283 | 19.9 | Stability | Baltz | RRM | DNASU |
| RBMS1 | BC085192.1, BC080620.1 | 6.7 | Other | Baltz/Castello | RRM | DFCI |
| RBMS1 | BC018951.2 | 44.5 | Other | Baltz/Castello | RRM | DFCI |
| RBMS2 | BC027863.1 | 44.0 | Other | Baltz/Castello | RRM | DFCI |
| RBMX | BC006550.2 | 42.3 | Splicing | Baltz/Castello | RRM | DFCI |
| RBMX2 | BC033750.1 | 37.3 | Other | Castello | RRM | DFCI |

TABLE 1-continued

| Gene symbol | Accession number | MW (kDa) | GO Term | Group | Domain | Source |
|---|---|---|---|---|---|---|
| RBMX2 | BC125126.1 | 74.0 | Other | Castello | RRM | DNASU |
| RBMY1A1 | X76059 | 40.7 | Splicing | | RRM | DNASU |
| RBMY1A1 | BC070298.1 | 51.3 | Splicing | | RRM | DNASU |
| RBMY1F | BC030018.2 | 55.7 | Splicing | | RRM | DFCI |
| RBPMS | BC003608.2 | 24.3 | Other | Caatello | RRM | DFCI |
| RC3H2 | BC044642.1 | 56.9 | Other | Baltz/Castello | RRM | DFCI |
| RDBP | BC025235.1, BC050617.2 | 43.2 | Other | Castello | Other | DFCI |
| RDX | BC047109.1 | 68.6 | Ottrer | Castello | Other | DFCI |
| REPIN1 | BC001760.1 | 63.6 | Other | Castello | Zn-Finger | DFCI |
| REXO4 | BC009274.2 | 46.7 | Other | Baltz/Castello | Other | DFCI |
| REXO5 | BC007646 | 86.9 | Other | | Other | In-house |
| RNMTL1 | BC050614.1 | 47.0 | Other | Baltz/Castello | Other | DFCI |
| RNMTL1 | BC011550.1 | 47.0 | Other | Baltz/Castello | Other | DFCI |
| RNPC3 | BC010697.1 | 30.1 | Splicing | | RRM | DFCI |
| RNPS1 | BC001659.2 | 34.2 | Stability | Baltz/Castello | RRM | DFCI |
| RPGR | BC031624.1 | 52.6 | Other | Castello | Other | DFCI |
| RPL10A | BC006791.1, BC011366.1 | 24.8 | Stability | Baltz/Castello | Ribosomal | DFCI |
| RPL13A | BC000514.2, BC001675.2, BC065236.1 | 23.6 | Stability | Castello | Ribosomal | DFCI |
| RPL13A | BC070223.1 | 23.6 | Stability | Castello | Ribosomal | DFCI |
| RPL14 | BC005134.2 | 23.9 | Stability | Baltz/Castello | Ribosomal | DFCI |
| RPL14 | BC009294.2 | 23.6 | Stability | Baltz/Castello | Ribosomal | DFCI |
| RPL15 | BC014837.1 | 24.1 | Stability | Baltz/Castello | Ribosomal | DFCI |
| RPL15 | BC071672.1 | 24.1 | Stability | Baltz/Castello | Ribosomal | DFCI |
| RPL15 | BC081585.1 | 16.7 | Stability | Baltz/Castello | Ribosomal | DFCI |
| RPL18A | BC066319.1 | 20.8 | Stability | Baltz/Castello | Ribosomal | DFCI |
| RPL19 | BC000530.2, BC013016.2 | 23.5 | Stability | Castello | Ribosomal | DFCI |
| RPL21 | BC091603.1, BC007505.2, BC071902.1 | 18.6 | Stability | Baltz/Castello | Ribosomal | DFCI |
| RPL22 | BC058887.1 | 14.8 | Stability | Baltz/Castello | Ribosomal | DFCI |
| RPL23 | BC010114.2 | 14.9 | Stability | Castello | Ribosomal | DFCI |
| RPL23 | BC062716.1 | 14.9 | Stability | Castello | Ribosomal | DFCI |
| RPL23A | BC014459.1 | 17.7 | Stability | Baltz/Castello | Ribosomal | DFCI |
| RPL27 | BC001700.2, BC002588.2, BC007273.1, BC010026.2 | 15.8 | Stability | Baltz/Castello | Ribosomal | DFCI |
| RPL28 | BC010173.2, BC011582.1 | 15.7 | Stability | Castello | Ribosomal | DFCI |
| RPL23 | BC010182.2 | 15.8 | Stability | Castello | Ribosomal | DFCI |
| RPL3 | BC004323.1 | 26.8 | Stability | Baltz/Castello | Ribosomal | DFCI |
| RPL3 | BC006483.1, BC008003.1, BC012786.2, BC014017.2, BC063662.1 | 48.1 | Stability | Baltz/Castello | Ribosomal | DFCI |
| RPL30 | BC032700.2 | 12.8 | Stability | Baltz/Castello | Ribosomal | DFCI |
| RPL31 | BC017343.2 | 14.5 | Stability | Castello | Ribosomal | DFCI |
| RPL32 | BC011514.1 | 15.9 | Stability | Castello | Ribosomal | DFCI |
| RPL35 | BC010918.1 | 14.6 | Stability | Castello | Ribosomal | DFCI |
| RPL35 | BC000348.2 | 14.6 | Stability | Castello | Ribosomal | DFCI |
| RPL35A | BC001037.2, BC010949.1, BC017093.1, BC081890.1 | 12.5 | Stability | Baltz/Castello | Ribosomal | DFCI |
| RPL36 | BC004971.1 | 12.3 | Stability | Castello | Ribosomal | DFCI |
| RPU | BC001365.2, BC005817.2, BC007748.2, BC007996.1, BC009888.2, BC010151.2, BC014653.1, BC068925.1 | 47.7 | Stability | Baltz/Castello | Ribosomal | DFCI |
| RPL5 | BC001882.1 | 12.1 | Stability | Baltz/Castello | Ribosomal | DFCI |
| RPL6 | BC004138.2, BC032299.1 | 32.7 | Stability | Castello | Ribosomal | DFCI |
| RPL6 | BC022444.1 | 32.7 | Stability | Castello | Ribosomal | DFCI |
| RPL7 | BC006095.1, BC008850.2, BC009599.1 | 29.2 | Stability | Baltz/Castello | Ribosomal | DFCI |
| RPL7L1 | BC073890.1 | 28.7 | Other | Baltz/Castello | Ribosomal | DFCI |
| RPL8 | BC00077.2 | 28.0 | Stability | Baltz/Castello | Ribosomal | DFCI |

TABLE 1-continued

| Gene symbol | Accession number | MW (kDa) | GO Term | Group | Domain | Source |
|---|---|---|---|---|---|---|
| RPL8 | BC012197.1, BC013104.1 | 28.0 | Stability | Baltz/Castello | Ribosomal | DFCI |
| RPLP0 | BC000087.2, BC008092.1, BC008594.1, BC009867.2, BC015173.1, BC015690.1 | 34.3 | Stability | Baltz/Castello | Ribosomal | DFCI |
| RPLP0 | BC000345.2, BC000752.2, BC003655.2 | 34.3 | Stability | Baltz/Castello | Ribosomal | DFCI |
| RPN1 | BC010839.1 | 68.6 | Other | Castello | Other | DFCI |
| RPP21 | BC011730.2 | 17.6 | Other | | Other | DFCI |
| RPP25 | BC002497.2, BC007270.1 | 20.6 | Other | Castello | Other | DFCI |
| RPP30 | BC006991.1 | 29.3 | Other | Castello | Other | DFCI |
| RPS10 | BC001032.2, BC001955.1, BC005012.1 | 18.9 | Stability | Baltz/Castello | Other | DFCI |
| RPS11 | BC007283.1, BC007603.1, BC007945.2, BC010028.2, BC016378.1 | | | | | |
| RPS15A | BC001697.2 | 14.8 | Stability | Baltz/Castello | Ribosomal | DFCI |
| RPS15A | BC030569.1, BC048113.1 | 14.8 | Stability | Baltz/Castello | Ribosomal | DFCI |
| RPS19BP1 | BC037573.1, BC047711.1 | 15.4 | Other | Baltz/Castello | Other | DFCI |
| RPS2 | BC018178.1 | 31.3 | Stability | Baltz/Castello | Ribosomal | DFCI |
| RPS2 | BC001795.1, BC008862.2, BC010165.2, BC016951.2, BC021545.1, BC023354.1 | 31.3 | Stability | Baltz/Castello | Ribosomal | DFCI |
| RPS20 | BC007507.2 | 13.4 | Stability | Baltz/Castello | Ribosomal | DFCI |
| RPS21 | BC027976.1 | 7.1 | Stability | Castello | Ribosomal | DFCI |
| RPS24 | BC000523.2 | 15.1 | Stability | Baltz/Castello | Ribosomal | DFCI |
| RPS28 | BC000354.1, BC021239.2 | 7.8 | Stability | Baltz/Castello | Ribosomal | DFCI |
| RPS3 | BC003137.1, BC034149.1 | 26.7 | Stability | Baltz/Castello | KH | DFCI |
| RPS3A | BC000204.1, BC001708.1, BC004981.1, BC006298.2, BC009219.2, BC009404.2, BC017123.2, BC019072.2, BC030161.2 | 29.9 | Stability | Baltz/Castello | Ribosomal | DFCI |
| RPS4X | BC007308.1 | 22.2 | Stability | Baltz/Castello | Ribosomal | DFCI |
| RPS4X | BC100903.1 | 29.6 | Stability | Baltz/Castello | Ribosomal | DFCI |
| RPS6 | BC013296.2 | 28.7 | Stability | Castello | Ribosomal | DFCI |
| RPS6 | BC027620.1 | 28.7 | Stability | Castello | Ribosomal | DFCI |
| RPS7 | BC002886.2, BC061901.1 | 22.1 | Stability | Baltz/Castello | Ribosomal | DFCI |
| RPS8 | BC070875.1 | 24.2 | Stability | Baltz/Castello | Ribosomal | DFCI |
| RPUSD3 | BC065741.1 | 37.6 | Modification | Baltz/Castello | Other | DFCI |
| RPUSD3 | BC032135.2 | 37.5 | Modification | Baltz/Castello | Other | DFCI |
| RPUSD4 | BC014131.2 | 42.2 | Modification | Baltz/Castello | Other | DFCI |
| RRP36 | BC011933.2 | 29.8 | Other | Baltz/Castello | Other | DFCI |
| RRP7A | BC073834.1, BC121118.1 | 32.3 | Other | Castello | RRM | DFCI |
| RRP8 | BC001071.2 | 50.7 | Other | Baltz/Castello | Other | DFCI |
| RRS1 | BC001811.2, BC013043.2 | 41.2 | Other | Baltz/Castello | Other | DFCI |
| RSL1D1 | BC113899.1 | 55.0 | Other | Baltz/Castello | Ribosomal | DFCI |
| RSRC1 | HQ448170 | 38.7 | Splicing | | Other | DNASU |
| RTCA | BC012804.1 | 40.7 | Other | | Other | DFCI |
| RTN4 | BC016165.1 | 42.3 | Other | Castello | Other | DFCI |
| RTN4 | BC012619.1 | 40.3 | Other | Castello | Other | DFCI |
| RY1 | BC017890.1 | 18.9 | Other | | Other | DNASU |
| S100A4 | BC018300.1 | 11.7 | Other | Castello | Other | DFCI |
| SAFB2 | BC025279.1 | 57.2 | Other | Baltz/Castello | RRM | DFCI |
| SAMD4A | BC057836.1 | 27.6 | Translation | Castello | SAM | DFCI |
| SAMD4A | BC121173.1 | 70.0 | Translation | Castello | SAM | DFCI |

TABLE 1-continued

| Gene symbol | Accession number | MW (kDa) | GO Term | Group | Domain | Source |
|---|---|---|---|---|---|---|
| SAMSN1 | BC029112.1 | 41.7 | Other | Castsllo | Other | DFCI |
| SARNP | BC007099.1 | 23.7 | Translation | Baltz/Castello | Other | DFCI |
| SART3 | BC111883.1 | 109.9 | Other | Baltz/Castello | RRM | DFCI |
| SBDS | BC065700.1 | 28.8 | Other | Castello | Other | DFCI |
| SCAF8 | BC070071.1 | 140.5 | Splicing | | RRM | DFCI |
| SCD5 | BC004936.1 | 14.3 | Other | | Other | DFCI |
| SCD5 | | 14.3 | Other | | Other | DNASU |
| SCG3 | BC014539.1 | 53.0 | Other | Castello | Other | DFCI |
| SEC61B | BC001734.1 | 10.0 | Other | Cassette | Other | DFCI |
| SEC63 | BC048287.1 | 88.0 | Other | Castello | Other | DFCI |
| SEC63 | BC047221.1 | 88.0 | Other | Castello | Other | DFCI |
| SECISBP2 | BC001189.1 | 95.5 | Translation | Castello | Ribosomal | DFCI |
| SECP43 | | 32.5 | Other | | Other | In-house |
| SENP5 | BC030705 | 86.7 | Other | | Other | In-house |
| SERBP1 | BC020555.1 | 44.3 | Stability | Baltz/Castello | Other | DFCI |
| SERBP1 | BC002488.2 | 44.2 | Stability | Baltz/Castello | Other | DFCI |
| SERBP1 | BC003049.1, BC008045.2, BC019273.1, BC026918.1 | 45.0 | Stability | Baltz/Castello | Other | DFCI |
| SERPINH1 | BC014623 | 46.4 | Other | Castello | Other | DNASU |
| SF1 | BC008080.2, BC020217.1 | 59.7 | Splicing | Baltz/Castello | KH | DFCI |
| SF3A1 | BC001976.1, BC097684.2 | 88.9 | Splicing | Baltz/Castello | Other | DFCI |
| SF3A2 | BC004434 | 49.3 | Splicing | Baltz/Castello | Zn-finger | DNASU |
| SF3A3 | BC011523 | 58.8 | Splicing | Baltz/Castello | Other | DNASU |
| SF3B14 | BC015413 | 13.6 | Splicing | Baltz | RRM | In-house |
| SF3B14 | BC016483.1 | 14.6 | Splicing | Baltz | RRM | DNASU |
| SF3B2 | BC007610.1 | 72.6 | Splicing | Baltz/Castello | Other | DFCI |
| SF3B3 | JF432652 | 30.2 | Splicing | | Other | DNASU |
| SF3B3 | BC009463.1 | 44.8 | Splicing | | Other | DNASU |
| SF3B4 | BC004273.1, BC013886.2 | 44.4 | Splicing | Baltz/Castello | RRM | DFCI |
| SFPQ | BC051192.1 | 76.2 | Splicing | Baltz/Castello | RRM | DFCI |
| SFRS10 | BC000160 | 33.7 | Other | | Other | DNASU |
| SFRS13A | HQ448699 | 22.2 | Other | | Other | DNASU |
| SFRS16 | BC013178.1 | 23.3 | Other | | Other | DNASU |
| SFRS17A | BC028151.1 | 51.5 | Other | | Other | DNASU |
| SFRS17A | BC110496.1 | 80.7 | Other | | Other | DNASU |
| SFRS2IP | NM_004719 | 164.7 | Other | | Other | DNASU |
| SFSWAP | BC136678.1 | 104.8 | Splicing | | Other | DFCI |
| SKIV2L | BC015758 | 137.8 | Other | | DEAD | DNASU |
| SKIV2L2 | BC028604.2 | 117.8 | Splicing | Castello | DEAD | DFCI |
| SLBP | BC014908.1, BC015703.1 | 31.3 | Localization | Castello | Other | DFCI |
| SLC25A5 | BC058160.1 | 32.9 | Other | Castello | Other | DFCI |
| SLC3A2 | BC001061.2, BC003000.1 | 57.9 | Other | Castello | Other | DFCI |
| SLC7A9 | BC017962.1 | 53.5 | Other | | Other | DFCI |
| SLIRP | BC017895.1 | 12.3 | Other | Baltz | RRM | DFCI |
| SLU7 | BC010634.1 | 68.3 | Splicing | | Other | DNASU |
| SMG6 | BC148373 | 57.3 | Stability | | Other | DNASU |
| SMN1 | BC015308 | 31.8 | Other | | Other | DNASU |
| SMN1 | BC000908 | 30.4 | Other | | Other | DNASU |
| SMNDC1 | BC011234.1 | 26.7 | Splicing | Castello | Other | DFCI |
| SNIPI | BC027040.1 | 45.8 | Other | Castello | Other | DFCI |
| SNRNP35 | BC009622.1 | 30.0 | Splicing | | RRM | DFCI |
| SNRNP40 | BC001494.2 | 39.3 | Splicing | Castello | Other | DFCI |
| SNRNP70 | BC001315.1 | 51.6 | Splicing | Baltz/Castello | RRM | DFCI |
| SNRPA | BC000405.2, BC008290.1 | 31.3 | Splicing | Baltz | RRM | DFCI |
| SNRPB | BC080516.1 | 23.7 | Splicing | Baltz | LSM | DFCI |
| SNRPB2 | BC018022.1, BC038737.2 | 25.5 | Splicing | | RRM | DFCI |
| SNRPD2 | BC000488.2 | 13.5 | Splicing | Castello | LSM | DFCI |
| SNRPE | BC002639.2 | 10.8 | Splicing | | LSM | DFCI |
| SNRPF | BC063397.1, BC128453.1 | 9.7 | Splicing | | LSM | DFCI |
| SNRPG | BC000070.2, BC022432.1, BC086302.1 | 8.5 | Splicing | Castello | LSM | DFCI |
| SNRPN | BC003180.1, BC010057.1, BC024777.1, BC025178.1 | 24.6 | Splicing | | LSM | DFCI |
| SNURF | BC024777.1 | 24.6 | Other | | Other | DNASU |
| SNW1 | BC108903.1 | 81.6 | Splicing | Baltz | Other | DNASU |

TABLE 1-continued

| Gene symbol | Accession number | MW (kDa) | GO Term | Group | Domain | Source |
|---|---|---|---|---|---|---|
| SOX21 | BC111584 | 28.6 | Other | | Other | DNASU |
| SPATS2 | BC048299.1 | 59.5 | Other | Castello | Other | DFCI |
| SPATS2L | BC018738.1 | 64.0 | Other | Baltz/Castello | Other | DFCI |
| SR140 | BC111692.1 | 72.5 | Other | | Other | DNASU |
| SRBD1 | BC032538.1 | 69.7 | Other | | S1 | DFCI |
| SREK1 | BC067770.1, BC112343.1 | 69.4 | Splicing | Baltz | RRM | DFCI |
| SRFBP1 | BC031222.1 | 48.6 | Other | Baltz/Castello | Other | DFCI |
| SRP14 | BC030495.2 | 14.6 | Translation | Baltz/Castello | Other | DFCI |
| SRP68 | BC020238.1 | 67.3 | Translation | Castello | Other | DFCI |
| SRPK2 | BC035214.1 | 77.6 | Splicing | Baltz/Castello | Other | DFCI |
| SRPK2 | BC068547.1 | 77.6 | Splicing | Baltz/Castello | Other | DFCI |
| SRPR | BC001162.1, BC009110.1, BC013583.1 | 69.8 | Translation | Castello | Other | DFCI |
| SRPR | BC008077.2 | 63.2 | Translation | Castello | Other | DFCI |
| SRSF1 | BC010264.1 | 27.7 | Localization | Baltz/Castello | RRM | DFCI |
| SRSF10 | BC001107.1 | 22.2 | Localization | Baltz | RRM | DFCI |
| SRSF10 | BC005039.1 | 31.3 | Localization | Baltz | RRM | DFCI |
| SRSF11 | BC040436.1 | 53.4 | Localization | Castello | RRM | DFCI |
| SRSF12 | BC021715.1 | 30.5 | Splicing | Baltz | RRM | DFCI |
| SRSF2 | BC066958.1 | 19.4 | Localization | Castello | RRM | DFCI |
| SRSF3 | BC000914.1, BC069018.1 | 19.3 | Localization | Baltz/Castello | RRM | DFCI |
| SRSF4 | BC002781.2 | 56.7 | Localization | Castello | RRM | DFCI |
| SRSF5 | BC018823.2 | 31.3 | Localization | Castello | RRM | DFCI |
| SRSF6 | BC006832.2 | 39.6 | Localization | Castello | RRM | DFCI |
| SRSF7 | BC000997.2, BC017369.2, BC022328.1 | 27.4 | Localization | Castello | RRM | DFCI |
| SRSF8 | BC057783.1 | 31.4 | Other | Bahz/Castello | RRM | DFCI |
| SRSF9 | BC093971.1 | 25.5 | Localization | Castello | RRM | DFCI |
| SSBP1 | BC000895.1 | 17.3 | Other | Baltz/Castello | Other | DFCI |
| SSRP1 | BC005116.1 | 81.1 | Other | Baltz/Castello | Other | DFCI |
| STAU1 | BC050432.1 | 63.2 | Localization | Baltz | dsRBD | DFCI |
| STAU2 | BC008370.1 | 11.8 | Other | Baltz/Castello | dsRBD | DFCI |
| STAU2 | BC110447.1 | 52.8 | Other | Baltz/Castello | dsRSD | DFCI |
| STAU2 | BC008369.1 | 59.0 | Other | Baltz/Castello | dsRBD | DFCI |
| STIP1 | BC002987.1 | 62.6 | Other | Castello | Other | DFCI |
| STRBP | BC017732.1 | 73.7 | Other | Baltz/Castello | dsRBD | DFCI |
| STXBP1 | BC015749.1 | 67.6 | Other | Castello | Other | DFCI |
| SUCLG1 | BC000504.2 | 35.0 | Other | Castello | Other | DFCI |
| SUGP1 | BC142988.1 | 72.5 | Splicing | | G-patch | DFCI |
| SUGP2 | BC020586.1 | 110.4 | Splicing | Baltz/Castello | G-patch | DFCI |
| SUMO1 | BC006462.1, BC053528.1 | 11.8 | Other | Castello | Other | DFCI |
| SUMO1 | BC066308.1 | 11.5 | Other | Castello | Other | DFCI |
| SUPT5H | BC024203.2 | 121.0 | Other | Baltz/Castello | Other | DFCI |
| SUPV3L1 | BC036112.1 | 88.0 | Other | Baltz/Castello | Other | DFCI |
| SURF6 | BC014878.1 | 41.5 | Other | Baltz/Castello | Other | DFCI |
| SYF2 | BC010882.1 | 28.7 | Splicing | Baltz/Castello | Other | DFCI |
| SYMPK | BC006567 | 126.6 | Other | | Other | DNASU |
| SYNCRIP | BC032843.1 | 58.7 | Stability | Baltz/Castello | RRM | DFCI |
| TAF15 | BC046099.1 | 81.8 | Other | Baltz/Castello | RRM | DFCI |
| TAF15 | TAF15(1) | 61.8 | Other | | Other | In-house |
| TAfl5 | TAF15(5) | 61.3 | Other | | Other | In-house |
| TARDBP | BC001487 | 29.5 | Stability | Baltz/Castello | RRM | In-house |
| TARDBP | BC095435 | 44.9 | Stability | Baltz/Castello | RRM | DNASU |
| TBRG4 | BC014918.1, BC017235.2 | 70.7 | Other | Baltz/Castello | Other | DFCI |
| TCOF1 | | 96.8 | Other | Baltz/Castello | Other | DNASU |
| TDRD3 | BC030514.1 | 73.2 | Other | Baltz/Castello | Other | DFCI |
| TDRD9 | BC128057.1 | 99.5 | Other | | DEAD | DFCI |
| TDRKH | BC032890.1 | 82.1 | Other | | KH | DFCI |
| TEFM | BC024328.1 | 26.3 | Other | Baltz | Other | DFCI |
| TERT | BC172541 | 125.7 | Other | | Other | DNASU |
| TES | BC001451.1 | 48.0 | Other | Castello | Other | DFCI |
| TFB1M | BC017788.1 | 39.5 | Modification | Castello | Other | DFCI |
| TFIP11 | BC011599.2 | 96.8 | Splicing | | G-patch | DFCI |
| THOC1 | BC010381 | 75.7 | Localization | | Other | DNASU |
| THOC3 | BC006849 | 38.8 | Localization | | Other | DNASU |
| THOC4 | BC052302.1 | 27.6 | Other | Baltz/Castello | Other | DNASU |
| THOC5 | CU013430 | 78.5 | Localization | | Other | DNASU |
| THOC6 | | 37.5 | Localization | | Other | DNASU |
| THRAP3 | BC112330.1 | 108.7 | Stability | Baltz/Castello | Other | DFCI |
| THUMPD1 | BC000448.2 | 39.3 | Other | Castello | Other | DFCI |
| TIA1 | BC015944 | 24.1 | Splicing | Baltz/Castello | RRM | In-house |
| TIAL1 | BC030025.1 | 27.9 | Other | Baltz/Castello | RRM | DFCI |

TABLE 1-continued

| Gene symbol | Accession number | MW (kDa) | GO Term | Group | Domain | Source |
|---|---|---|---|---|---|---|
| TOB1 | DQ893993 | 38.1 | Other | | Other | DNASU |
| TOB2 | BC038957 | 36.6 | Other | | Other | DNASU |
| TOE1 | JF432161 | 56.5 | Other | | Other | DNASU |
| TOE1 | | 56.5 | Other | | Other | In-house |
| TOP3B | BC002432.2 | 96.7 | Other | Baltz/Castello | Other | DFCI |
| TPD52L2 | BC008804.1 | 22.2 | Other | Castello | Other | DFCI |
| TFT1 | BC022436.1 | 15.6 | Other | Castello | Other | DFCI |
| TPT1 | BC003352.2, BC052333.1 | 19.6 | Other | Castello | Other | DFCI |
| TRA2A | BC017094.2 | 32.7 | Splicing | Baltz/Castello | RRM | DFCI |
| TRAP1 | BC018950.2 | 80.1 | Other | Castello | Other | DFCI |
| TRIM39 | BC034985.1 | 56.4 | Other | | Other | DFCI |
| TRIM39 | BC097661.2 | 56.4 | Other | | Other | DFCI |
| TRIM56 | BC048194.1 | 81.5 | Other | Baltz/Castello | Zn-Finger | DFCI |
| TRIP6 | BC004999.1, BC028985.1 | 50.3 | Other | Castello | Other | DFCI |
| TRIP6 | BC002680.2 | 50.1 | Other | Castello | Other | DFCI |
| TRMT10C | BC035967.1 | 46.7 | Other | | tRNA | DFCI |
| TRMT1L | BC045535.1 | 81.7 | Other | Castello | Other | DFCI |
| TRMT2A | BC013352.2, BC017184.2 | 68.7 | Modification | Castello | RRM | DFCI |
| TRMT6 | BC001262.1 | 55.8 | Translation | Castello | Other | DFCI |
| TRMU | BC080631.1 | 25.2 | Other | | tRNA | DFCI |
| TRNAU1AP | BC039879.1 | 26.4 | Other | Baltz/Castello | RRM | DFCI |
| TRNAU1AP | BC000680.2 | 32.5 | Other | Baltz/Castello | RRM | DFCI |
| TROVE2 | BC038658.2 | 60.7 | Other | | Other | DFCI |
| TRUB2 | BC001457.2 | 36.7 | Modification | Baltz/Castello | Other | DFCI |
| TSR1 | BC125110.1 | 91.8 | Other | Castello | Other | DFCI |
| TSR1 | BC019090.2 | 75.0 | Other | Castello | Other | DFCI |
| TTYH1 | BC019358 | 49.1 | Other | | Other | In-house |
| TUFM | BC001633.1, BC010041.2 | 49.9 | Translation | Castello | Other | DFCI |
| TUT1 | BC005013.1 | 57.9 | Other | | RRM | DFCI |
| TUT2 | uc010jaf.1 | 56.0 | Other | | Other | In-house |
| TUT3 | uc010vgo.2 | 75.8 | Other | | Other | In-house |
| TUT5 | uc003jdx.1 | 59.9 | Other | | Other | In-house |
| TUT7 | uc004aoq.3 | 171.2 | Other | | Other | In-house |
| TWF2 | BC016452.1 | 39.5 | Other | Castello | Other | DFCI |
| U2AF1 | BC001177.1, BC001923.1 | 27.9 | Localization | Baltz/Castello | RRM | DFCI |
| U2AF1 | BC005915.1 | 19.8 | Localization | Baltz/Castello | RRM | DFCI |
| U2AF1L4 | BC021186.1 | 22.0 | Splicing | | RRM | DNASU |
| U2AF2 | BC008740.2 | 53.1 | Localization | Baltz/Castello | RRM | DFCI |
| UBAP2L | BC003170.1 | 114.5 | Other | Baltz/Castello | Other | DFCI |
| UBE2I | BC000427.2, BC051289.1 | 18.0 | Other | Castello | Other | DFCI |
| UCHL5 | BC015521.1 | 37.5 | Other | Castello | Other | DFCI |
| USO1 | BC032654.1 | 107.8 | Other | Castello | Other | DFCI |
| USF32 | BC054344.1 | 44.7 | Other | | Other | DFCI |
| USP36 | BC038983.1 | 31.8 | Other | Castello | Other | DFCI |
| UTP11L | BC005182.1 | 30.4 | Other | Baltz/Castello | Other | DFCI |
| UTP14A | BC001149.1, BC009649.1, BC014987.1 | 88.0 | Other | Baltz/Castello | Other | DFCI |
| UTP15 | BC013064.1 | 32.4 | Other | Baltz/Castello | Other | DFCI |
| UTP23 | BC006955.1, BC022441.1 | 28.4 | Other | Castello | Other | DFCI |
| UTP3 | BC004546.1 | 54.6 | Other | Baltz/Castello | Other | DFCI |
| WBSCR16 | BC007823 | 49.9 | Other | Baltz/Castello | Other | DNASU |
| WDR3 | BC058836.1 | 43 | Other | Castello | Other | DFCI |
| WDR33 | BC013990.2 | 38.3 | Other | Baltz | Other | DNASU |
| WDR36 | BC133025.1 | 105.3 | Other | Castello | Other | DFCI |
| WDR6 | BC002826.2 | 32.1 | Other | Castello | Other | DFCI |
| XPO1 | BC032847.2 | 123.4 | Localization | | Other | DFCI |
| XPO5 | BC000129.1 | 31.5 | Other | Baltz/Castello | Other | DFCI |
| XPO5 | BC009969.2 | 75.8 | Other | Baltz/Castello | Other | DFCI |
| XRCC6 | BC008343.1, BC012154.2 | 69.8 | Other | Baltz/Castello | Other | DFCI |
| XRCC6 | BC010034.2, BC018259.2 | 69.8 | Other | Baltz/Castello | Other | DFCI |
| XRN1 | NM_019001 | 194.1 | Stability | Baltz/Castello | Other | DNASU |
| XRN2 | BC006417.1 | 63.8 | Other | Baltz/Castello | Other | DFCI |
| YARS | BC001933.1, BC016689.1 | 59.1 | Translation | Castello | tRNA | DFCI |
| YTHDC1 | BC041119.1 | 84.7 | Splicing | Baltz/Castello | Other | DFCI |
| YTHDF1 | BC050284.1 | 60.9 | Other | Baltz/Castello | Other | DFCI |
| YTHDF2 | BC002559.2 | 82.3 | Other | Baltz/Castello | Other | DFCI |
| YTHDF3 | BC052970.1 | 63.9 | Other | Baltz/Castello | Other | DFCI |

TABLE 1-continued

| Gene symbol | Accession number | MW (kDa) | GO Term | Group | Domain | Source |
|---|---|---|---|---|---|---|
| YWHAE | BC000179.1, BC001440 | 29.2 | Other | Castello | Other | DNASU |
| YWHAG | BC020963.2 | 28.3 | Other | | Other | DFCI |
| ZC3H11A | BC014268.2 | 89.1 | Localization | Baltz/Castello | ZnF-CCCH | DFCI |
| ZC3H14 | BC027807.2 | 34.9 | Other | Baltz/Castello | ZnF-CCCH | DFCI |
| ZC3H18 | BC050463.1 | 106.4 | Other | Castello | ZnF-CCCH | DFCI |
| ZC3H7A | BC012575.1 | 19.8 | Other | Baltz/Castello | ZnF-CCCH | DFCI |
| ZC3H8 | BC032001.1 | 34.3 | Other | Baltz/Castello | ZnF-CCCH | DFCI |
| ZC3HAV1 | BC040956.1 | 77.9 | Other | Baltz/Castello | Other | DFCI |
| ZCCHC11 | | 81.1 | Other | | Other | In-house |
| ZCCHC11 | | 81.1 | Other | | Other | In-house |
| ZCCHC11 | | 81.1 | Other | | Other | In-house |
| ZCCHC11 | BC131734.1 | 185.3 | Other | Baltz/Castello | zf-CCHC | DFCI |
| ZCCHC17 | BC007446.2, BC050609.1 | 27.6 | Other | Baltz/Castello | S1 | DFCI |
| ZCCHC6 | AL832026 | 144.5 | Other | Baltz/Castello | zf-CCHC | DNASU |
| ZCCHC7 | BC034022.1 | 34.5 | Other | Castello | zf-CCHC | DFCI |
| ZCCHC7 | BC036940.1 | 62.9 | Other | Castello | zf-CCHC | DFCI |
| ZCCHC9 | BC014841.1 | 30.9 | Other | Castello | zf-CCHC | DFCI |
| ZCRB1 | BC022543.1 | 24.6 | Splicing | Baltz/Castello | RRM | DFCI |
| ZFC3H1 | BC073843.1 | 37.8 | Other | Castello | Zn-Finger | DFCI |
| ZFC3H1 | BC015679.2 | 39.1 | Other | Castello | Zn-Finger | DFCI |
| ZFP36 (TTP) | BC009693 | 34.0 | Other | | Other | In-house |
| ZFP36L1 | BC018340.1 | 36.3 | Stability | Castello | ZnF-CCCH | DFCI |
| ZFP36L2 | BC005010 | 51.6 | Stability | Castello | ZnF-CCCH | DNASU |
| ZGPAT | BC019338.1 | 54.7 | Other | | ZnF-CCCH | DFCI |
| ZMAT3 | BC002896.2 | 32.1 | Other | Castello | Zn-Finger | DFCI |
| ZNF9 | NM_003418 | 19.5 | Other | | Other | DNASU |
| ZRANB2 | BC039814.1 | 36.2 | Splicing | Baltz/Castello | Zn-Finger | DFCI |
| ZRSR1 | BC113599.1 | 67.6 | Other | | RRM | DFCI |
| ZRSR2 | BC113454.1, BC113480.1 | 58.0 | Splicing | | RRM | DFCI |
| ZRSR2 | BC050451.11 | 58.0 | Splicing | | RRM | DFCI |
| ZYX | BC003743.2, BC009360.2, BC010031.2 | 61.3 | Other | Castello | Other | DFCI |
| AC004381.6 | AC004381.6 (LOC81691 exonuclease NEF-sp) | 88.9 | Other | | Other | In-house |

Figures 1D, 1E, 1F:
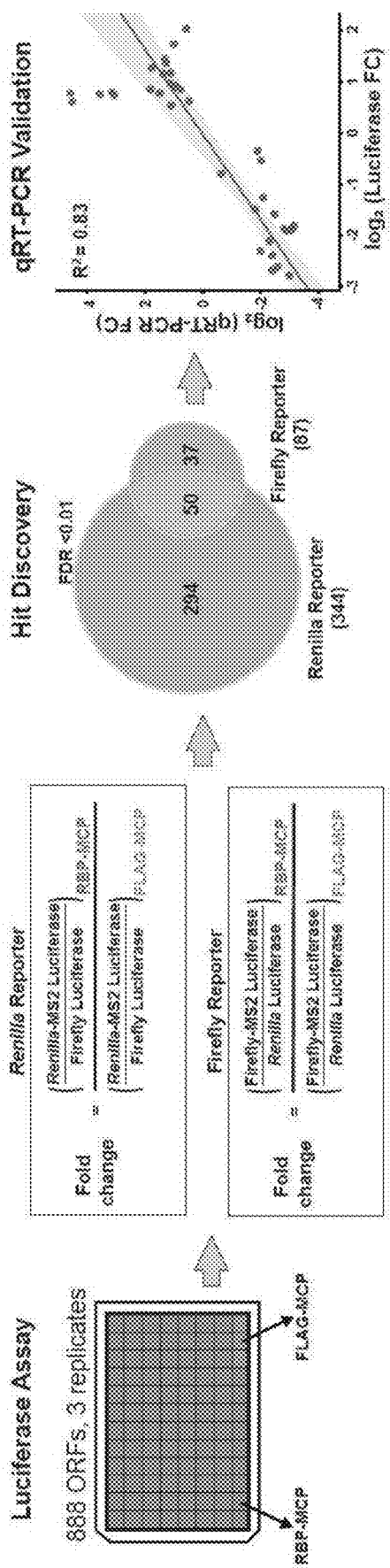
FIG. 1D shows an exemplary experimental and analysis workflow. The screen was conducted on 888 MCP-tagged RBPs in two reporter contexts. Levels of MS2-tagged luciferase reporters were normalized to untagged co-transfected controls reporters. The effect of RBP recruitment was calculated as the ratio of normalized luciferase levels in the presence of MCP-tagged RBPs relative to that of MCP-FLAG control.
FIG. 1E shows hit discovery, wherein RBPs with effects at estimated FDR <0.01 in both reporter assays were considered candidate regulators.
FIG. 1F shows qPCR validation of reporter levels for 35 candidate RBP regulators. Means (n=3 independent measurements) of log 2-transformed fold-changes of reporter mRNA levels, calculated analogously to FIG. 1D, were plotted against the corresponding log 2-transformed fold-changes of reporter luciferase levels. The line represents the least-squares linear regression fit. Shaded areas denote the 95% confidence interval. $R^2$, Pearson correlation coefficient.
Figure 7D:
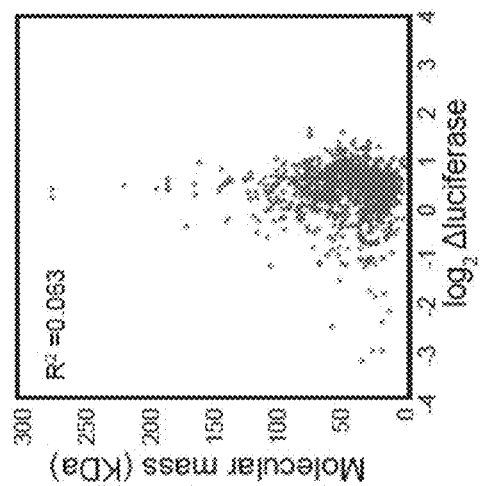
FIG. 7D shows a scatter plot of luciferase effect and RBP size.
Figure 7E:
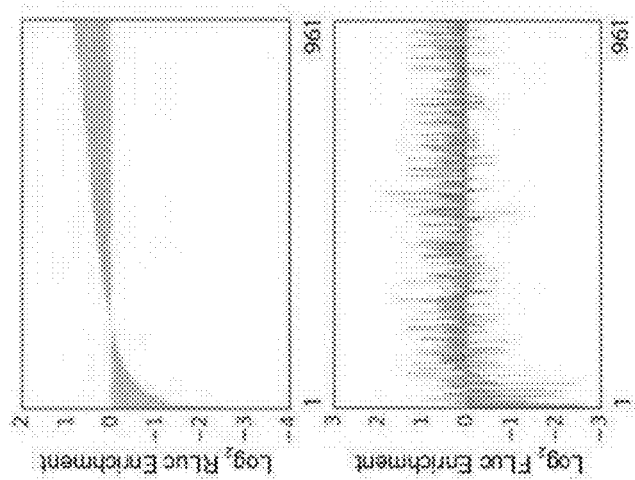
FIG. 7E shows luciferase activities from two different reporter constructs. Bar graphs showing log 2-fold changes of the activity of Renilla (top) or firefly (bottom) luciferase reporters in. presence of the MS2-fusion ORFs over FLAG control. Each vertical line represents a tethered ORF.
Figure 7F:
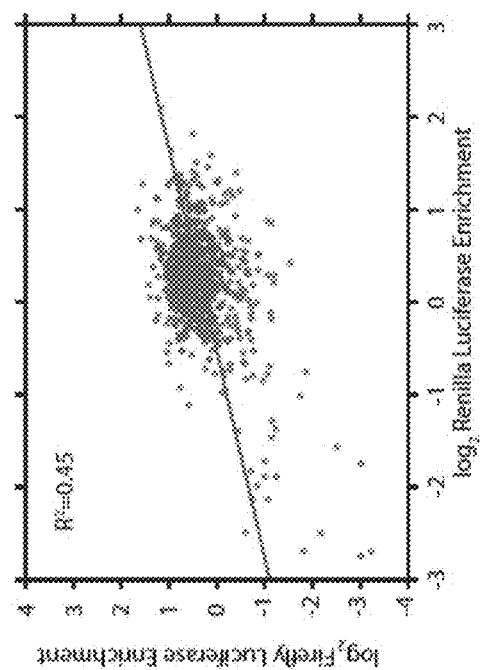
FIG. 7F shows a scatter plot of luciferase activities from the two reporter constructs.

Example 2—Large-Scale Tethered Function Screen Assigns RBPs to Roles in RNA Stability and Translation 961 ORFs, representing 888 RBPs, were screened in triplicate. Two dual luciferase reporter systems were used as described above, and the FLAG expression construct was used as a negative control (FIG. 1D, left). The effect of RBP recruitment to the tethering reporter was calculated as the fold change in luciferase activity relative to FLAG control, after normalization of each to the untethered reporter (FIG. 1D, right). Supporting the validity of the screening approach, it was confirmed that the effect was not correlated with RBP size, indicating that steric hindrance is unlikely to account for these observations (FIG. 7D). The magnitude of the effect on reporter transcript abundance generally depended on the reporter systems (FIG. 7E) but for 97% of ORFs (961), both reporter systems agreed on the direction of regulation (FIG. 7F), indicating high reproducibility.

Figure 1G:
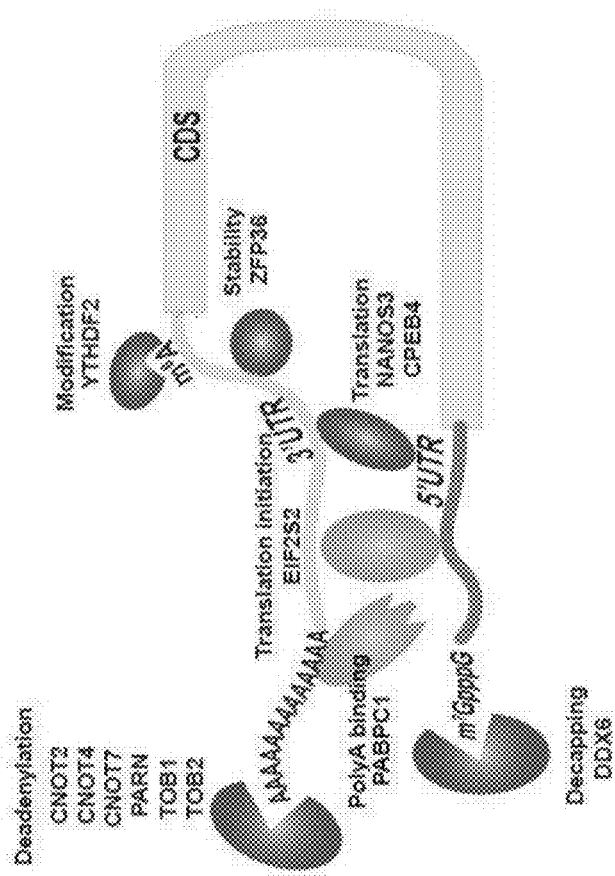
FIG. 1G shows examples of our 50 candidate RBP regulators that are known to affect RNA stability and translation.

Candidates from each reporter assay were prioritized by using multiple t-tests at a threshold p<0.05 and calculated false discovery rates (FDR) for each comparison using the Benjamini, Krieger & Yekutieli procedure. 344 and 87 RBPs were identified with an estimated FDR <0.01 in *Renilla* and firefly reporters, respectively, of which 50 RBPs were recovered from both reporter contexts (FIG. 1E). In order to distinguish those RBPs that affect reporter mRNA stability from those regulating its translation, both luciferase transcripts were measured by reverse transcription quantitative PCR (rt-qPCR) for 35 RBPs of the 50 RBPs that significantly modulated luciferase activity in both reporter contexts. In general, the change in reporter translation levels was positively correlated with changes in reporter transcript levels (FIG. 1F). Among the strongest candidate negative regulators were RBP components of both deadenylation-dependent and -independent exonuclease decay pathways, including ZFP36, as well as members of the CCR4-NOT deadenylase complex (CNOT2, CNOT4, CNOT7, TOB1, and TOB2), the 3'-to-5' exonuclease PARN, and the decapping activator DDX6, which is recruited to the 5' cap via interaction with the CCR4-Not complex. As another positive control, it was also confirmed that YTHDF2, a member of the YTH domain family of N6-methyladenosine binding proteins, which recruit target RNAs to degradation bodies, exerts a negative effect on target mRNA levels. The results of the screen also confirmed several known negative regulators of translation, such as NANOS3 specific to germ cells, and CPEB4, which binds polyadenylation elements in the 3' UTR and negatively regulates translation initiation by interacting with the translation initiation factor eIF3. Interestingly, EIF2S2, with roles in promoting translation initiation, emerged as positive regulator of translation when recruited to the 3' UTR. It was speculated that recruitment of this protein to the 3' UTR brings it into proximity to the mRNA cap and 5'UTR, similar to DDX6 and CPEB4 and consistent with the closed-loop model of translation (FIG. 1G).

Figures 1H, 1I:
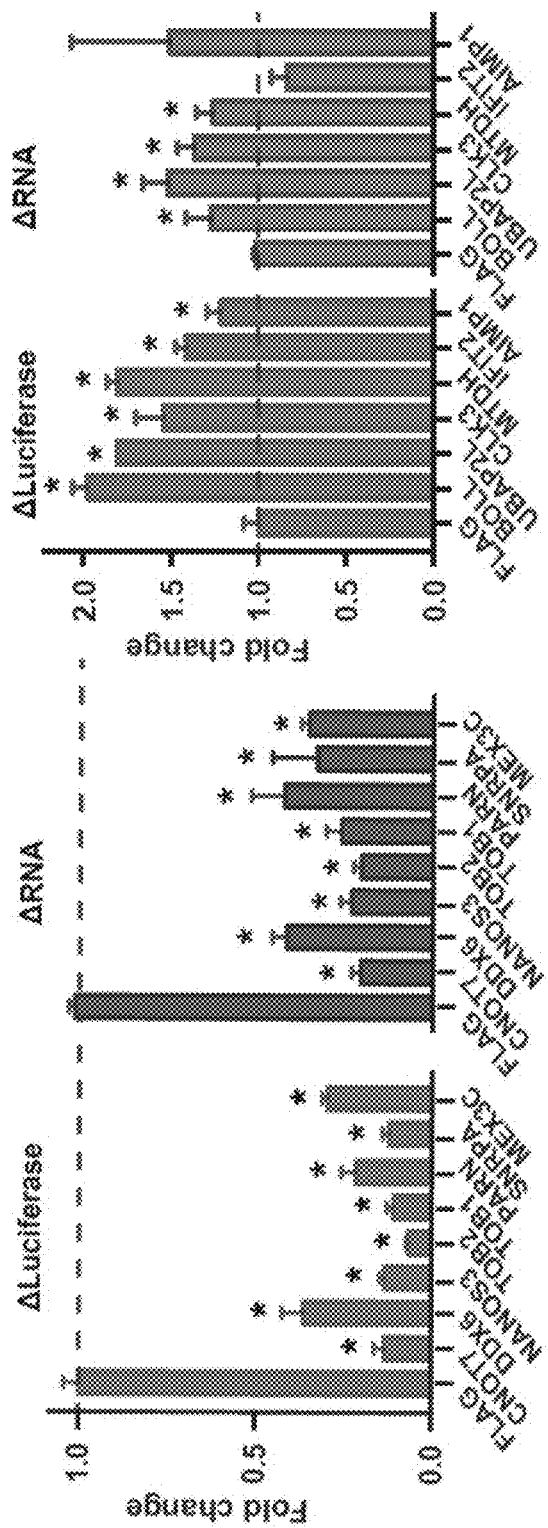
FIGS. 1H-1I shows validation of the FIG. 1H 9 negative and FIG. 1I 6 positive candidate regulators of RNA stability and/or translation by repeat luciferase and RT-PCR measurements. Values were calculated as in FIG. 1F. Error bars denote mean±SD for n=4 replicate transfections. *p<0.05 (two-tailed Student's t-test) vs. FLAG control.

To verify these RBPs hits are not false positive in the large screen assay, reporter protein and transcript level changes were re-confirmed by luciferase assay and qRT-PCR and chose 14 RBPs with significant effects (8 candidate stabilizers and 6 candidate destabilizers) for further investigation. Focus was put on RBPs with known roles in RNA stability and translation but where transcriptome-wide binding sites and preferences have not been described (e.g. CNOT7, DDX6, NANOS3, TOB1/2, MEX3C) and RBPs for which such roles are not known (e.g. UBAP2L, AIMP1, MTDH, IFTI2) (FIGS. 1H-1I).

Figure 1K:
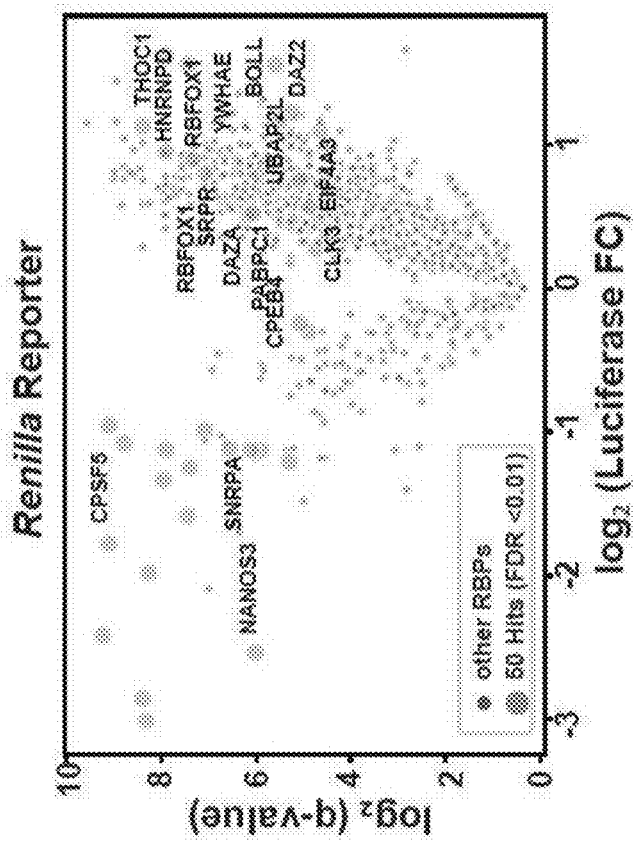
FIGS. 1J-1K shows volcano plots showing the distribution of fold changes for 50 RBP hits from the FIG. 1J Renilla and FIG. 1K firefly reporter assays.
Figure 1J:
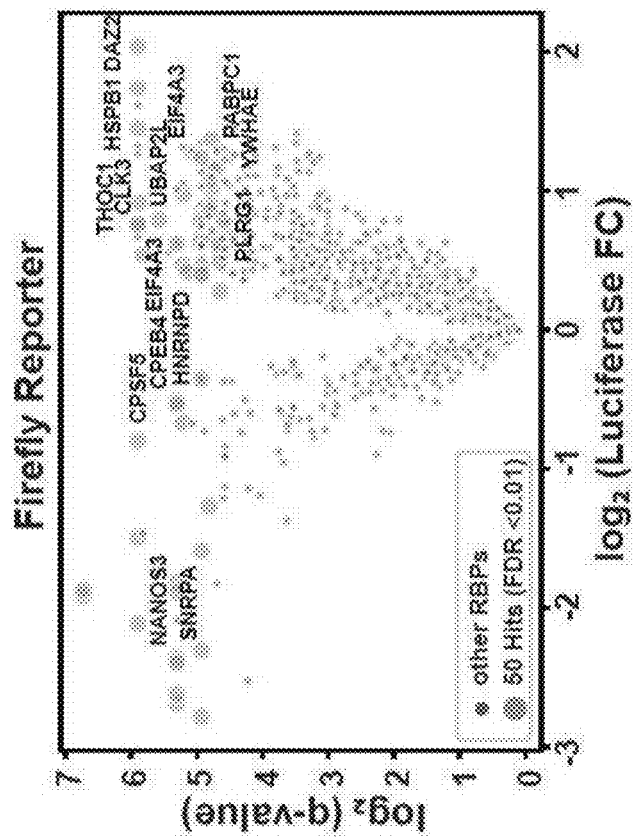
Figure 1L:
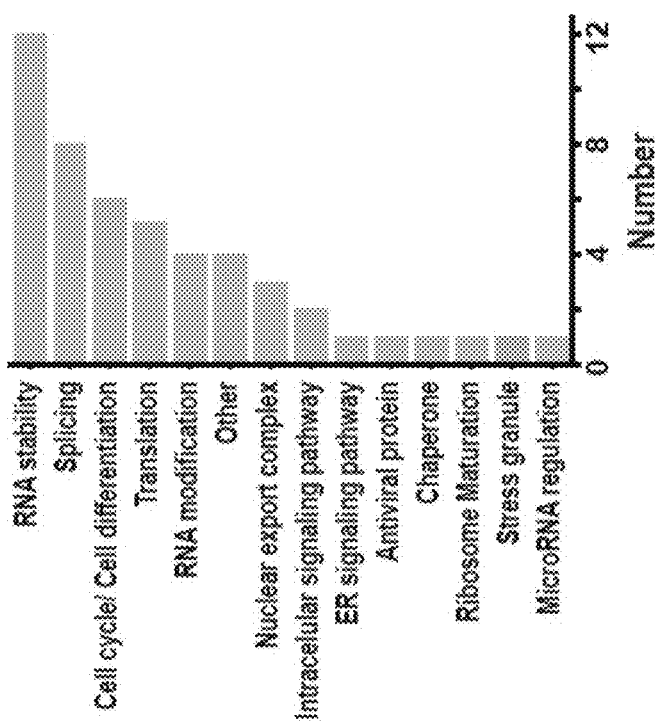
FIG. 1L shows classification of candidate RBP regulators by manual curation.

In summary, the screen revealed RBPs previously annotated to be implicated in metabolic processes, cell cycle, cell differentiation (BOLL, DAZ2, DAZ4, DAZAP1, NANOS3), stress granule regulators (UBAP2L), translation machinery (EIF2S2, LARP1, PABPC1, CPEB4), ER proteins (SRPR), and heat shock proteins (HSPB1). Eight annotated splicing factors (CLK3, CPSF5, PLRG1, PRPF3, RBFOX1, F3B3S, NRNP27, and SNRPA) and three nuclear export complex proteins (HNRNPD, THOC1, and YWHAE) were identified (FIGS. 1J-1L).

Figure 2A:
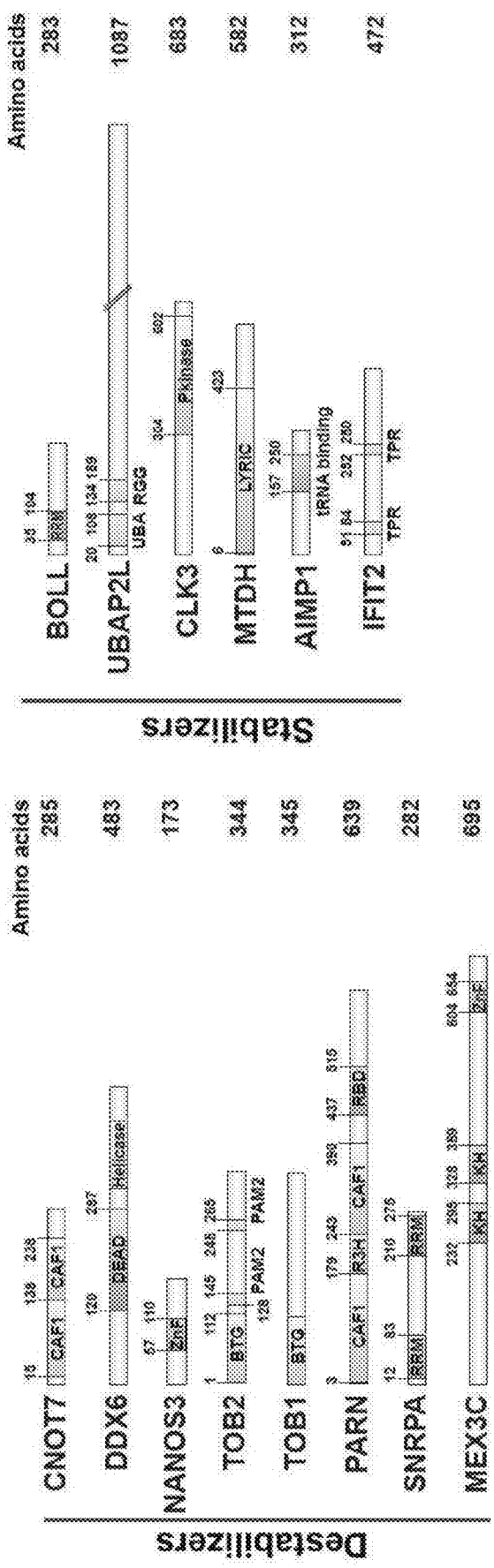
FIG. 2A shows domain structures of 14 candidate RBPs with RNA destabilizing (left) and stabilizing (right) effects in the tethering assay, with lengths of their polypeptide chains.
Figure 8A:
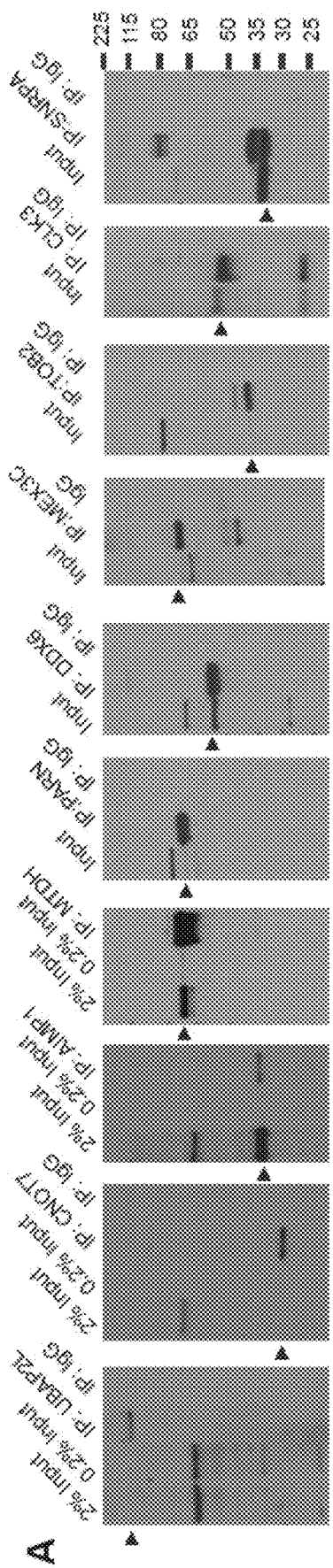
FIGS. 8A-8B show in-line western blots of eCLIP immunoprecipitations of candidate RBPs.
Figures 8B, 8C:
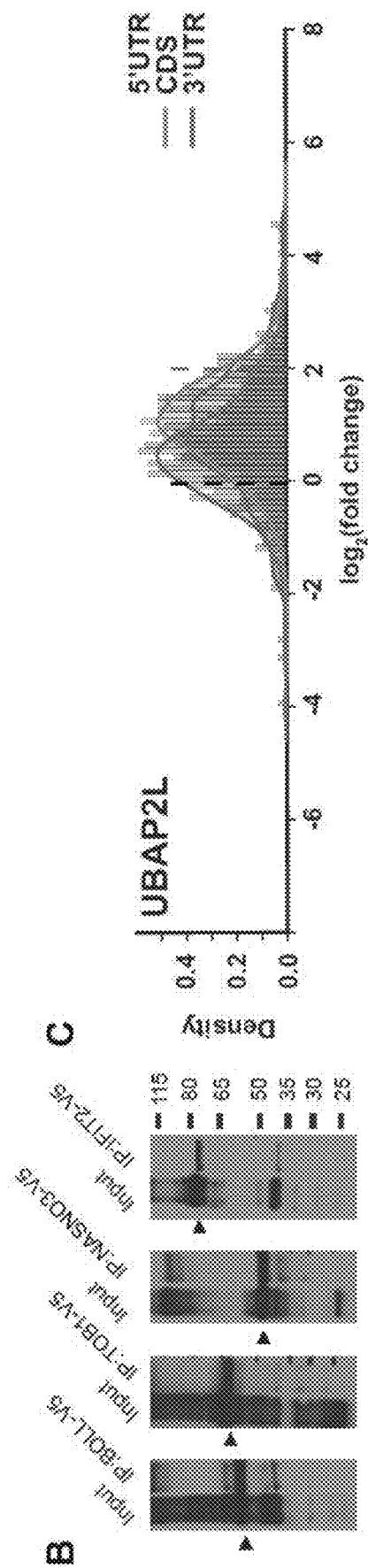
FIG. 8C shows histograms showing region-based fold-enrichment of read densities, normalized to paired SMInput controls for UBAP2L, which shows read density enrichment in CDS.

Example 3—Enhanced CLIP Identifies Endogenous RNA Targets of Candidate Stabilizers and Destabilizers In order to begin elucidating the physiological functions of candidate RBP regulators (FIG. 2A), their endogenous mRNA targets and their transcriptome-wide binding sites were investigated using enhanced cross-linking immunoprecipitation followed by sequencing (eCLIP). HEK293T cells were subjected to UV-crosslinking, lysis and RNA fragmentation, and protein-RNA complexes were immunoprecipitated using validated RBP-specific antibodies (FIG. 8A). Also, cells were transiently transfected with plasmids expressing V5-tagged fusions of those candidate RBPs which are not expressed in HEK293T cells or do not have RBP-specific antibodies (FIG. 8B). In total, eCLIP datasets for 14 candidate proteins were generated, each consisting of an RBP eCLIP (IP) library and a paired size-matched input (SMInput) library. Libraries were sequenced to at least 15M (million) reads (average of 24M), of which at least 1M (average of 5M) mapped uniquely to the human genome.

Figure 2B:
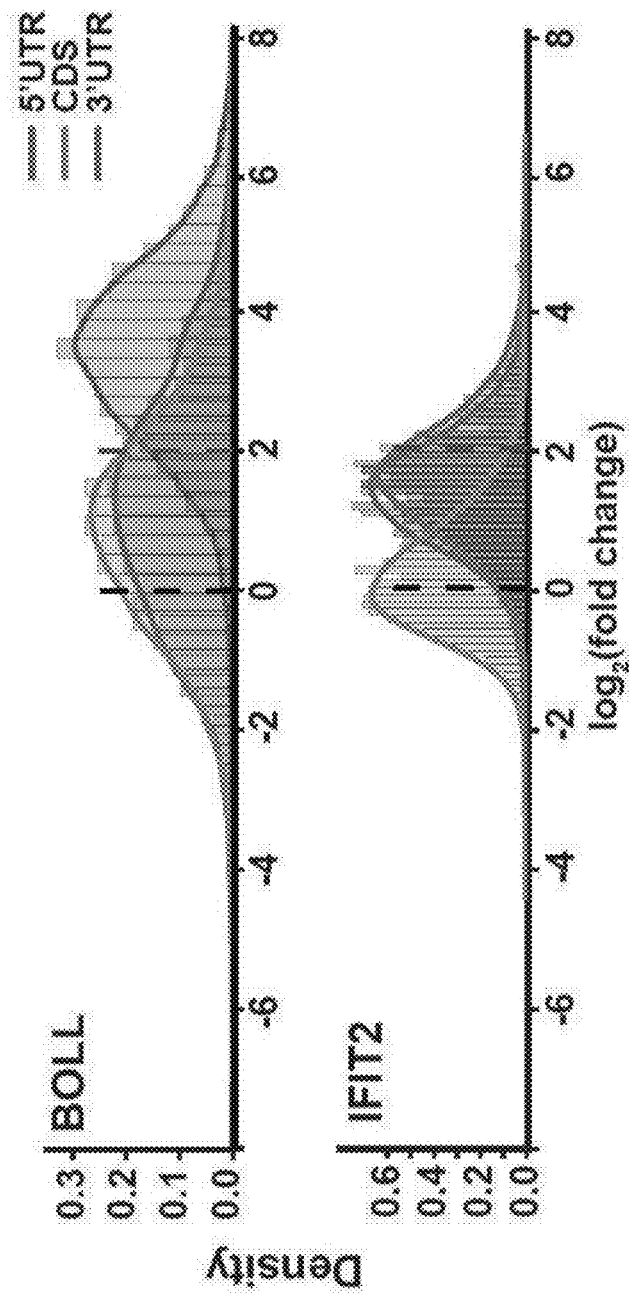
FIGS. 2B-2D show histograms showing region-based fold-enrichment of read densities, normalized to paired SMInput controls for (FIG. 2B) BOLL and IFIT2, which show read density enrichment in 3'UTRs.
Figure 2C:
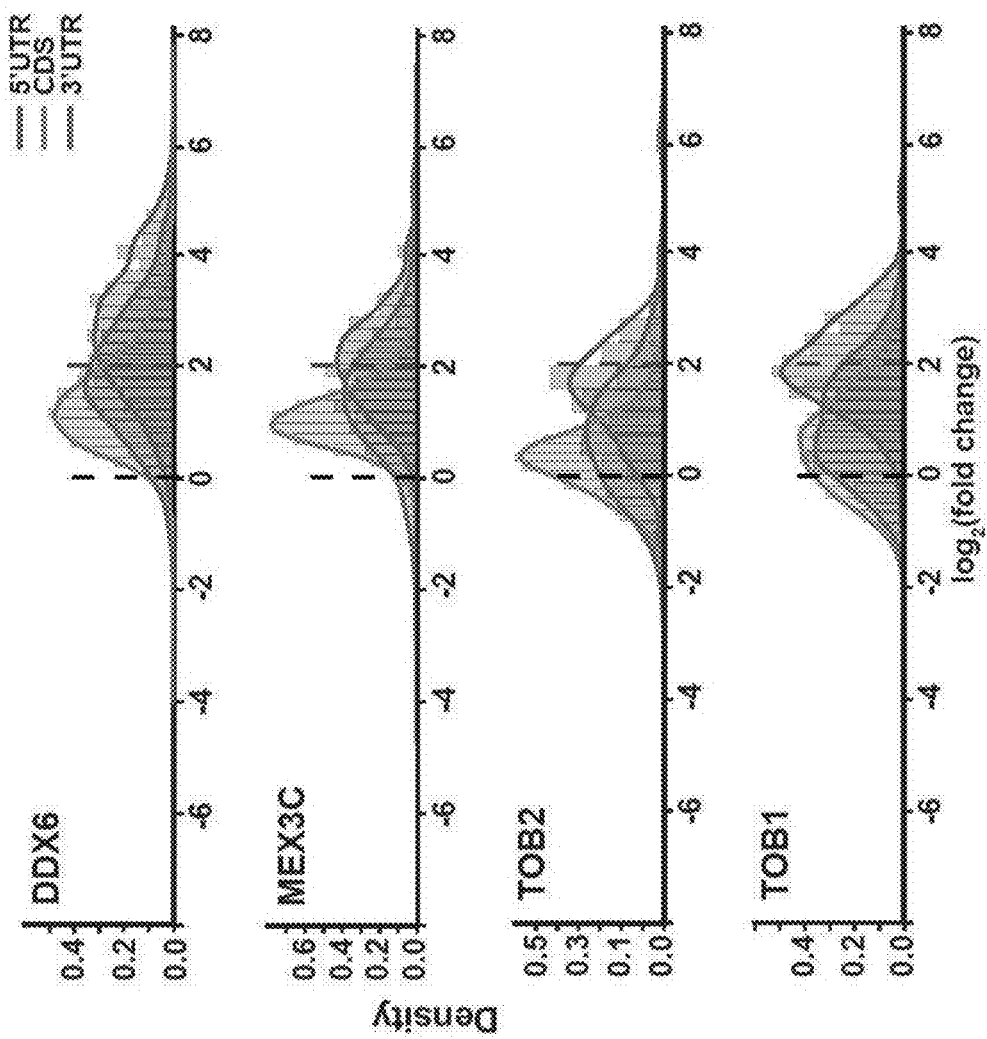
Figure 2D:
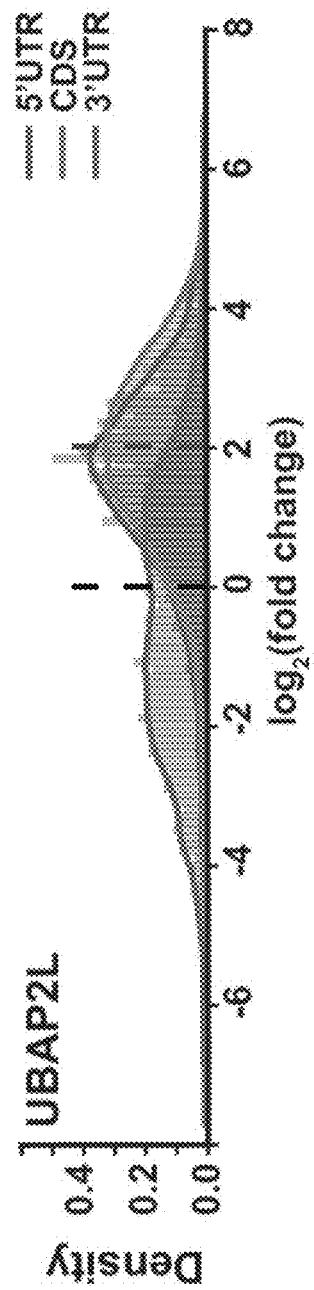

Next, transcript binding region specificities were determined using two distinct metrics, namely read density enrichment and binding cluster enrichment. Read density enrichment within 5' and 3'UTRs and coding regions (CDS) of annotated protein coding genes were computed by the fold enrichment in the IPs normalized to their paired SMInputs. To illustrate, BOLL, a germ-cell specific RBP with some documented roles in mRNA stabilization and translation enhancer activity, displayed a strong preference for 3'UTR association (FIG. 2B). Surprisingly, IFIT2 (Interferon Induced Protein With Tetratricopeptide Repeats 2), which is known to inhibit expression of viral messenger RNAs, robustly displays a strong 3'UTR preference in human mRNAs. The helicase DDX6 was enriched for binding within 5'UTRs, consistent with its role in the assembly of the decapping complex. A novel candidate 170 MEX3C, an RNA-binding E3 ubiquitin ligase that associates with the CCR4-NOT deadenylation complex to ubiquitinate CNOT7, unexpectedly exhibited preferential binding to 5'UTRs. Similarly, TOB family members TOB1 and TOB2, which recruit the catalytic subunits of the CCR4-NOT deadenylase complex to target mRNAs, showed a surprising preference for 5'UTRs, suggesting unexpected roles for this family of proteins (FIG. 2C). Distinct from all these RBPs, UBAP2L (Ubiquitin-associated protein 2-like) showed strong enrichment across exons, especially in CDS, and 5' UTR (FIG. 2D; FIG. 8C).

Figure 2E:
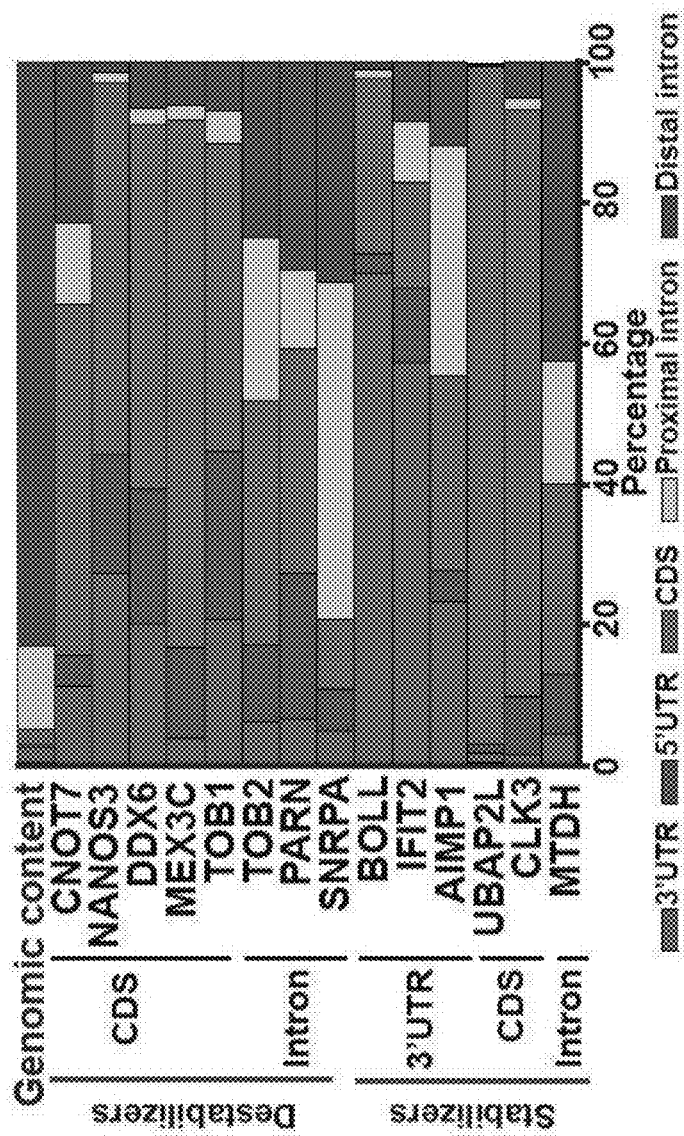
FIG. 2E shows bar graphs showing eCLIP binding cluster distribution across transcript regions for the 8 destabilizers and 6 stabilizers. Peak assignment was performed using stringent enrichment criteria (≥4-fold-enrichment and $p≤10^{-3}$ versus SMInput). The average region distribution of the entire transcriptome annotated in GENCODE v19 is indicated at the top.
Figure 2F:
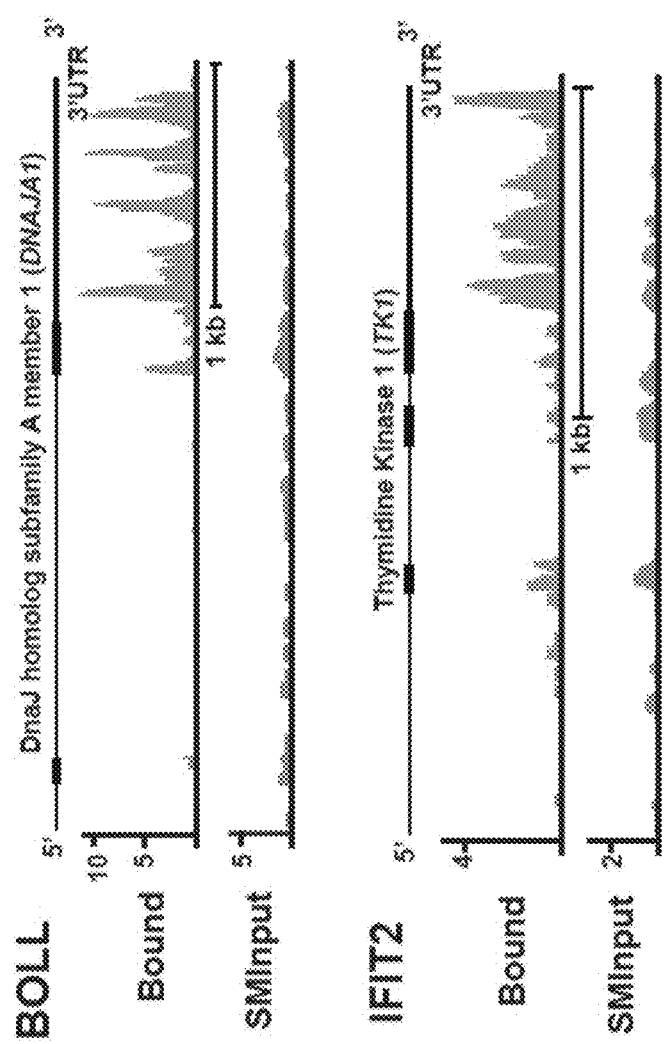
FIGS. 2F-2H show example genome browser track views of eCLIP read densities (in reads per million, RPM) and corresponding SMInput read densities for (FIG. 2F) BOLL and IFIT2, which show peak enrichment in 3'UTRs, (FIG. 2G) DDX6 and MEX3C, which show peak enrichment in 5'UTRs, and (FIG. 2H) UBAP2L, which shows peak enrichment across exons.
Figure 2G:
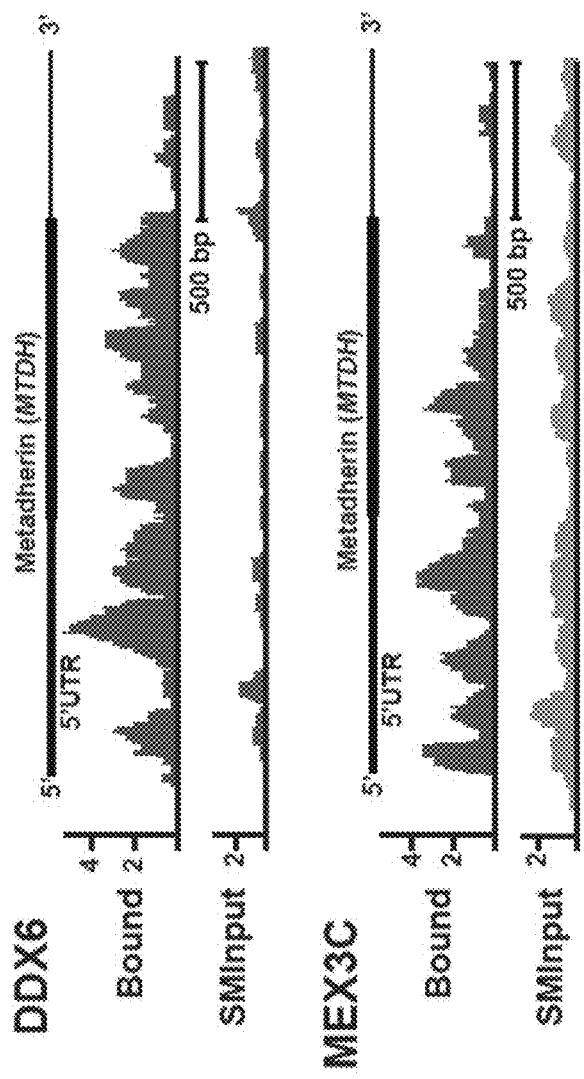
Figure 2H:
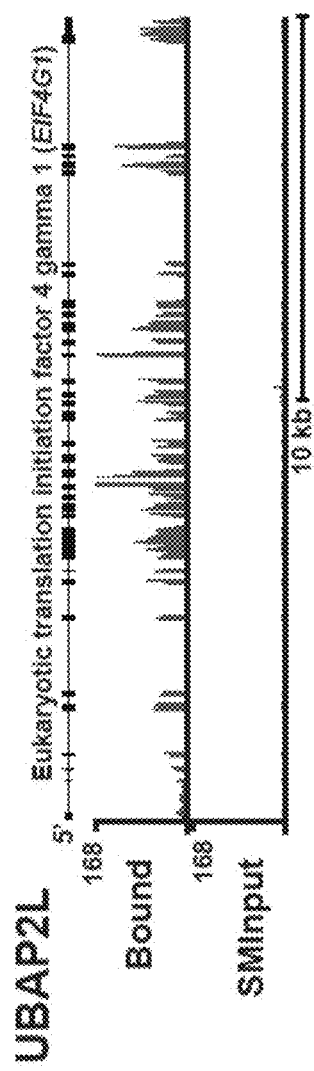
Figure 8D:
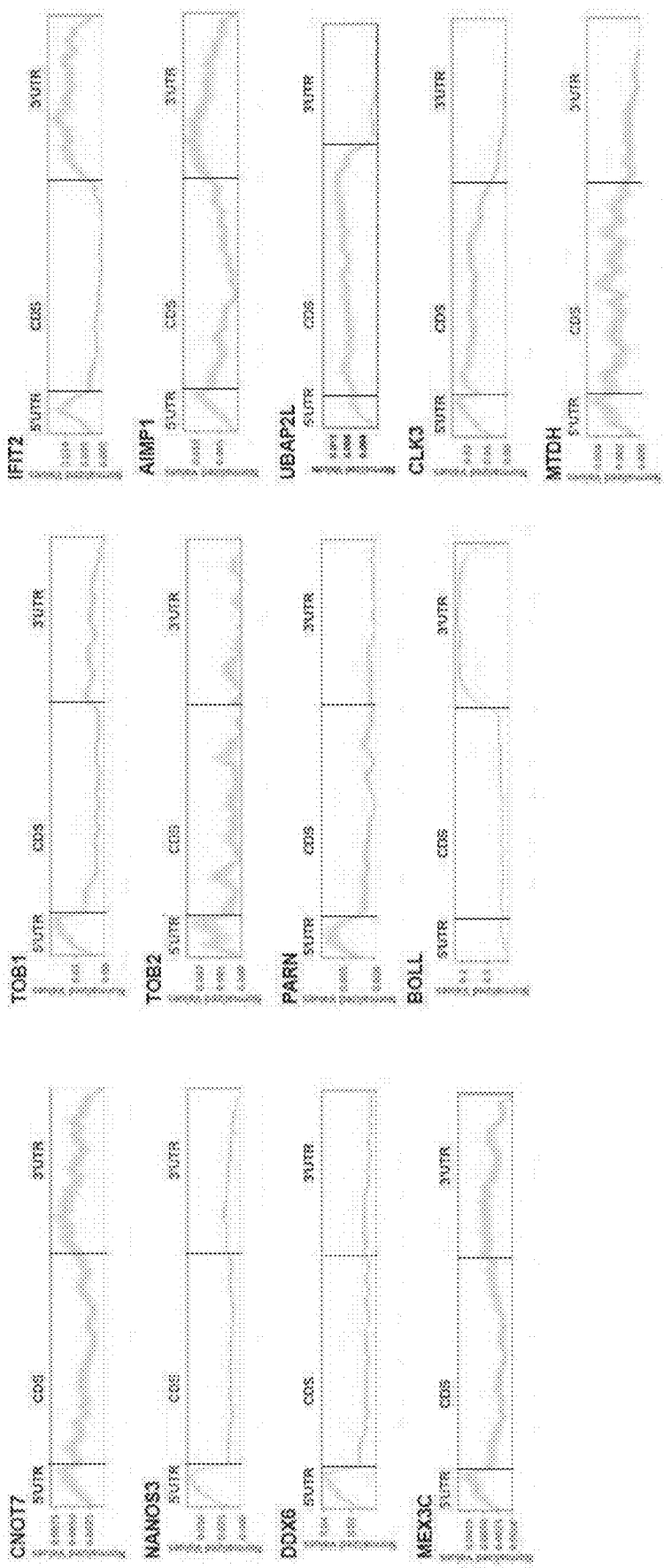
FIG. 8D shows metagene maps showing the distribution of eCLIP peak densities at target transcripts. Lines indicate the average number of significantly enriched peaks (4-fold-enriched and $p \leq 10^{-3}$ versus SMInput) across transcripts.
Figure 8F:
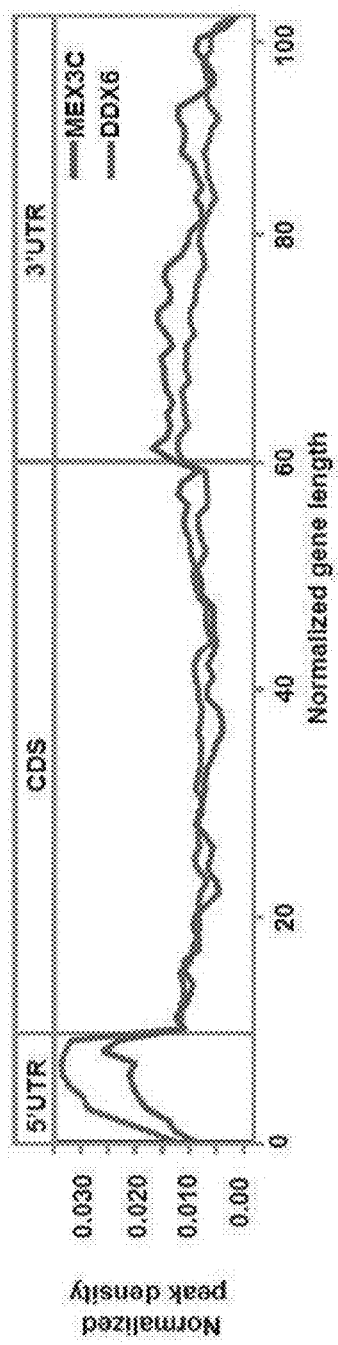
FIG. 8F shows a metagene map showing the distribution of DDX6 and MEX3C eCLIP peak densities at target transcripts. Lines indicate the average number of significantly enriched peaks ($\geq$4-fold-enriched and $p \leq 10^{-3}$ versus SMInput) across transcripts.
Figure 8E:
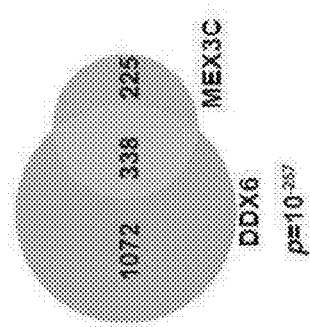
FIG. 8E shows a Venn diagram showing overlap in target transcripts between DDX6 and MEX3C in HEK293T cells.

To identify binding sites at higher resolution, binding clusters were discovered by the CLIPper algorithm. Cluster enrichment was computed by calculating the ratio of read densities between IPs and SMInputs within a cluster and significant clusters were defined as $p \leq 10^{-3}$ (Fisher's exact test for read numbers <5; $\chi^2$ test for read numbers $\geq 5$) and >4-fold enriched over SMInput. The significant clusters were generally located within the same enriched regions from the lower resolution gene region analysis (FIG. 2E; FIG. 8D). For example, the clusters for BOLL and IFIT2 were most enriched in 3'UTRs (FIG. 2F). Interestingly, DDX6's and MEX3C's target genes (FIG. 8E) and binding clusters (FIG. 2G; FIG. 8F) strongly overlap, suggesting that both proteins may be functionally linked and may act on the same mRNA targets. In contrast to the other candidate RBPs, the UBAP2L clusters were dispersed across exonic regions, rather than present as discrete binding sites (FIG. 2H). Overall, the analyses not only revealed previously unrecognized binding maps and preferences for RBPs known to affect mRNA stability and translation (CNOT7, DDX6), but also revealed novel RNA interactomes of candidate RBPs.

Figures 9A, 9B:
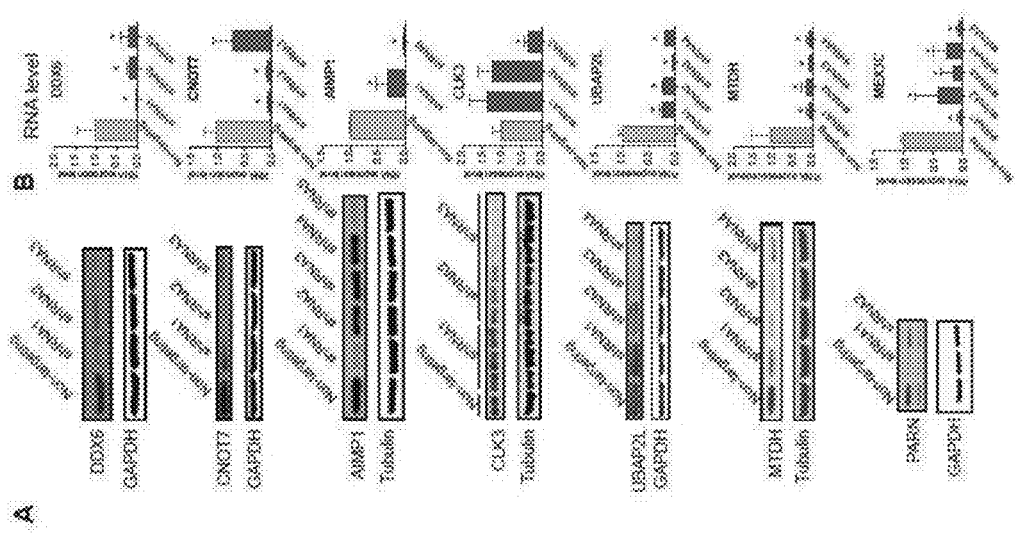
FIGS. 9A-9B show shRNA-mediated depletion of RBPs in HEK293T cells using 3-5 distinct shRNAs for each RBP, as indicated, compared to non-targeting shRNA control.
Figure 9C:
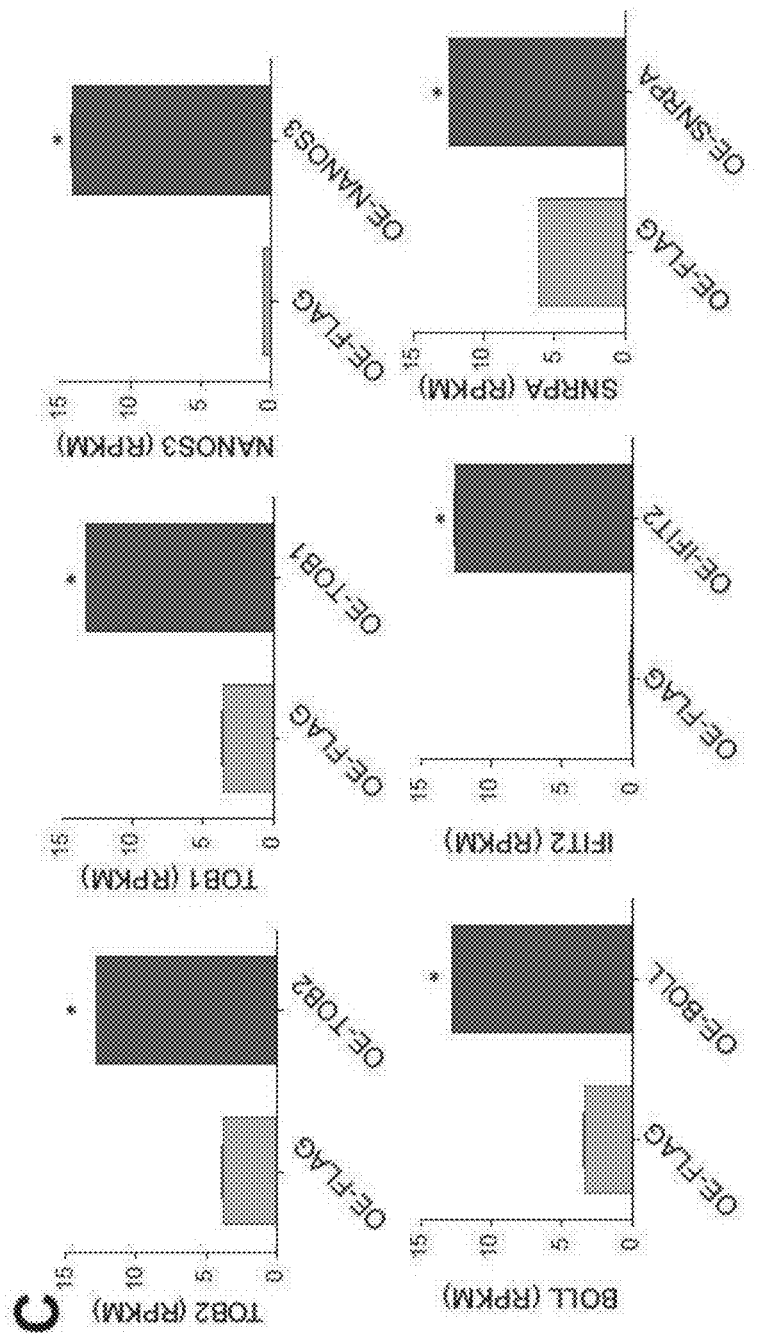
FIG. 9C shows overexpression of RBPs in HEK293T cells. Bar plots showing transcript levels (RPKM) for each RBP following transfection of RBP expression constructs or FLAG vector control.

Example 4—Integration of eCLIP and RNA-Seq Data Defines Regulatory Classes of RBPs and Transcripts To gain insight into how the candidate RBPs affect transcriptome-wide mRNA levels, they were depleted or exogenously expressed in HEK293T cells and RNA-seq analysis was performed. Specifically, RBPs were either depleted by lentiviral transduction of short-hairpin RNAs (shRNAs) (FIGS. 9A-9B), or ectopically expressed ORFs of those candidate RBPs which are not expressed in HEK293T cells or which do not have RBP-specific shRNAs (FIG. 9C). For each RBP, either two independent transductions of two different targeting shRNAs and two non-targeting shRNAs were performed, or two independent transfections with a plasmid directing expression of the RBP as a V5-tagged fusion were performed, with the FLAG construct as a control. PolyA$^+$ RNA was selected, sequencing libraries were prepared and sequenced to a depth of >32 (or >26 uniquely mapped)$\times 10^6$ reads.

Figure 3A:
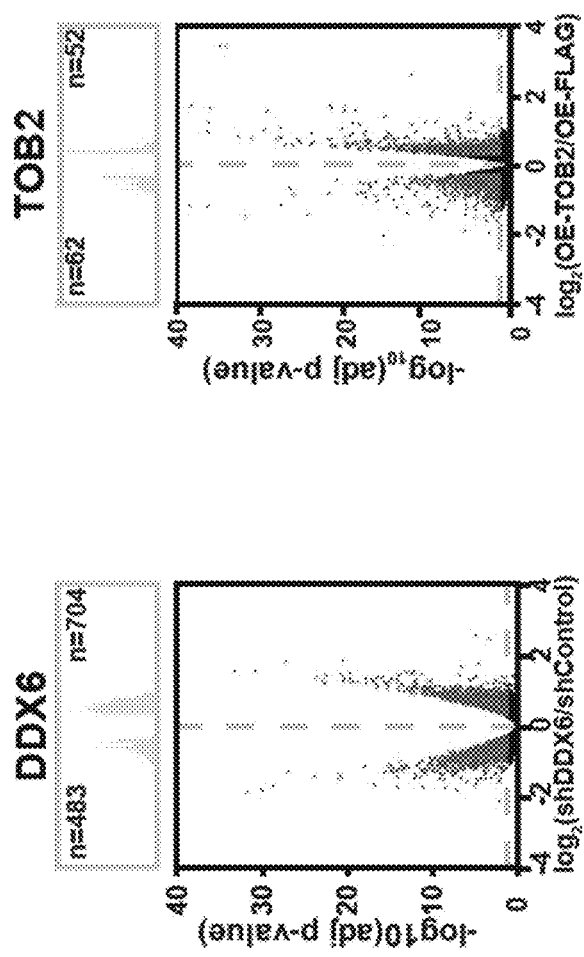
FIGS. 3A-3B show volcano plots showing the distribution of fold changes in transcript levels upon modulation of (FIG. 3A) destabilizers and (FIG. 3B) stabilizers, with distribution histograms shown at the top.
Figure 3B:
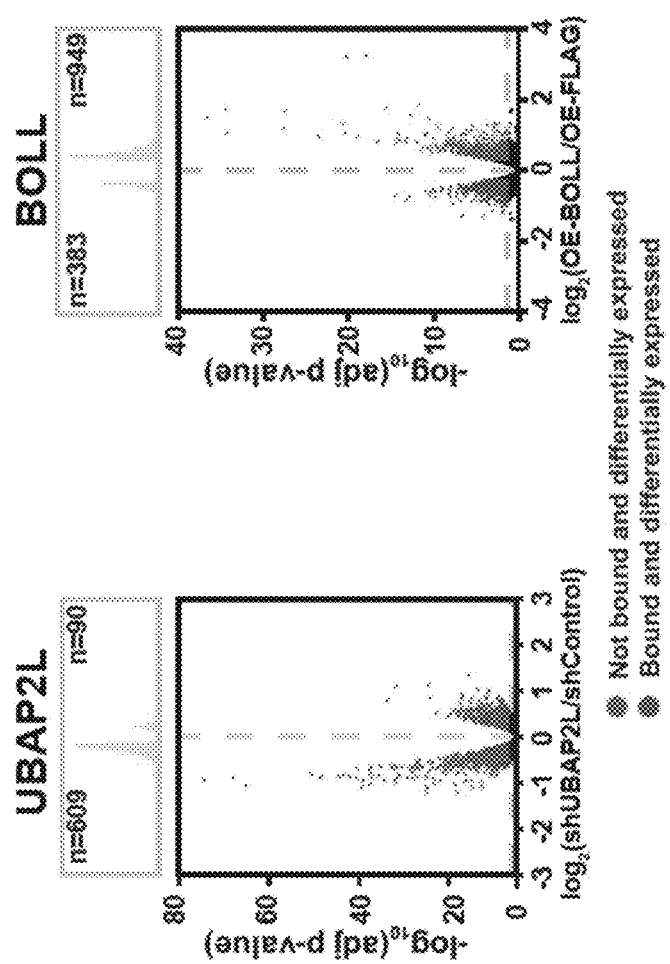
Figures 9H, 9I:
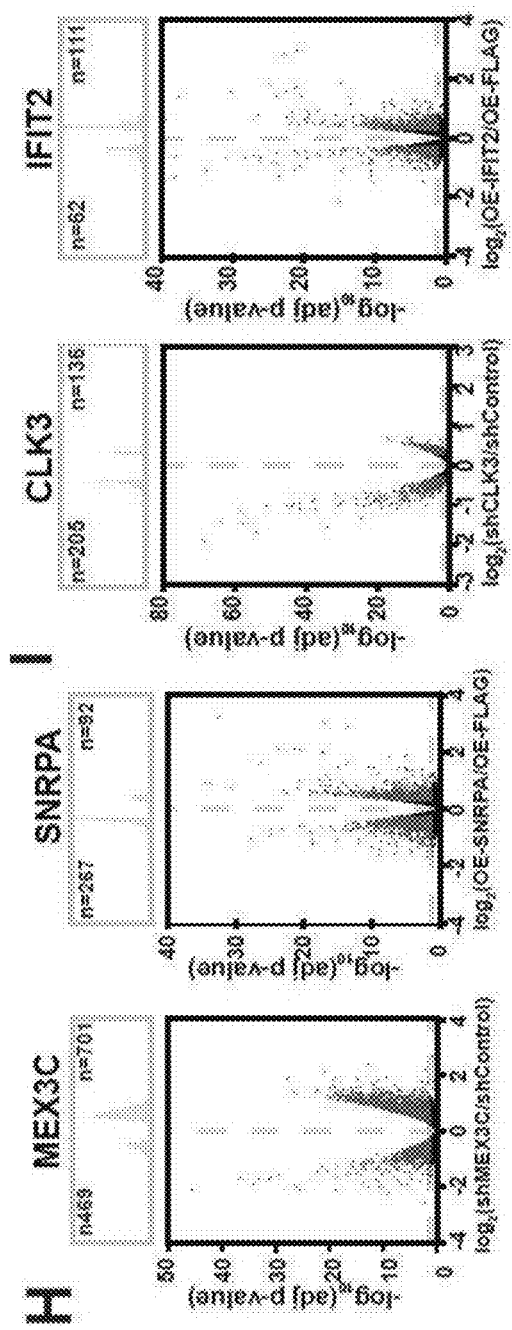
FIGS. 9H-9I show volcano plots showing the distribution of fold-changes in transcript levels, with distribution histograms at the top, upon (FIG. 9H) depletion of the destabilizer MEX3C (left), overexpression of the destabilizer SNRPA (right)

To assess the effect of a candidate RBP on transcript levels, the number of significantly up- or down-regulated genes were measured upon knockdown or overexpression (FIGS. 9D-9G). In general, the manipulations of RBP levels resulted in a largely unperturbed population of transcripts, typically 80% at threshold of statistical significance [$\geq 1.23$-fold, false discovery rate (FDR)-corrected p:0.05 versus non-targeting shRNA or FLAG control]. This indicates that the candidate RBPs affect specific sets of target transcripts, instead of having effects on global transcript stability. When only considering those transcripts that were bound by the respective RBP, as measured by eCLIP ($\geq 1$ significantly enriched cluster per transcript), higher numbers of targets were observed that change in the direction anticipated by the tethering assays, than in the opposite direction, for candidate destabilizers, MEX3C, DDX6, SNRPA, and TOB2 (FIG. 3A; FIG. 9H) and candidate stabilizers UBAP2L, CLK3, BOLL, and IFIT2 (FIG. 3B; FIG. 9I). In other words, knockdown of destabilizers led to more up-regulated genes, whereas overexpression of destabilizers led to more down-regulated genes. Expectedly, reciprocal effects are observed in the alterations of stabilizing RBPs.

Figure 3C:
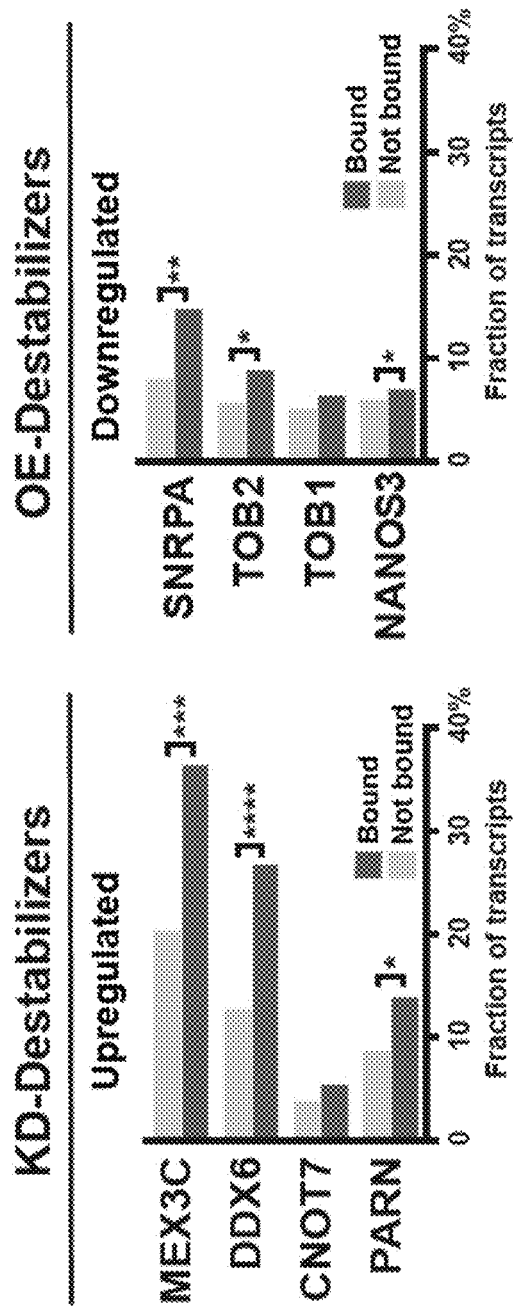
FIGS. 3C-3D show bar plots showing the percentage of overlap between genes significantly up- or downregulated [$\log_2$(fold change)≥1.23 and FDR-corrected p≤0.05] and significantly bound (≥4-fold-enriched and $p≤10^{-3}$ versus SMInput in eCLIP) upon knockdown (KD) or overexpression (OE) of candidate (FIG. 3C) destabilizers and (FIG. 3D) stabilizers.
Figure 3D:
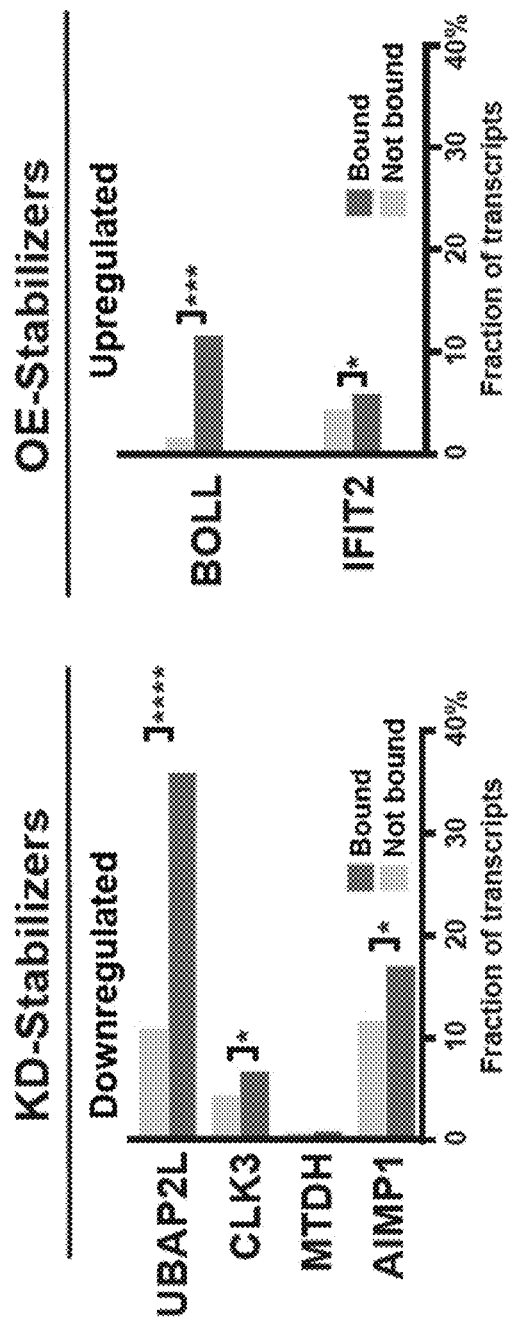
Figures 3E, 3F:
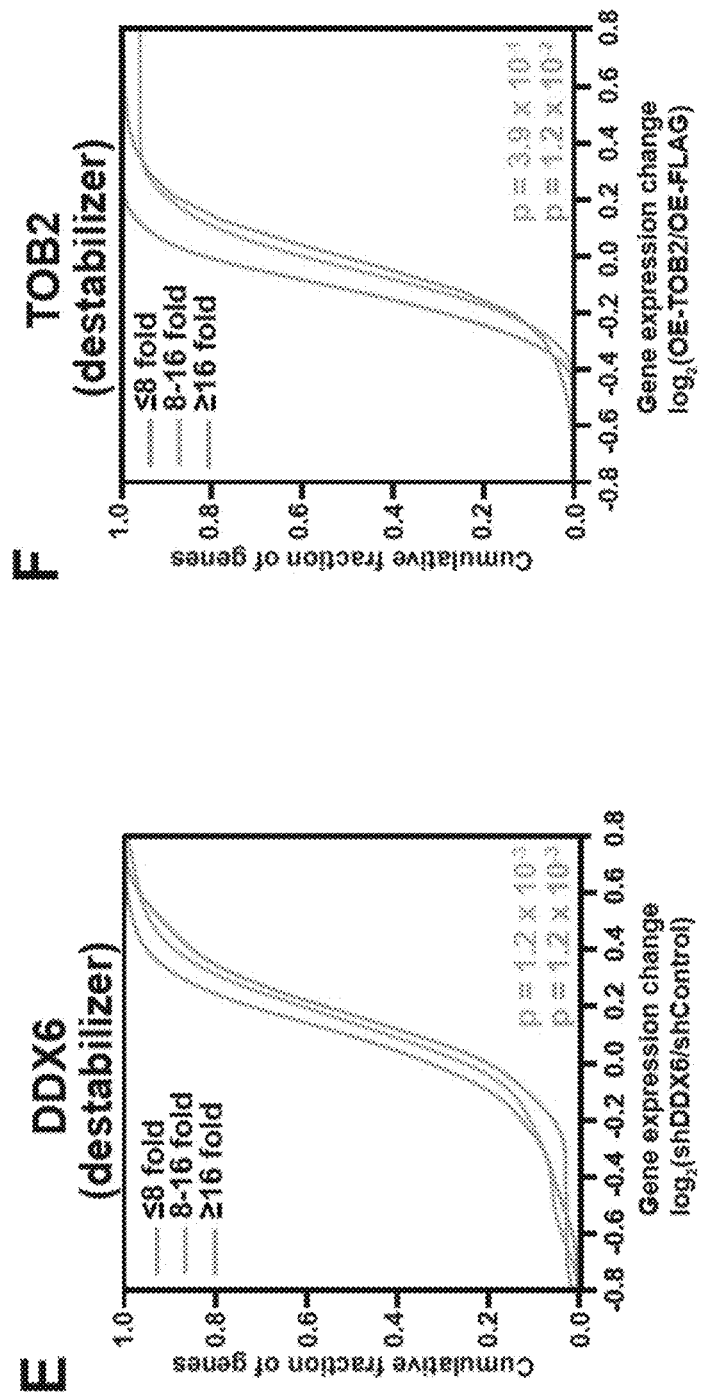
FIGS. 3E-3H show cumulative distribution plots of transcript log 2-transformed fold changes of overexpression versus vector control or shRNA-mediated knockdown vs non-targeting control, as indicated, for the destabilizers (FIG. 3E) DDX6 and (FIG. 3F) TOB2, and the stabilizers (FIG. 3G) UBAP2L and (FIG. 3H) BOLL. p-values were calculated using a two-tailed Mann-Whitney Utest.
Figure 3H:
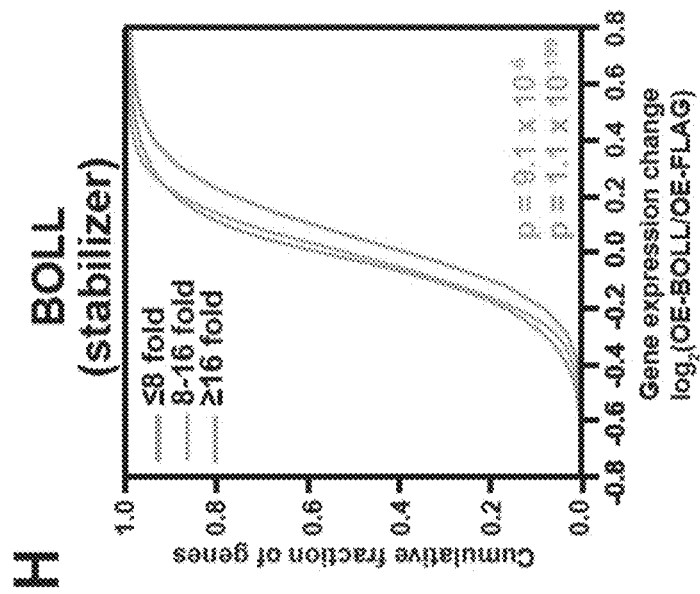
Figure 3G:
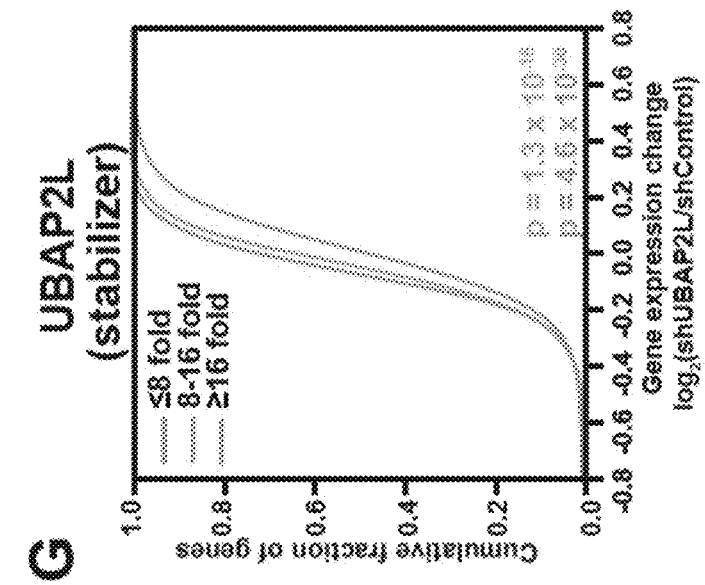
Figures 3I, 3J:
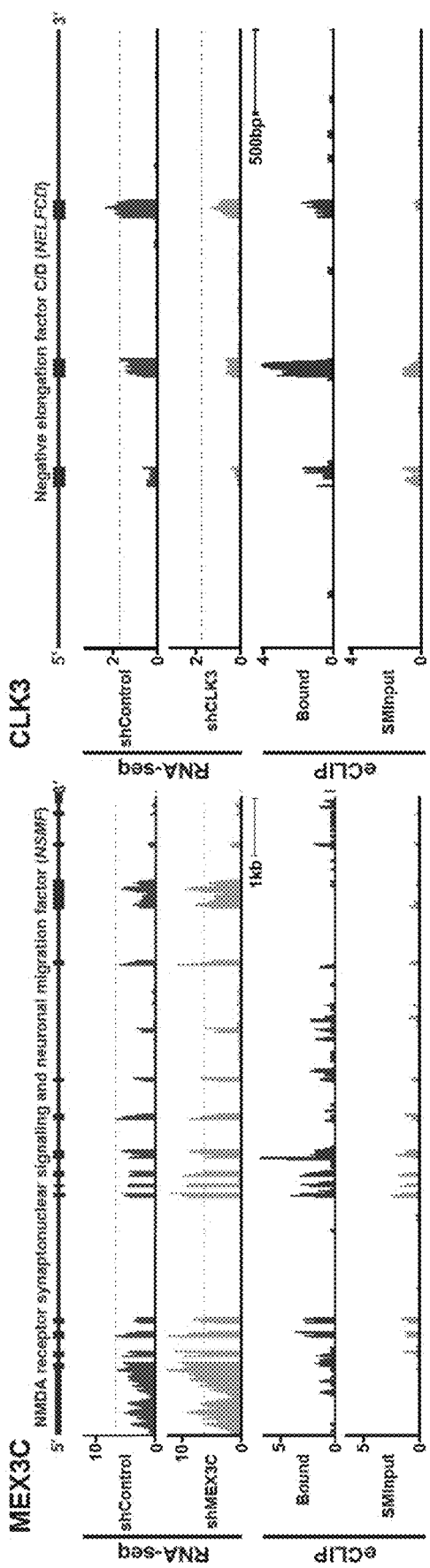
FIGS. 3I-3J show genome browser views from shRNA-mediated knockdowns showing RNA-seq reads and eCLIP reads for (FIG. 3I) MEX3C at the NSMF locus and (FIG. 3J) CLK3 at the NELFCD locus.
Figure 9J:
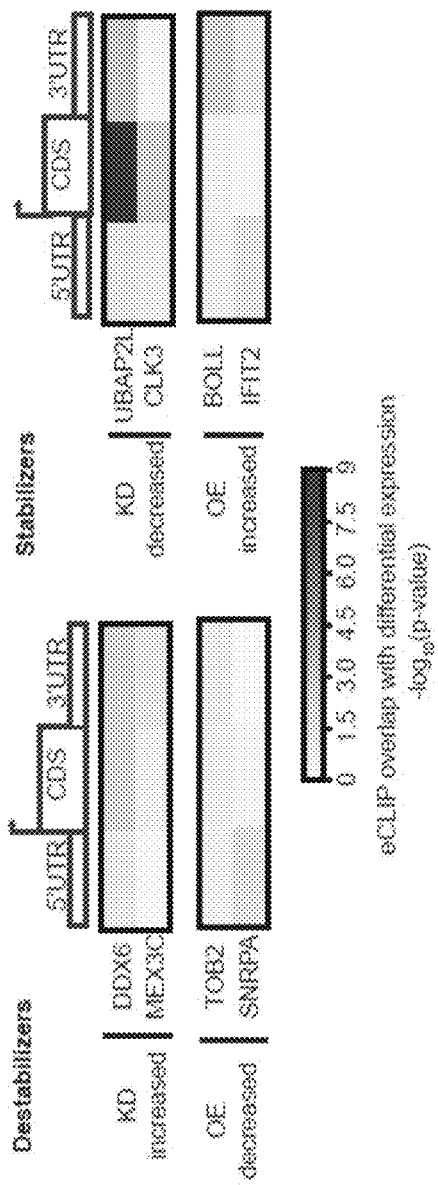
FIG. 9J shows a heatmap showing significance in differential expression of genes significantly differentially expressed and significantly bound vs all unbound genes, upon knockdown (KD) or overexpression (OE) of candidate RBPs in each region.

It was also confirmed that the fraction of bound targets in the genes changing in the anticipated direction was statistically significantly enriched relative to unbound targets (FIGS. 3C-3D). In fact, significant correlation was observed between different eCLIP cluster fold enrichments IP over SMInput and change in transcript levels, for both candidate destabilizers (e.g. DDX6 and TOB2; FIGS. 3E-3F) and candidate stabilizers (e.g. UBAP2L and BOLL; FIGS. 3G-3H). This indicates that the candidate RBPs directly engage hundreds of previously unknown target endogenous mRNAs to affect transcript levels in the predicted direction. For example, knockdown of the destabilizer MEX3C increased transcript levels of NSMF mRNA, a MEX3C-bound transcript (FIG. 3I). Conversely, depletion of the stabilizer CLK3 reduced the abundance of its target NELFCD mRNA (FIG. 3J). Interestingly, when it was further evaluated which genic regions bound by the RBP are most correlated with transcript levels, UBAP2L binding within CDS was the most enriched (FIG. 9J). In general, it was concluded that the majority of the candidate RBPs affect mRNA levels of their endogenous RNA targets, in agreement with the tethering results.

Example 5—UBAP2L Increases mRNA Polysome Association and Promotes Translation

Figures 4A, 4B:
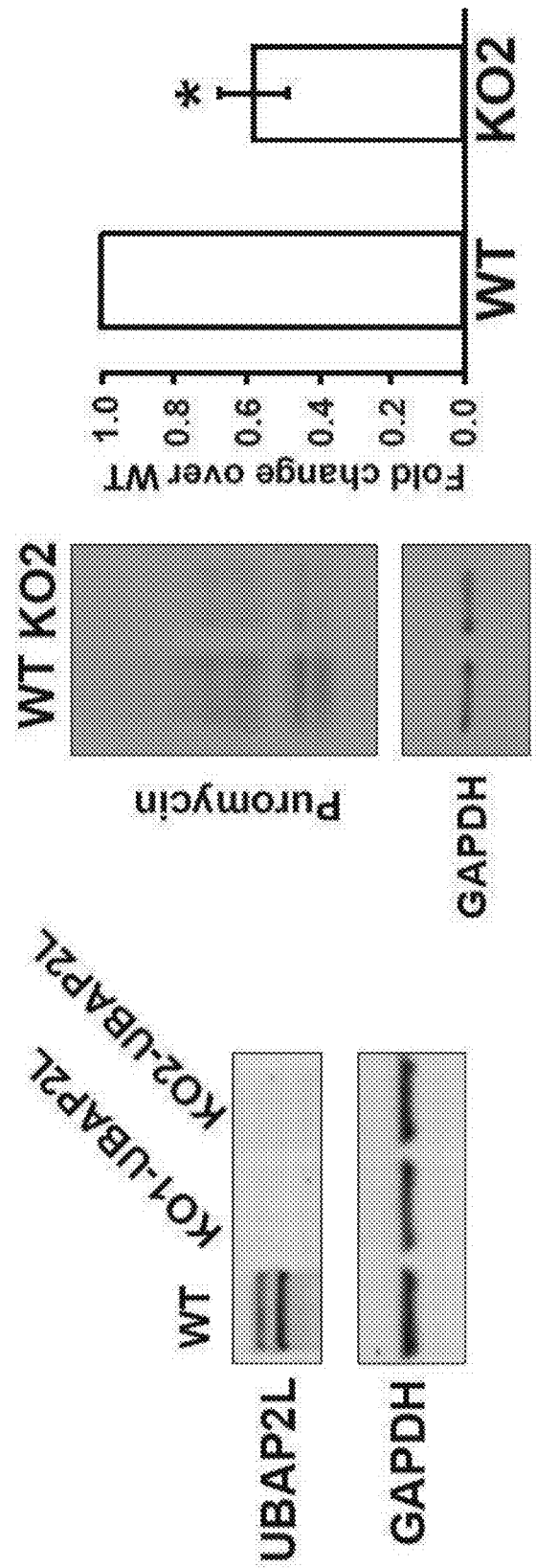
FIGS. 4A-4B show translation monitoring using puromycin incorporation.
Figures 4C, 4D:
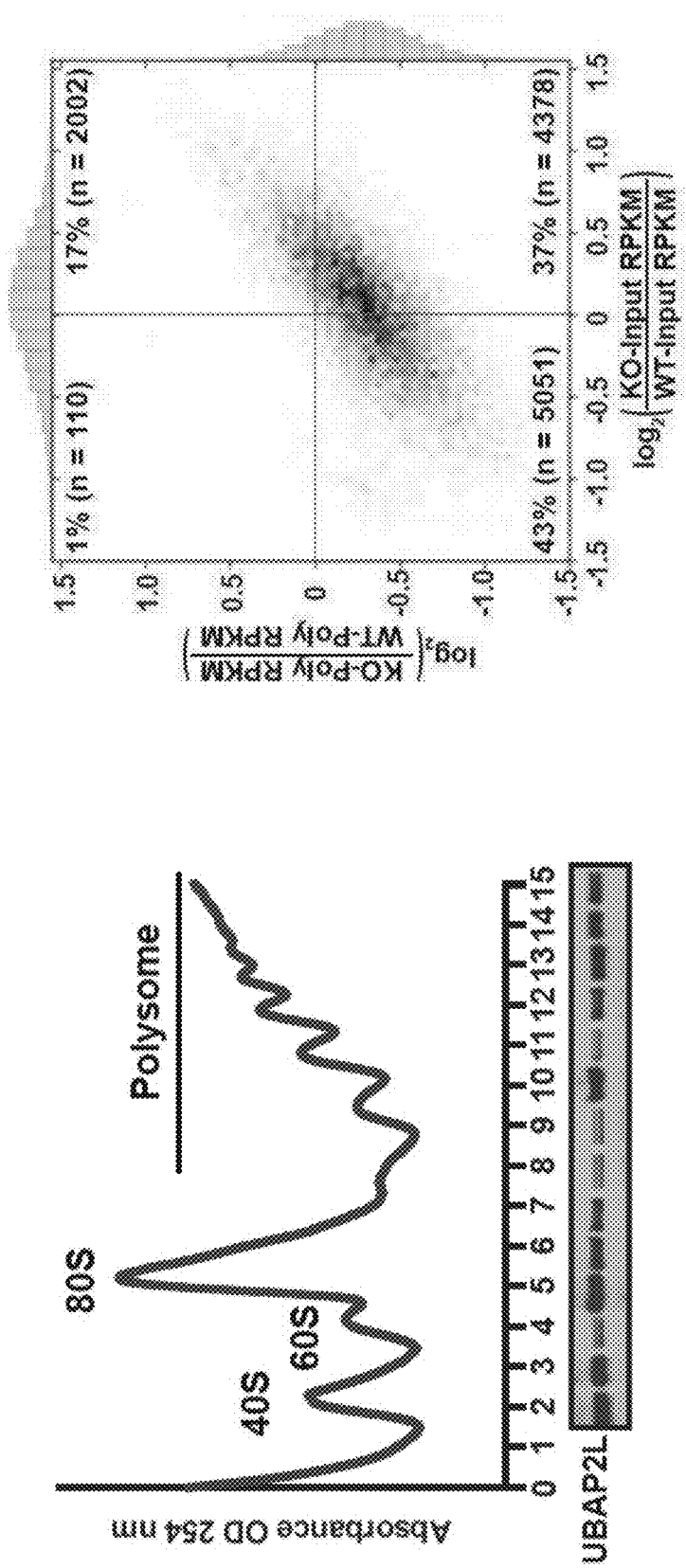
FIG. 4C shows a polysome profile of UBAP2L. (Top) Absorbance (at 260 nm) plot of a HEK293T cell lysate fractionated through a $10^{-50}$% a sucrose gradient. (Bottom) Western blots of UBAP2L from corresponding sucrose fractions.
FIGS. 4D-4E show global transcript association with polysomes in UBAP2L knockout cells.
Figures 10A, 10B, 10C, 10D:
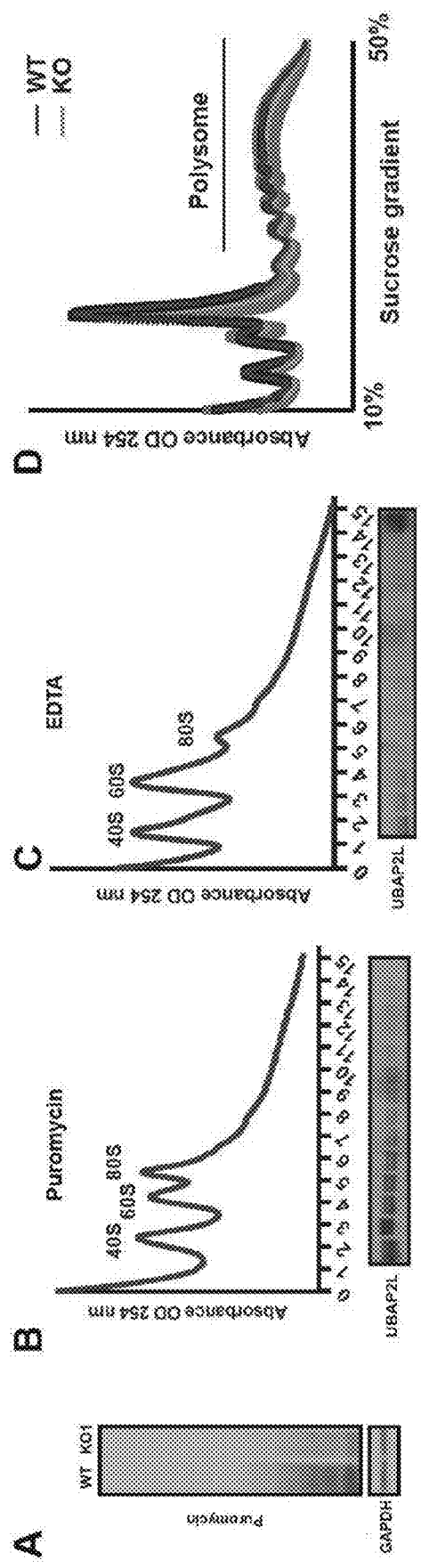
FIG. 10A shows translation monitoring using puromycin incorporation. Representative anti-puromycin western blot of extracts from puromycin-treated UBAP2L knockout (KO1) and parental (WT) HEK293T cell lines. GAPDH served as loading control.
FIGS. 10B-10C show polysome profile of UBAP2L after (FIG. 10B) treatment with 0.5 mM puromycin in vivo, and (FIG. 10C) 30 mM EDTA in vitro. (Top) Absorbance (at 260 nm) plot of a HEK293T cell lysate fractionated through a $10^{-50}$% a sucrose gradient. (Bottom) Western blots of UBAP2L from the corresponding fractions.
FIG. 10D shows polysome profiles of HEK293T cells (WT, n=2) and UBAP2L knockout HEK293T cells (KO, n=4) fractionated through $10^{-50}$% a sucrose gradients.

Among the 13 candidates that were analyzed, UBAP2L had the highest CDS read density enrichment (FIG. 2D and FIG. 9J), suggesting a direct role in translation. However, such a function for UBAP2L had not been described. Global protein synthesis rates were measured in cells lacking UBAP2L with the SUnSET assay, which uses incorporation of puromycin (a structural analog of aminoacyl-transfer RNA) to label newly synthesized proteins. HEK293T cells biallelically deleted for UBAP2L by CRISPR/Cas9-mediated genome editing showed a ~40% reduction in protein synthesis (FIGS. 4A-4B; FIG. 10A), indicating that UBAP2L promotes global translation. Next, sucrose gradient centrifugation of HEK293T lysates was performed to examine the association of UBAP2L with ribosomes. UBAP2L from HEK293T cell lysates co-fractionated with monosomes and polysomes on sucrose gradients, suggesting a role for UBAP2L in translation (FIG. 4C). In order to rule out the possibility that this observation is due to the presence of UBAP2L in non-ribosomal complexes of similar buoyant density, cells were treated with puromycin to release polysomes from transcripts. Puromycin treatment led to accumulation of 80S monosomes, as expected, and levels of UBAP2L in fractions corresponding to polysomes were strongly reduced (FIG. 10B). Cell lysates were also treated with EDTA to disassemble 80S monosomes into 40S and 60S ribosomal subunits and found that, similarly, UBAP2L was depleted from fractions corresponding to monosomes (FIG. 10C). These results strongly suggest that UBAP2L directly interacts with translating ribosomes.

Figure 4F:
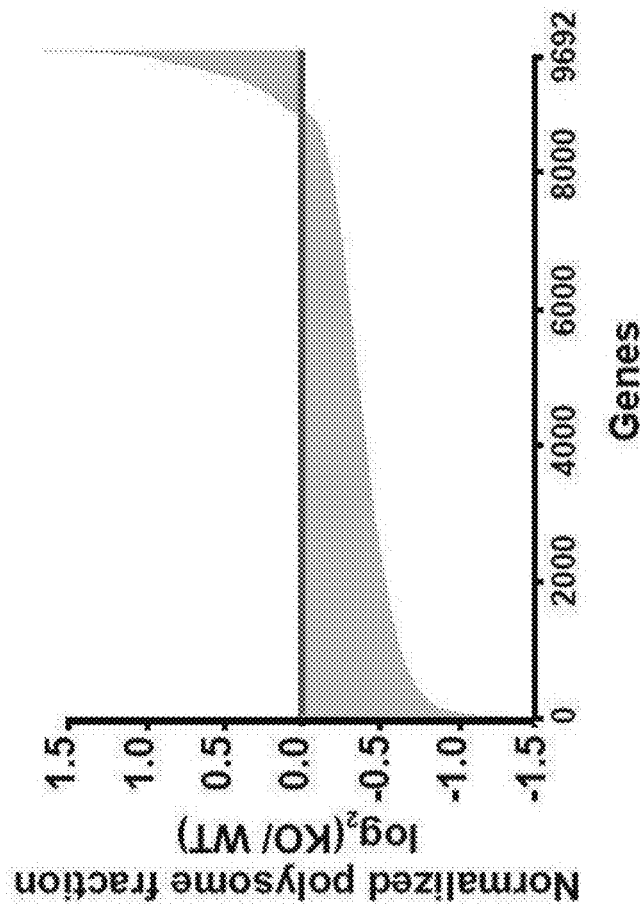
FIG. 4F shows a bar graph showing log 2-transformed ratios of input-normalized polysome transcript levels (RPKM) between the two UBAP2L knockout lines (KO) and control (WT). Only transcripts with RPKM≥1 in all three samples were considered (n=9,692). RPKM levels for the two KO lines were averaged.
Figure 4E:
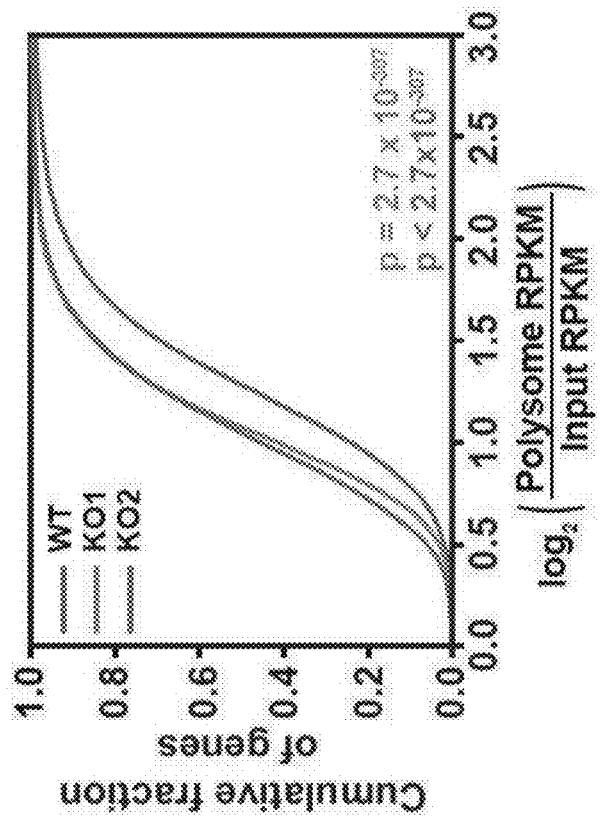
Figures 10E, 10F, 10G, 10H:
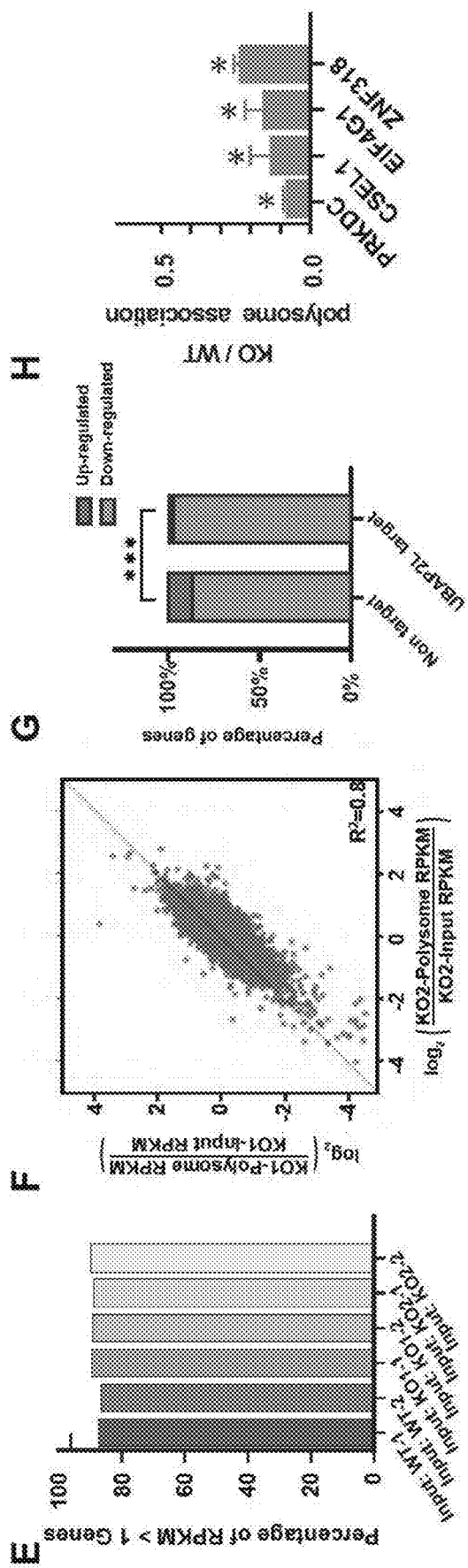
FIG. 10E shows bar graphs showing percentages of transcripts with RPKM$\geq$1 of all transcripts with $\geq$10 reads per transcript, for two UBAP2L knockout lines and control samples (WT).
FIG. 10F shows scatter plots showing correlation of log 2-transformed ratios of input-normalized polysome transcript levels (RPKM) between the two UBAP2L knockout HEK293T lines.
FIG. 10G shows a bar graph showing the percentage of regulated transcripts in UBAP2L targets, and nontargets.
FIG. 10H shows quantitative qRT-PCR validation of reduced polysome association for the indicated transcripts. Transcript levels in inputs and polysome fractions were measured for KO and WT samples.

To identify specific transcripts subject to UBAP2L-mediated translational regulation, polysome profiling was performed in cell lysates from two independent UBAP2L knockout clonal isolates and from two control samples (FIG. 10D). From two independent fractionations per line, polyA+ mRNA was isolated from a portion of the input lysates and from pooled polysome fractions, and RNA-seq libraries were prepared and sequenced. All transcripts with RPKM≥1 in inputs were considered (FIG. 10E). It was found that UBAP2L knockout resulted in a larger number of transcripts with changes in pooled polysome fractions compared to changes in input RNA abundance (FIG. 4D), suggesting that UBAP2L predominantly acts at the translational level. As a measure of ribosome association, the ratio of transcript RPKMs in polysome pools over input for all transcripts was computed. A significant decrease was found ($p<10^{-307}$; Mann-Whitney U test, two-tailed) in mean transcript polysome-enrichment in both UBAP2L knockout lines compared to the controls (FIG. 4E). Replicate analyses showed excellent correlation between the cell lines (FIG. 10F). When isolated those genes that changed in the same direction in both knockout lines were isolated, it was found that overall nearly 10-fold more transcripts were reduced in translation (90.6%; n=8,784) than enhanced (9.4%; n=908) (FIG. 4F). Even more strikingly, 99% of the 1,425 UBAP2L target transcripts, identified by eCLIP, showed significant down-regulation in polysome association upon UBAP2L knockout (FIG. 10G). A subset of target transcripts were also measured by quantitative RT-PCR, which confirmed the magnitude of translational downregulation (FIG. 10H).

Figures 10I, 10J, 10K:
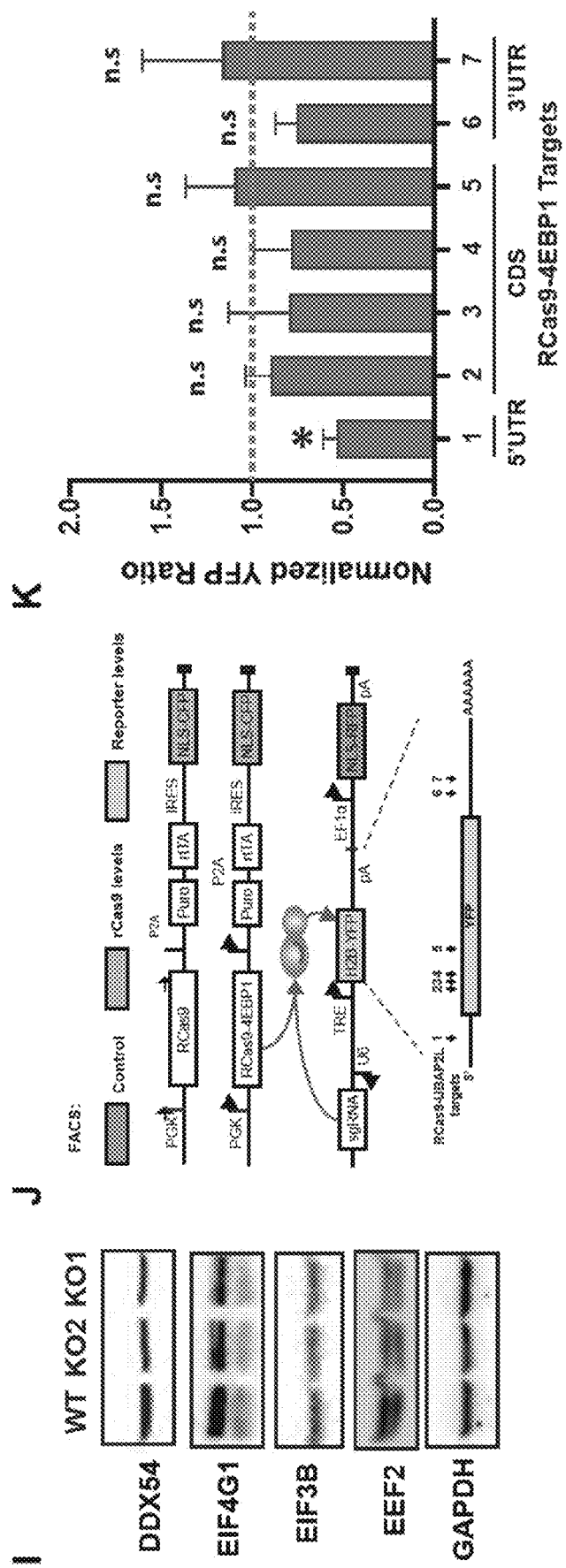
FIG. 10I shows Western blots of EIF4G1, EIF3B, DDX54, and EEF2 in UBAP2L knockout cells (KO1, K02). GAPDH served as a loading control.
FIGS. 10J-10K show quantitative fluorescence-activated cell sorting (FACS)-based reporter assay for mRNA translation using RCas9-fused 4EBP1.

To investigate how depletion of UBAP2L affected global translation, the gene function attributes of UBAP2L direct targets were evaluated where a significant enrichment (FDR <0.05) was observe in protein translation and ribosome biogenesis terms by Gene ontology (GO) analysis (FIG. 4G). It was also revealed that UBAP2L depletion decreased polysome association on mRNAs encoding translation initiation factors, elongation factors, tRNA synthesis proteins, and poly(A) binding proteins (FIG. 4H). In fact, western blot analysis of these UBAP2L targets confirmed decreased protein levels of translation and elongation factors, such as Eukaryotic Translation Initiation Factor 4 Gamma 1 (EIF4G1), DEAD-Box Helicase 54 (DDX54), and Eukaryotic Translation Elongation Factor 2 (EEF2) in cells lacking UBAP2L (FIG. 4I and FIG. 10I). Taken together, these results suggest that UBAP2L enhances translation by directly binding mRNA substrates and also increasing translation of genes involved in global protein synthesis.

Figures 4J, 4K, 4L:
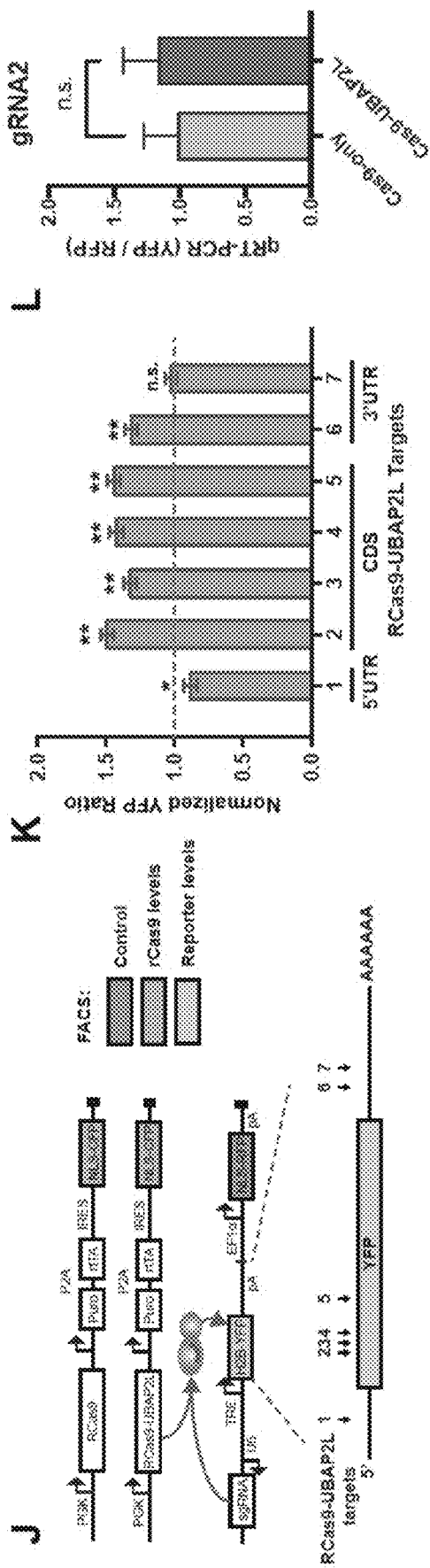
FIGS. 4J-4K show quantitative fluorescence-activated cell sorting (FACS)-based reporter assay for mRNA translation using RCas9-fused UBAP2L.
FIG. 4L shows a bar graph showing ratios of YFP/RFP mRNA levels in rCas9-UBAP2L expressing cells, normalized to rCas9 expressing cells, in the presence of the gRNA targeting site 2. Transcript levels were measured by qRT-PCR and calculated with the AACT method.

Example 6—Programmable RNA-Targeting CRISPR-Mediated Recruitment of UBAP2L Promotes Translation In order to assess the dependence of UBAP2L-mediated translational regulation on direct binding to its target mRNA, a FACS-based reporter assay was employed using UBAP2L fused to RNA-targeting RCas9 (RCas9) (FIG. 4J). As a control, the assay was performed with RCas9-fused 4EBP1, an inhibitor of translational initiation (FIG. 10J). HEK293T cell lines expressing a RCas9-UBAP2L fusion, RCas9-4EBP1 fusion, or Cas9 only were derived via transposase-mediated piggyBAC genomic integration of plasmid constructs. A second construct harboring a reporter that stably expresses RFP transcripts not regulated by RCas9, a guide RNA, and tetracycline-inducible YFP transcripts was then transfected with the guide RNA target sequences. 7 different guide RNAs were designed, targeting locations across the YFP transcript (5' UTR, CDS, and 3'UTR), and a non-targeting guide RNA. Post transcriptional regulation was then measured as changes in the normalized YFP/RFP fluorescence ratio between Cas9-fusion and Cas9 only cells by using analytical flow cytometry. Due to the random nature of piggyBAC-mediated integration in terms of construct integration sites and numbers, regulation for various rCas9 construct levels (CFP) and reporter construct levels (RFP) can be quantified across thousands of data points (cells). With this highly sensitive and quantitative assay, it was observed that the extent of the most strongly enhanced effect of UBAP2L on YFP reporter expression was dependent on UBAP2L directed to targeting sites within the 3'UTR and coding regions (FIG. 4K). In contrast, significant 4EBP1-mediated reporter repression was only observed when 4EBP1 was targeted to the 5' UTR, as expected (FIG. 10K). Normalized YFP mRNA levels were not significantly different between RCas9-UBAP2L and RCas9 expressing cells transfected with gRNA 2 (which elicited the strongest increase) (FIG. 4L). These results indicate 305 that UBAP2L's positive effect on reporter expression was not due to upregulation of reporter mRNA. The UBAP2L-RCas9 results indicate a programmable means to enhance translation and further corroborate the observations from eCLIP and tethering in another orthogonal manner.

Figure 5A:
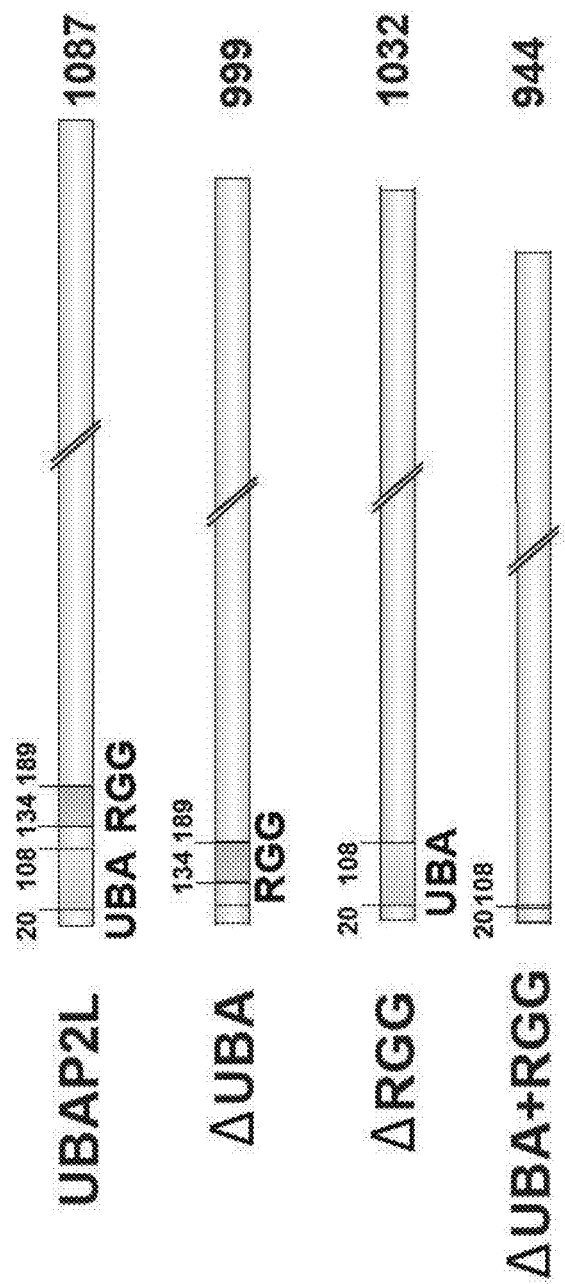
FIG. 5A shows domain structures of UBAP2L constructs inducibly expressed in UBAP2L knockout HEK293T cells. The ubiquitin-associated domain (UBA) and arginine-glycine-rich region (RGG) are indicated.
Figures 5B, 5C:
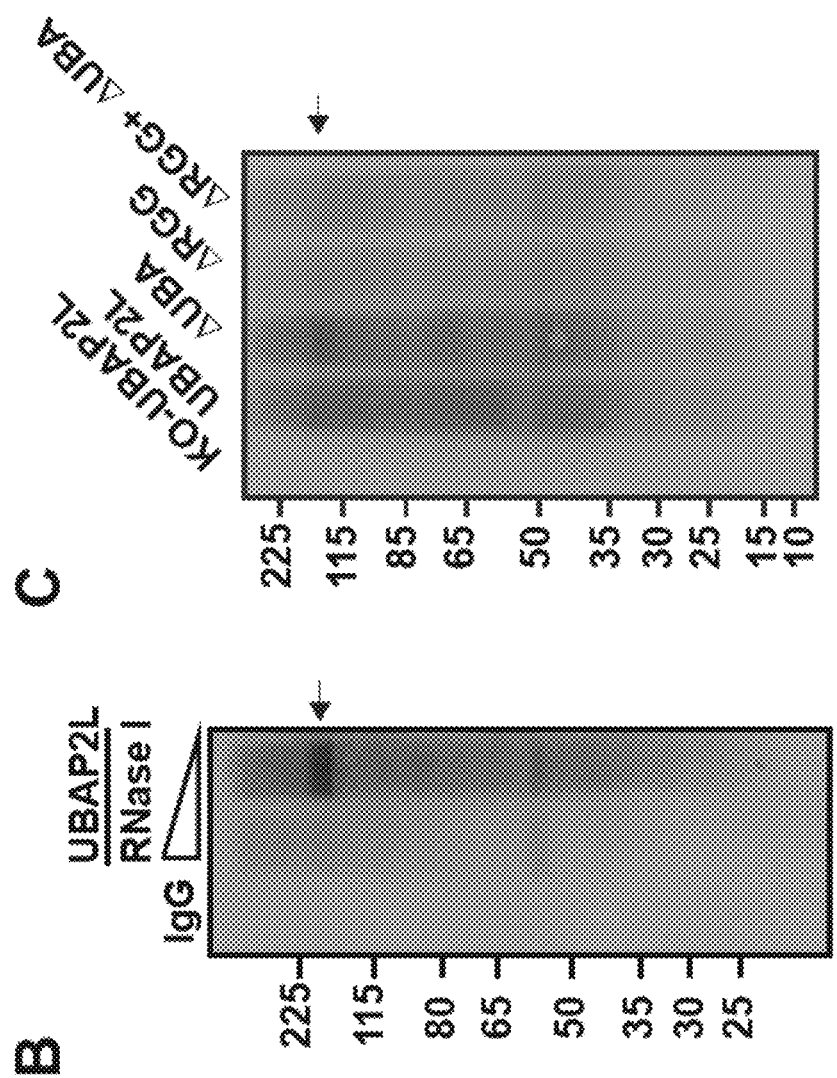
FIG. 5B shows autoradiograph of UBAP2L-RNA complexes immunoprecipitated from UV cross-linked HEK293T cells treated with increasing concentrations of RNase I, radiolabeled and separated on SDS polyacrylamide gel. Arrow indicates the expected molecular weight of UBAP2L.
FIG. 5C shows autoradiograph of UBAP2L-RNA complexes immunoprecipitated from lysates of UV-crosslinked UBAP2L knockout cells (KO-UBAP2L) expressing the indicated constructs, treated with RNase I, radiolabeled and separated on SDS polyacrylamide gel. Arrow indicates the expected molecular weight of UBAP2L.

Example 7—UBAP2L Binds to RNA Via the RGG Domain and Crosslinks to the Expansion Segments of the Ribosome To gain molecular insight into the mechanisms by which UBAP2L enhances mRNA translation, it was determined which protein domains mediate UBAP2L's interaction with RNA. UBAP2L is predicted to contain only two structured domains: a ubiquitin-associated (UBA) domain and an Arg-Gly-Gly repeat (RGG) domain, a common RNA and protein binding domain. Using inducible lentiviral vectors, UBAP2L was expressed, or truncated versions lacking the UBA domain (DUBA), the RGG domain (DRGG), or both (FIG. 5A), in UBAP2L knockout HEK293T cells. Then, UV-crosslinking, immunoprecipitation, RNA fragmentation and radiolabeling was performed to visualize RNA bound to UBAP2L (FIG. 5B). Deletion of the RGG domain resulted in dramatically reduced recovery of RNA, indicating that the interaction between UBAP2L and RNA is mainly mediated by the RGG domain (FIG. 5C).

Figure 5E:
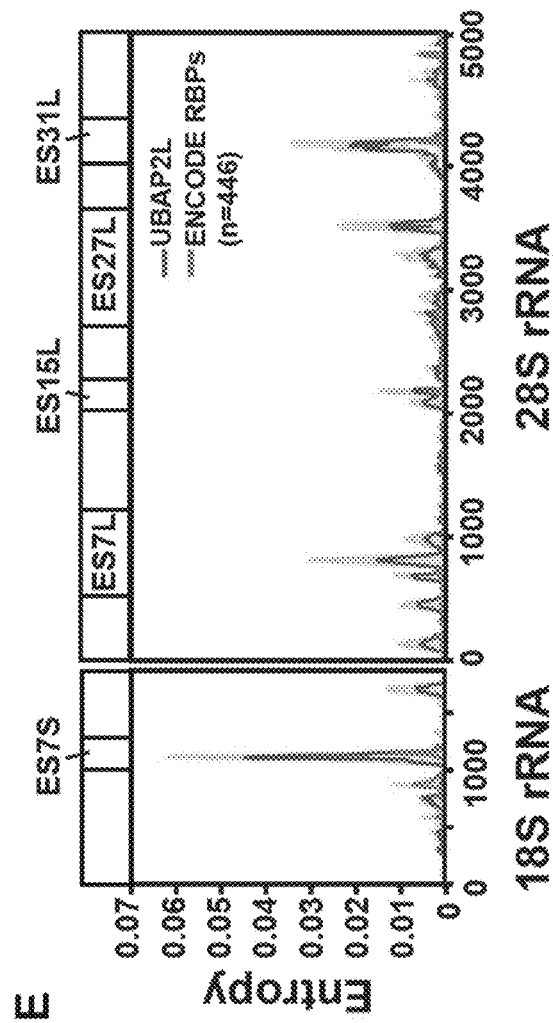
FIG. 5E shows locations of UBAP2L binding sites on rRNAs. Line plots showing the Kullback-Leibler divergence (relative entropy) for UBAP2L in HEK293T cells and the mean of 446 other RBPs from the ENCODE consortium on 18S and 28S rRNA. Lines show the mean of relative entropy, with light areas indicating 10%-90% confidence intervals.
Figure 5D:
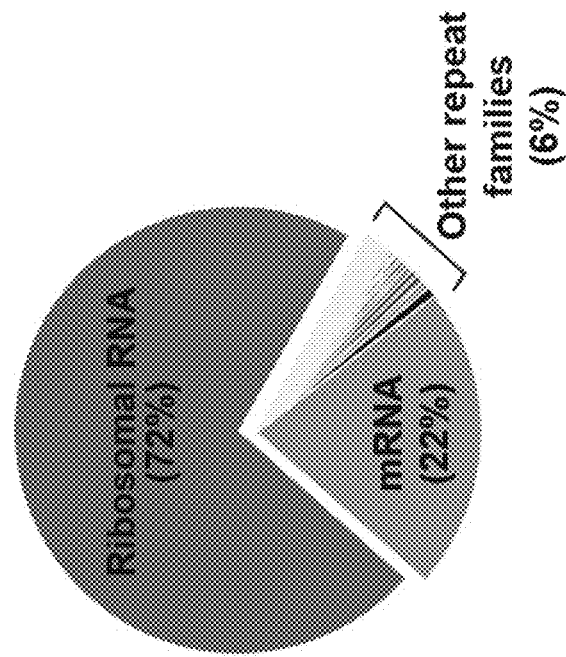
FIG. 5D shows a pie chart showing fractions of UBAP2L eCLIP reads from HEK293T cells unambiguously mapping to mRNAs, ribosomal RNAs, and other repeat families.
Figure 11A:
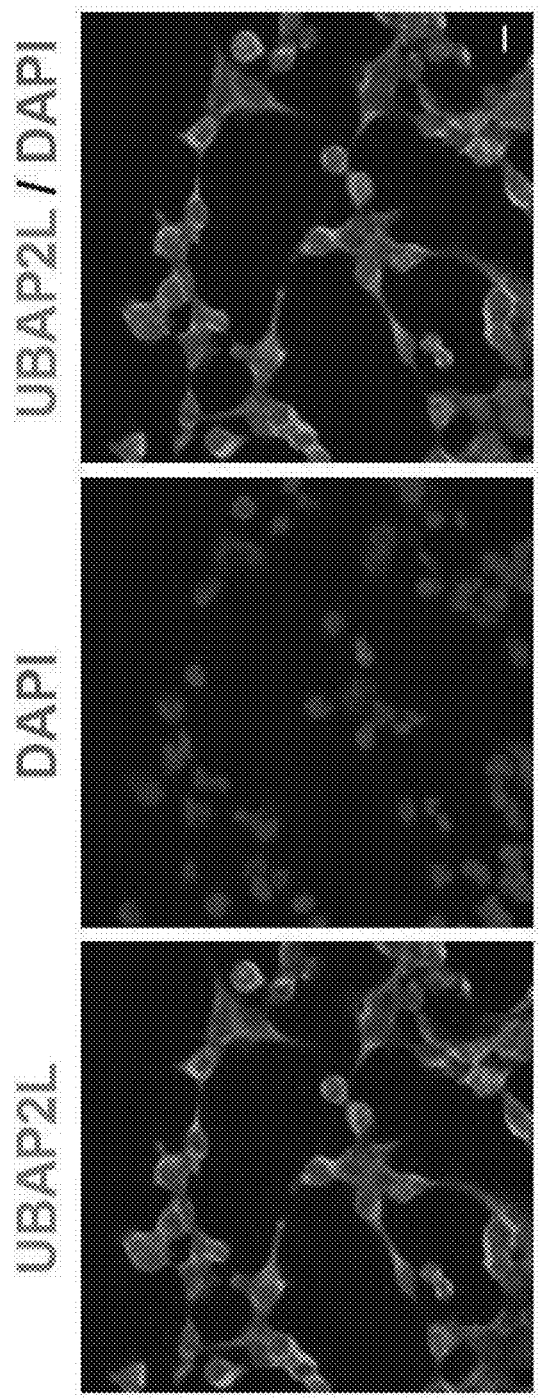
FIG. 11A shows immunofluorescence images showing UBAP2L in HEK293T cells. DAPI is a nuclei marker.
Figure 11C:
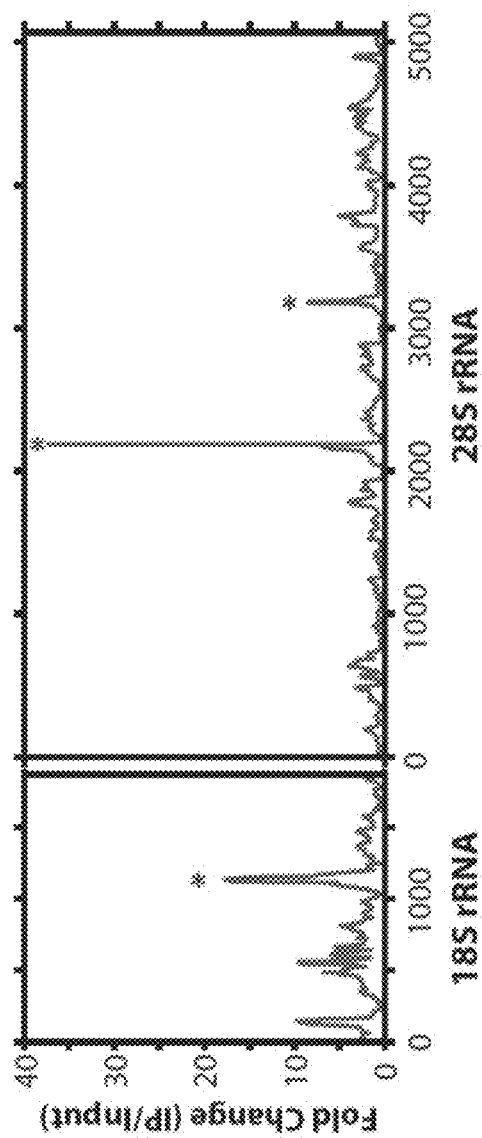
FIG. 11C shows locations of UBAP2L binding sites on rRNAs. The line plot shows the fold enrichment of reads for IP over SMInput. Diagram for the expansion segment ES15L shows the nucleotide corresponding to the highest peak in 28S rRNA region.
Figure 11B:
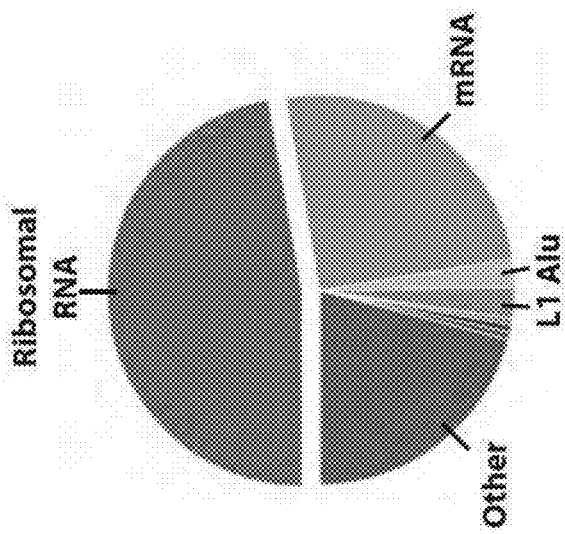
FIG. 11B shows a pie chart showing fractions of UBAP2L replicate 1 eCLIP reads unambiguously mapping to repeat families in HEK293T cells.
Figure 11D:
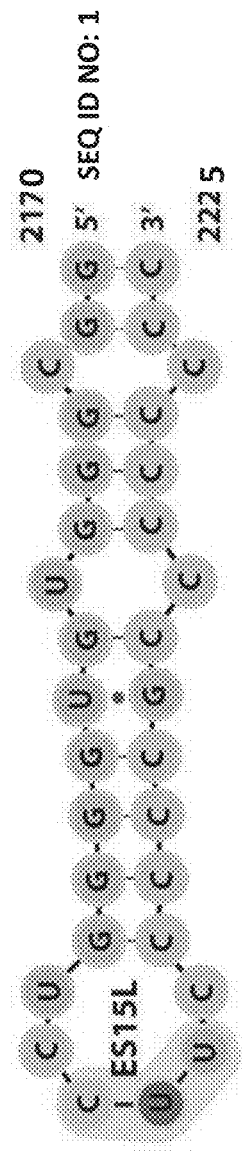
FIGS. 11D-11G show location of UBAP2L binding sites on rRNA.
Figure 11E:
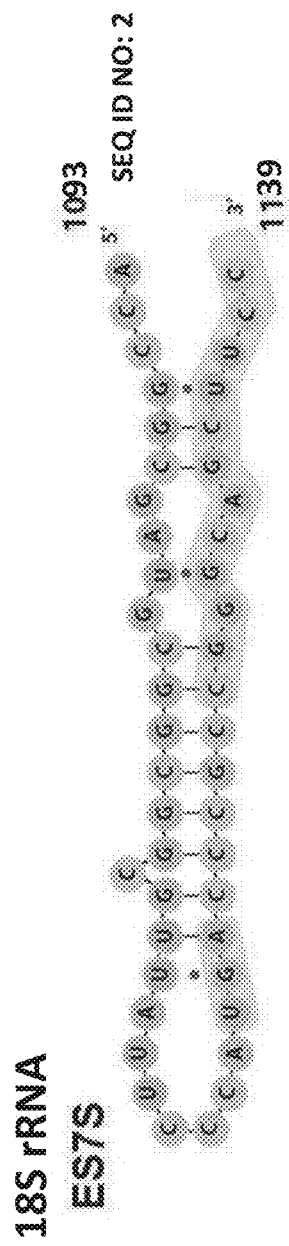
Figure 11F:
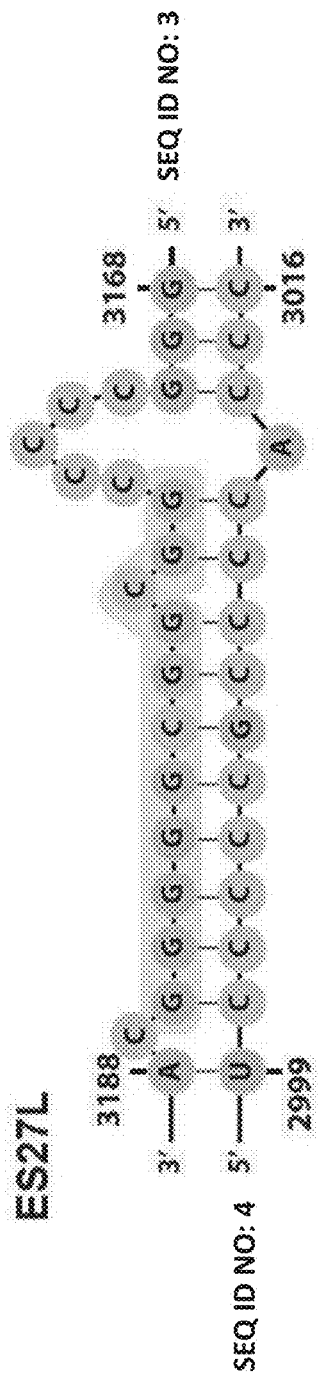
Figure 11G:
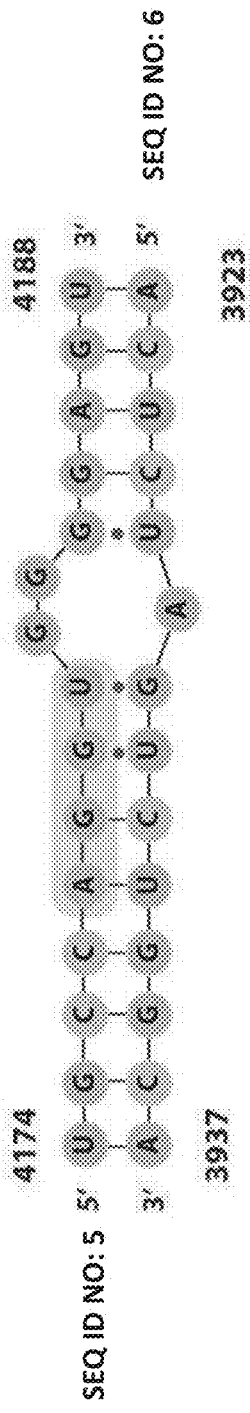

Given that UBAP2L cofractionated with monosomes and polysomes in sucrose gradients, it was reasoned that UBAP2L may interact directly with functional ribosomes. It was confirmed that UBAP2L is localized to the cytoplasm (FIG. 11A). Two UBAP2L eCLIP datasets were next examined using a repeat-family centric mapping strategy, which maps reads to consensus transcripts from repetitive and recurrent genomic loci, including ribosomal RNA (rRNA) genes. Remarkably, reads from rRNAs constituted the largest fraction (47%-72%) in both replicates, while mRNA reads totaled 22-25% (FIG. 5D; FIG. 11B). Closer inspection showed that reads were most highly enriched over SMInput at the expansion segments (ES) 15L, 27L of 28S rRNA, and ES7S of 18S rRNA (FIGS. 11C-11F), which are located at the solvent-exposed surface of ribosomes and are thought to engage with RBPs and mRNAs to modulate translation. As a further measure of the confidence of fold-enrichment, an information theoretic metric was utilized, relative entropy, which scales each enrichment with the strength of evidence (i.e. read depth) at each peak. It was confirmed that the peaks at ES15L, ES27L and ES7S (and an additional peak at ES31L) contained high information content (FIG. 5E; FIG. 11G). In contrast, the mean of 446 other RBPs shows very limited information content as a reflection of their specificity for binding the rRNAs. These cross-linking results indicate that UBAP2L directly interacts with ribosomes. This is consistent with a previous UBAP2L IP-mass spectrometry study that recovered peptides from 15 ribosomal proteins, further supporting a UBAP2L-ribosome interaction.

Figures 5F, 5G, 5H:
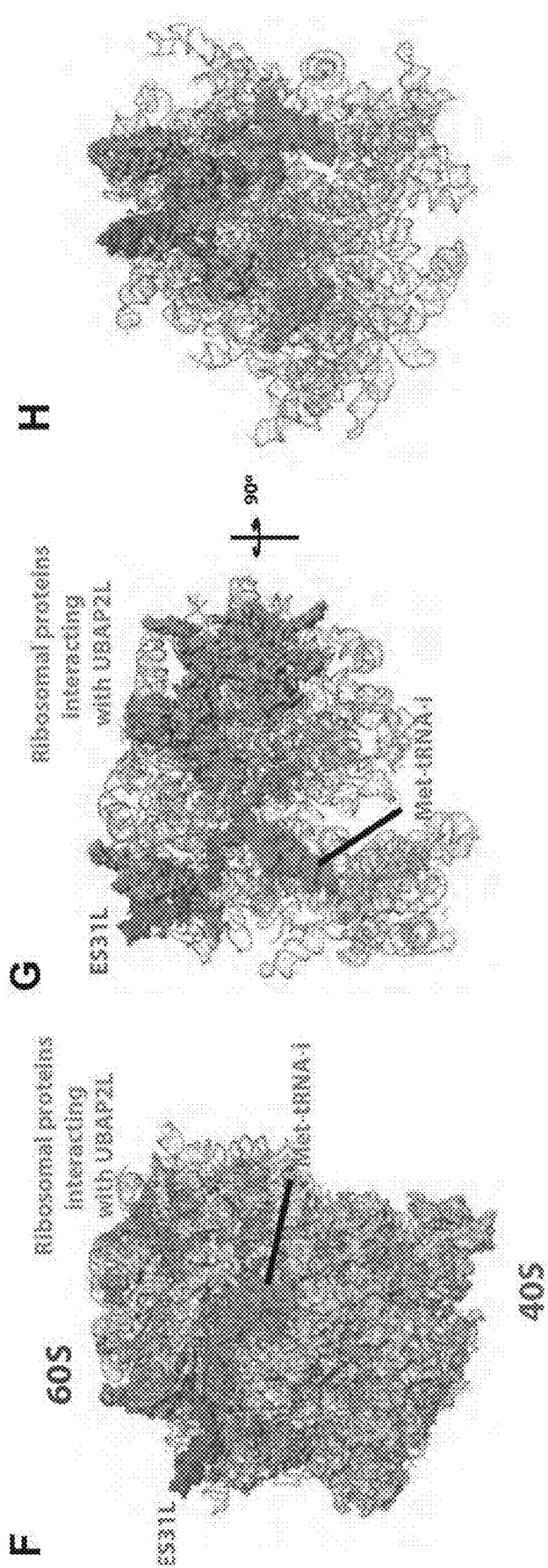
FIGS. 5F-5H show models of the interactions of UBAP2L on the human ribosome structure.

To assess the spatial arrangement of UBAP2L and the ribosome, these interactions were mapped onto the cryo-electron microscopy structure of the mammalian ribosome. The top ribosomal proteins that co-immunoprecipitate with UBAP2L cluster in the 60S subunit (FIG. 5F). In addition, ES31L, which is highly enriched for UBAP2L binding, lies close to the region of the 60S subunit, which is normally occupied by tRNA in the peptidyl site (P site) during protein synthesis (FIGS. 5G-5H). Collectively, these data support a model in which UBAP2L's function is associated with interactions with the ribosome.

Figure 6A:
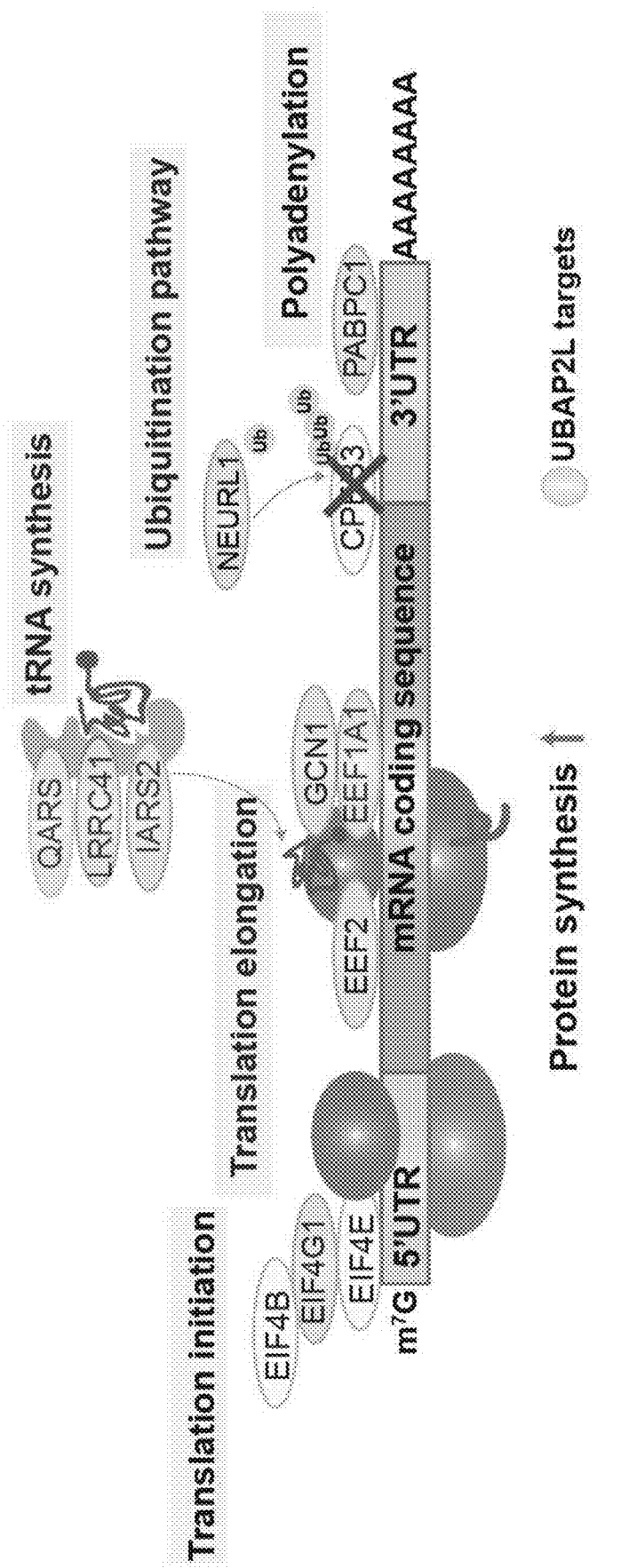
FIG. 6A shows an exemplary schematic of the role of UBAP2L in regulation of global protein synthesis. UBAP2L regulates translation of key genes involved in control of protein synthesis and degradation, including the indicated components the polyadenylation machinery, translation initiation and elongation factors, tRNA synthesis enzymes and members of the ubiquitin pathway.
Figure 6B:
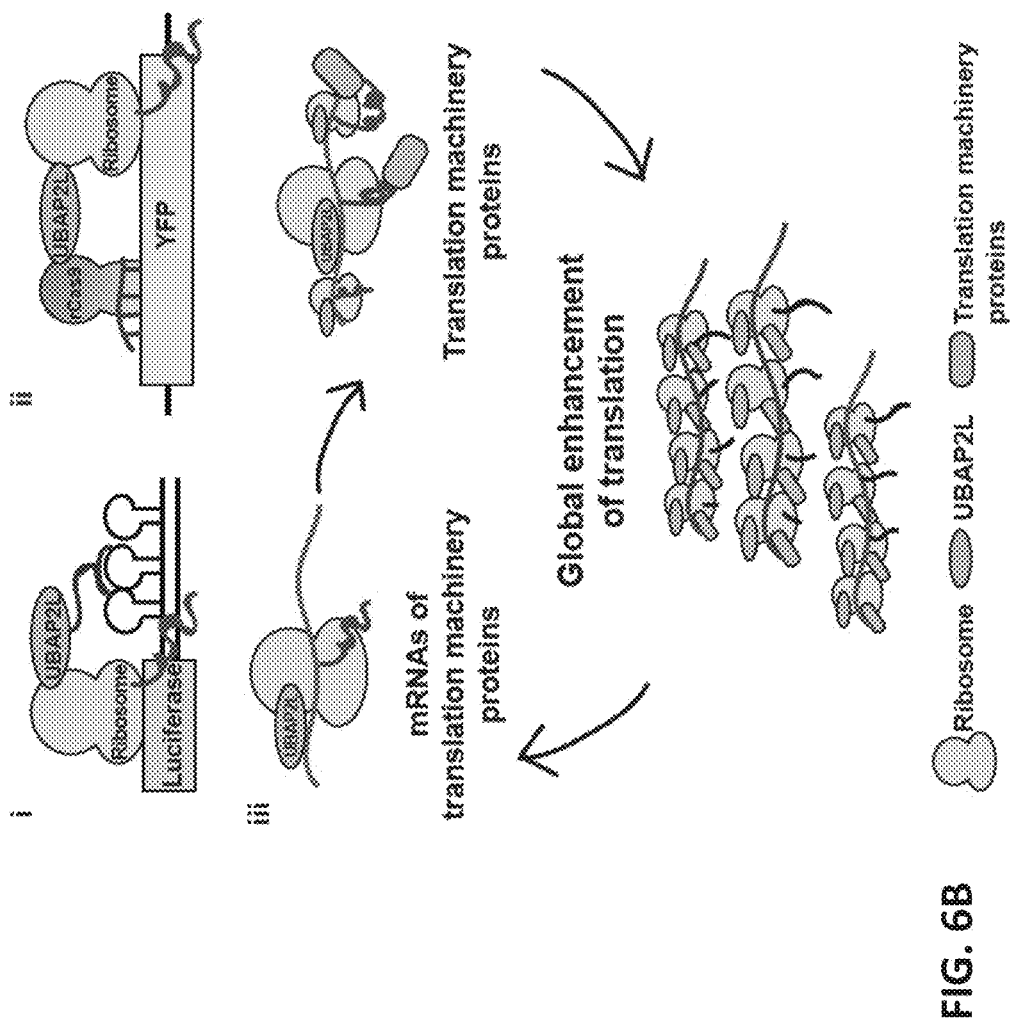
FIG. 6B shows an exemplary schematic where UBAP2L enhances global protein synthesis by increasing translation efficiency of its target transcripts, as demonstrated (i) by tethered function reporter assay, (ii) by rCas9-fused UBAP2L reporter assay, and (iii) endogenously in cells.

Furthermore, the transcriptome-wide analyses reveal that UBAP2L affects a significant number of mRNA targets, wherein mRNAs targeted by UBAP2L are themselves enriched for central regulators of translation, and protein synthesis (FIG. 6A), revealing a role for UBAP2L in modulating protein homeostasis in a global manner. The current working model proposes that UBAP2L is dynamically recruited to translating ribosome-mRNP complexes to enhance translation on many targets, including translational regulators to affect global protein synthesis (FIG. 6B).

Other Embodiments

It is to be understood that while the invention has been described in conjunction with the detailed. description thereof, the foregoing description is intended to illustrate and not limit the scope of the invention, which is defined by the scope of the appended claims. Other aspects, advantages, and modifications are within the scope of the following claims.

What is claimed is:

1. A method of modulating translation of a target RNA in a cell comprising:
   (a) assembling a modulation unit, wherein the modulation unit comprises:
      (i) an RNA binding protein (RBP) comprising BTG1, CNOT2, CNOT4, CNOT7, CPSF5, DDX6, EWSR1, FUBP1, hnRNPA0, hnRNPC1/2, MEX3C, NANOS1, NANOS2, NOP56, PARN, PRR3, RBM14, RBM7, RPS6, SAMD4A, SNRPA, SRSF11, TOB1, TOB2, UTP11L, YTHDF2, ZC3H18, ZCCHC11, ZFP36, ZFP36L1, ZFP36L2, ABT1, AC004381.6, AIMP1, ALDH18A1, ANXA2, APOBEC3F, ASCC1, ATP5C1, BCCIP, BOLL, BYSL, BZW1, CELF5, CLK1, CLK2, CPSF1, DAZ2, DAZ3, DAZ4, DCN, DDX1, DDX19B, DDX20, DDX39A, DMPK, EEF1A1, EIF3G, ERAL1, XOSC4, FAM46A, FAM98A, FKBP3, FXR2, G3BP2, GLTSCR2, GSPT2, GTF2F1, GTPBP10, HADHB, HDGF, hnRNPE1, HNRPDL, HSPB1, KIAA1324, LARP1, LARP4, LARP4B, LIN28A, LUC7L, MAK16, MATR3, MBNL2, MEPCE, MRPL39, MTDH, NDUFV3, NUFIP2, NUSAP1, PABPC1, PABPC5, PCBP4, PEG10, PPAN, PPIL4, PRPF3, PRPF31, PRRC2B, PTRH1, PUS7, RBM33, RBM38, RBMX2, RPL10A, RPL14, RPL15, RPLPO, RPS20, RPUSD3, RPUSD4, RTN4, SERBP1, SF3A3, SFRS10, SFRS13A, SFRS2IP, SLC7A9, SMN1, SPATS2L, SRSF5, SRSF8, THOC1, TRA2A, TRIM39, TUFM, UBAP2L, UTP23, XPO5, XRN1, YWHAE, or ZRANB2 and
      (ii) an RNA-targeting CRISPR-associated protein;
   (b) delivering the modulation unit into the cell; and
   (c) detecting change in the target RNA translation, wherein the modulation unit modulates translation of the target RNA in the cell.

2. The method of claim 1, further comprising delivering a guide RNA into the cell, wherein the guide RNA is complementary to the target RNA.

3. The method of claim 1, wherein the RBP is fused to the RNA-targeting CRISPR-associated protein.

4. The method of claim 1, wherein the delivering step (b) comprises lipofection.

5. The method of claim 1, wherein the delivering step (b) comprises a virus-based delivery.

6. The method of claim 5, wherein the virus-based delivery comprises adeno-associated virus or lentivirus.

7. The method of claim 1, wherein the target RNA is an endogenous mRNA.

8. The method of claim 1, wherein the target RNA is a non-coding RNA.

9. The method of claim 1, wherein the translation of the target RNA is upregulated.

10. The method of claim 1, wherein the translation of the target RNA is downregulated.

11. The method of claim 1, wherein the modulation unit consists essentially of:
- (i) an RNA binding protein (RBP), wherein the RNA binding protein is selected from the group consisting of: AIMP1, BOLL, CLK3, CNOT7, CPEB4, CPSF5, DAZ2, DAZ4, DAZAP1, DDX6, EIF2S2, F3B3S, HSPB1, HNRNPD, IFIT2, LARP1, MEX3C, MTDH, NANOS3, NRNP27, PABPC1, PARN, PLRG1, PRPF3, RBFOX1, SNRPA, SRPR, THOC1, TOB1, TOB2, UBAP2L, or YWHAE; and
- (ii) RCas9.

* * * * *

UNITED STATES PATENT AND TRADEMARK OFFICE
CERTIFICATE OF CORRECTION

PATENT NO. : 12,139,710 B2  
APPLICATION NO. : 17/512270  
DATED : November 12, 2024  
INVENTOR(S) : Eugene Yeo and En-Ching Luo Page 1 of 1

It is certified that error appears in the above-identified patent and that said Letters Patent is hereby corrected as shown below:

In the Claims

Column 57, Line 67, in Claim 1, delete "RPLPO," and insert -- RPLP0, --.

Signed and Sealed this  
Seventh Day of January, 2025

Derrick Brent  
*Acting Director of the United States Patent and Trademark Office*

SEQUENCE LISTING

```
<160> NUMBER OF SEQ ID NOS: 6

<210> SEQ ID NO 1
<211> LENGTH: 32
<212> TYPE: RNA
<213> ORGANISM: Homo sapiens

<400> SEQUENCE: 1
ggcgggugug ggguccuucc cccgccccccc cc                                     32

<210> SEQ ID NO 2
<211> LENGTH: 47
<212> TYPE: RNA
<213> ORGANISM: Homo sapiens

<400> SEQUENCE: 2
accggcgaug cggcggcguu auucccauga cccgccgggc agcuucc                      47
```

```
<210> SEQ ID NO 3
<211> LENGTH: 21
<212> TYPE: RNA
<213> ORGANISM: Homo sapiens

<400> SEQUENCE: 3
gggcccccgg cggcgggggc a                                              21

<210> SEQ ID NO 4
<211> LENGTH: 15
<212> TYPE: RNA
<213> ORGANISM: Homo sapiens

<400> SEQUENCE: 4 uccccegccc caccc                                                     15

<210> SEQ ID NO 5
<211> LENGTH: 15
<212> TYPE: RNA
<213> ORGANISM: Homo sapiens

<400> SEQUENCE: 5
ugccaggugg ggagu                                                     15

<210> SEQ ID NO 6
<211> LENGTH: 14
<212> TYPE: RNA
<213> ORGANISM: Homo sapiens

<400> SEQUENCE: 6
acucuagucu ggca                                                      14
```